United States Patent
Bowers et al.

(10) Patent No.: US 12,203,143 B2
(45) Date of Patent: *Jan. 21, 2025

(54) **METHODS AND KITS TO IDENTIFY *KLEBSIELLA* STRAINS**

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: Jolene Bowers, Flagstaff, AZ (US); Elizabeth Driebe, Flagstaff, AZ (US); David Engelthaler, Flagstaff, AZ (US); Paul Keim, Flagstaff, AZ (US); Darrin Lemmer, Flagstaff, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/588,196

(22) Filed: Jan. 28, 2022

(65) Prior Publication Data
US 2022/0145375 A1    May 12, 2022

Related U.S. Application Data

(63) Continuation of application No. 16/083,860, filed as application No. PCT/US2017/022211 on Mar. 14, 2017, now Pat. No. 11,248,270.

(60) Provisional application No. 62/307,632, filed on Mar. 14, 2016.

(51) Int. Cl.
| | |
|---|---|
| *C12Q 1/689* | (2018.01) |
| *C12Q 1/6827* | (2018.01) |
| *C12Q 1/6853* | (2018.01) |
| *C12Q 1/686* | (2018.01) |

(52) U.S. Cl.
CPC .......... *C12Q 1/689* (2013.01); *C12Q 1/6827* (2013.01); *C12Q 1/6853* (2013.01); *C12Q 1/686* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 11,098,349 B2 * | 8/2021 | Driebe | C12Q 1/686 |
| 2004/0029129 A1 * | 2/2004 | Wang | C07K 14/26 |
| | | | 435/254.2 |

OTHER PUBLICATIONS

Colman et al PLoS ONE. 2015. 10(5): e0126626, 18 pages and Table S1 (Year: 2015).*
Craig, W.A. Crit Care Clin. 2011. 27: 107-121 (Year: 2011).*
Mitsuhashi, M. Journal of Laboratory Analysis. 1996. 10: 285-293 (Year: 1996).*

* cited by examiner

*Primary Examiner* — Carla J Myers
(74) *Attorney, Agent, or Firm* — Rodney J. Fuller; BOOTH UDALL FULLER, PLC

(57) ABSTRACT

The present invention provides a method of detecting one or more *Klebsiella* species within a sample from a subject, the method comprising: subjecting DNA and/or RNA from the sample to a PCR amplification reaction using primer pairs targeting species-specific canonical single nucleotide polymorphisms (canSNPs); and analyzing amplification products resulting from the PCR amplification reaction to detect the one or more *Klebsiella* species. The present invention also provides a kit for detection of one or more *Klebsiella* species, *Klebsiella* clonal groups, AMR genes, and/or virulence genes, the kit comprising primer pairs targeting species-specific canSNPs, *K. pneumoniae* genes M1 and M2, clonal group-specific canSNPs, AMR genes, and/or virulence genes.

7 Claims, 5 Drawing Sheets
Specification includes a Sequence Listing.

KlebSeq ASAP Results for Sample: F4-Mom-TP2

Alignment statistics
Total reads: 132184
Mapped reads: 70104
Ummapped reads: 62080
Aligner used: bowtie2

Analysis parameters
Depth filter: 10x
Breadth filter: 80%
Proportion filter: 10%

Summary for Sample: F4-Mom-TP2

| *Klebsiella* species and strain types detected | Antimicrobial resistance determinants detected | Other phenotype determinants detected |
|---|---|---|
| *Klebsiella pneumoniae* | npmA (aminoglycoside resistance)<br>sul2 (TMP-SMX resistance)<br>aph3-I (aminoglycoside resistance)<br>strB (streptomycin resistance)<br>fosA (fosfomycin resistance) | Yersiniabactin siderophore |

Species and strain identification assays for sample: F4-Mom-TP2

| Assay name | Average Read Depth | Coverage Breadth | Significance | SNPs found |
|---|---|---|---|---|
| Kp_M1_UT1 | 814.01 | 100% | Klebsiella pneumoniae present | details... |
| Kp_M2_UT1 | 925.17 | 100% | Klebsiella pneumoniae present | |
| Kvari_UT | 371.19 | 98.95% | Not Klebsiella variicola | details... |

Antimicrobial resistance assays for sample: F4-Mom-TP2

| Assay name | Average Read Depth | Coverage Breadth | Significance | SNPs found |
|---|---|---|---|---|
| npmA_UT | 71.98 | 100% | Resistant to all aminoglycosides | details... |
| sul2_UT1 | 135.43 | 100% | Resistant to trimethoprim-sulfamethoxazole | |
| aph3-1_UT | 2046.08 | 100% | Resistant to kanamycin, neomycin | details... |

FIG. 2

METHODS AND KITS TO IDENTIFY KLEBSIELLA STRAINS

CROSS REFERENCE TO RELATED APPLICATIONS

This application is a continuation of U.S. patent application Ser. No. 16/083,860, filed on Sep. 10, 2018 (published as US20190078141), which is the U.S. National Stage of International Application No. PCT/US2017/022211, filed on Mar. 14, 2017, which claims priority to and the benefit of U.S. Provisional Application Ser. No. 62/307,632, filed on Mar. 14, 2016, the contents of each of which are hereby incorporated by reference in their entirety.

GOVERNMENTAL SUPPORT OF APPLICATION

This invention was made with governmental support under grant number R01AI090782 awarded by the National Institutes of Health (NIH). The United States government has certain rights in the invention.

REFERENCE TO SEQUENCE LISTING SUBMITTED ELECTRONICALLY

The official copy of the sequence listing is submitted electronically via EFS-Web as an ASCII-formatted sequence listing with a file named "91482.210_Sequence_Listing.txt" created on Mar. 13, 2017, and having a size of 50 kilobytes, and is filed concurrently with the specification. The sequence listing contained in this ASCII-formatted document is part of the specification and is herein incorporated by reference in its entirety.

TECHNICAL FIELD

The present invention relates to the field of detection of *Klebsiella* species that cause health care-acquired infection (HAI) in patients and healthcare workers.

BACKGROUND

*Klebsiella pneumoniae* has been a leading HAI agent for decades (1, 2). The emergence of multidrug-resistant *K. pneumoniae*, especially extended-spectrum β-lactamase (ESBL) producers and carbapenemase producers, has elevated the morbidity and mortality rates and health care costs associated with *K. pneumoniae* to highly significant levels (3-6). Health care- and outbreak-associated strain types of *K. pneumoniae* that appear highly transmissible and have a propensity for antimicrobial resistance (AMR) or virulence gene acquisition are a growing proportion of the *K. pneumoniae* species (7-18). Sequence type 258 (ST258), the crux of the worldwide carbapenemase-producing Enterobacteriaceae (CPE) threat, has disseminated rapidly around the world's health care systems despite its recent emergence (17). Its progenitor strains in clonal group 258 (CG258) also cause outbreaks and carry many important ESBL- and carbapenemase-encoding genes (9, 19-21). Several other strain types, such as those in CG14, CG20, and CG37, also frequently appear as multidrug resistant and in outbreak situations (7, 10, 12, 15).

Host colonization is likely an important reservoir driving the transmission of these strains. In the health care environment, intestinal colonization of *K. pneumoniae* is a risk factor for infection (22-24), and carriers of CPE are at high risk for invasive disease (25). Rates of CPE and ESBL-producing *K. pneumoniae* colonization are rising in patient and health care worker populations, increasing the size of the reservoir and increasing chances of transmission (26, 27). Asymptomatic transmission of multidrug-resistant strains is rapid (16, 28), and transmission events that lead to outbreaks often go undetected (29, 30). Early detection of *K. pneumoniae* colonization of patients, especially multidrug-resistant *K. pneumoniae* or epidemic strain type colonization, is now considered critical to infection control (24, 30-33).

Infection control programs that include the detection and isolation of carriers have repeatedly been successful in markedly decreasing multidrug-resistant or epidemic strain infections (31, 34-37), but this practice is uncommon for several reasons. Many of these programs use culture-based methods for detecting CPE or ESBL producers, which have several limitations, including turnaround time, narrow application, fair sensitivity and specificity, and extensive labor for high-throughput screening (31, 38). PCR-based assays are rapid but often use DNA from culture, and a limited number of tests can be run simultaneously, potentially missing important AMR genes not previously known to circulate in a given locale (31, 39).

Next-generation sequencing has gained a foothold in health care with whole-genome sequencing (WGS) for outbreak detection, transmission mapping, and source tracing (40, 41), microbiome sequencing (e.g., targeted 16S rRNA gene sequencing) to understand microbial population structure (42, 43) and with metagenomic sequencing to attempt to determine all of the genetic factors present (44). Although metagenomic sequencing does not require an a priori understanding of the genetic targets in a clinical sample, it does have significant drawbacks, limiting its translation to the clinical microbiology laboratory. Chief among these are that (i) the required amount of sequencing space increases the cost and time, (ii) limited coverage across targets lessens the confidence in diagnostic calls, and (iii) the necessary computing power and highly complex analysis limit the ability for local analysis. Targeted amplicon sequencing, on the other hand, allows for rapid, cost-effective, highly multiplexed, and accurate detection of numerous clinically important targets directly in clinical samples (45). Such assays have recently been approved by the FDA for clinical diagnostics (46). There is a continuing need for compositions and methods for the diagnosis of HAI caused by *Klebsiella* species that address these challenges to efficient detection and treatment.

SUMMARY

HAIs kill tens of thousands of people each year and add significantly to health care costs. Multidrug-resistant and epidemic strains are a large proportion of HAI agents, and multidrug-resistant strains of *Klebsiella pneumoniae*, a leading HAI agent, have caused an urgent public health crisis. In the health care environment, patient colonization by *K. pneumoniae* precedes infection, and transmission via colonization leads to outbreaks. Periodic patient screening for *K. pneumoniae* colonization has the potential to curb the number of HAIs.

The present invention provides a new amplicon sequencing tool, KlebSeq, for screening and surveillance that detects and characterizes *Klebsiella* bacteria in complex samples such as wound and nasal swabs or fecal samples without culturing. KlebSeq includes a sizeable panel of assays for species identification, strain identification, and important AMR and virulence gene targets designed to generate information for health care epidemiology and infection prevention. KlebSeq also includes an analysis pipeline for instant interpretation of the data. Results from the screening of a patient population with this system would rule in or rule out the possibilities of particular transmission events and identify patients carrying high-risk strains like ST258 or other multidrug-resistant *Klebsiella* strains. The highly multiplexed nature of KlebSeq greatly expands the capacity of a single sequencing run, minimizing costs, and allows for high-throughput patient sample testing.

Herein, we describe the design and validation of KlebSeq, a highly informative screening tool that detects *Klebsiella* species and identifies clinically important strains and characteristics by using highly multiplexed amplicon sequencing without a live-culturing step. We demonstrate the utility of this tool on several complex specimen types, including urine, wound swabs and tissue, and several types of respiratory and fecal specimens, showing *K. pneumoniae* species and clonal group identification and antimicrobial resistance and virulence profiling, including capsule typing. Use of this amplicon sequencing tool to screen patients for *Klebsiella* carriage could inform health care staff of the risk of infection and outbreak potential. KlebSeq also serves as a model for next-generation molecular tools for public health and health care, as expansion of this tool can be used for several other HAI agents or applications.

In some embodiments, the present invention provides a method of detecting one or more *Klebsiella* species within a sample from a subject, the method comprising: subjecting DNA and/or RNA from the sample to a PCR amplification reaction using primer pairs targeting species-specific canonical single nucleotide polymorphisms (canSNPs); and analyzing amplification products resulting from the PCR amplification reaction to detect the one or more *Klebsiella* species.

In other embodiments, the method further comprises subjecting DNA and/or RNA from the sample to a PCR amplification reaction using primer pairs targeting *K. pneumoniae* genes M1 and M2; and analyzing amplification products resulting from the PCR amplification reaction to detect the *K. pneumoniae* genes M1 and M2.

In yet other embodiments, the primer pairs comprise a universal tail sequence. In one embodiment, the primer pairs contain sequences selected from the group consisting of SEQ ID NOs: 1-10.

In some aspects, the one or more *Klebsiella* species are selected from the group consisting of *K. pneumoniae, K. quasipneumoniae, K. oxytoca,* and *K. variicola*.

In other aspects, the method further comprises detecting one or more *Klebsiella* clonal groups in the sample by subjecting DNA and/or RNA from the sample to a PCR amplification reaction using primer pairs targeting clonal group-specific canSNPs and analyzing amplification products resulting from the PCR amplification reaction to detect the one or more *Klebsiella* clonal groups.

In yet other aspects, the primer pairs targeting clonal group-specific canSNPs contain sequences selected from the group consisting of SEQ ID NOs: 11-84.

In other embodiments, the method further comprises detecting one or more antimicrobial resistance (AMR) genes in the *Klebsiella* species in the sample by subjecting DNA and/or RNA from the sample to a PCR amplification reaction using primer pairs targeting AMR genes and analyzing amplification products resulting from the PCR amplification reaction to detect the one or more AMR genes.

In yet other embodiments, the primer pairs targeting AMR genes contain sequences selected from the group consisting of SEQ ID NOs: 85-248.

In some implementations, the method further comprises detecting one or more virulence genes in the *Klebsiella* species in the sample by subjecting DNA and/or RNA from the sample to a PCR amplification reaction using primer pairs targeting virulence genes and analyzing amplification products resulting from the PCR amplification reaction to detect the one or more virulence genes. In one implementation, the primer pairs targeting virulence genes contain sequences selected from the group consisting of SEQ ID NOs: 249-281.

In certain aspects, the PCR amplification reaction is a multiplex amplification reaction. In other aspects, the amplification products are analyzed by next-generation sequencing (NGS) to determine the sequence of each amplification product.

In yet other aspects, the sample is a wound swab, a nasal swab, rectal swab, skin swab, saliva, feces, urine, whole blood, serum, plasma, or buffy coat.

In some embodiments, the subject is an animal. In one embodiment, the animal is a human.

In other aspects, the present invention is directed to a kit for detection of one or more *Klebsiella* species, *Klebsiella* clonal groups, AMR genes, and/or virulence genes, the kit comprising primer pairs targeting species-specific canSNPs, *K. pneumoniae* genes M1 and M2, clonal group-specific canSNPs, AMR genes, and/or virulence genes.

In some aspects, the primer pairs comprise a universal tail sequence. In one aspect, the primer pairs contain sequences selected from the group consisting of SEQ ID NOs: 1-281. In yet another aspect, the kit further comprises a nucleotide polymerase, buffer, diluent, and/or excipient.

BRIEF DESCRIPTION OF THE DRAWINGS

FIG. 2 depicts a partial sample output of KlebSeq ASAP report; some AMR gene assays and the virulence gene assays are hidden from view to limit the size of the image. The top box shows a summary of what was detected according to selected ASAP filters. Details of each assay appear below that. If additional SNPs are detected in comparison to the assay reference, hovering over "details . . . " expands a list of the SNPs. Clicking on an assay name pops up a graph of coverage depth across the reference sequence.

DETAILED DESCRIPTION

Figure 1:
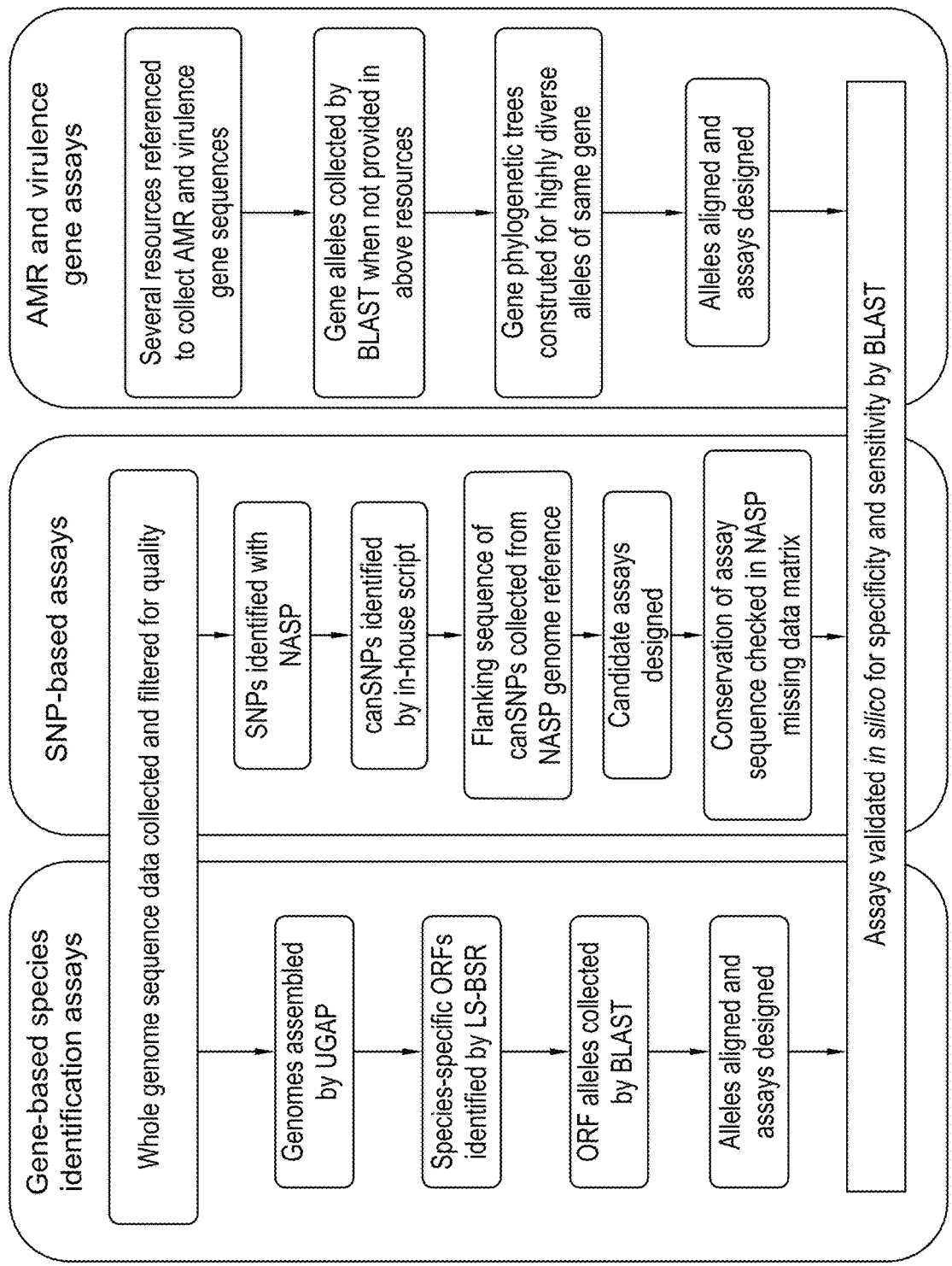
FIG. 1 depicts a workflow of the amplicon sequencing target library and assay development pipeline.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, "amplification reaction" refers to a method of detecting target nucleic acid by in vitro amplification of DNA or RNA.

As used herein, "polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

The term "primer" refers to DNA oligonucleotides complementary to a region of DNA and serves as the initiation of amplification reaction from the 5' to 3' direction.

The term "primer pair" refers to the forward and reverse primers in an amplification reaction leading to amplification of a double-stranded DNA region of the target.

The term "target" refers to a nucleic acid region bound by a primer pair that is amplified through an amplification reaction. The PCR "product" or "amplicon" is the amplified nucleic acid resulting from PCR of a set of primer pairs.

The term "multiplex amplification reaction" herein refers to the detection of more than one template in a mixture by the addition of more than one set of oligonucleotide primers.

In certain aspects, the methods and kits of the present invention are used as a surveillance tool for a health care facility. If the KlebSeq assays, methods, and/or kits produce positive results (i.e., detect the presence of the *Klebsiella* species, clonal group, AMR gene, and/or virulence gene) this result could be used be to limit the subsequent infection and transmission of the pathogenic organism to another patient or health care worker. The specific measures taken would depend on the facility.

In other aspects, the KlebSeq assays, methods, and/or kits disclosed herein are used as a diagnostic tool. Upon detection of a positive result in a subject, the subject is treated with an antibiotic regimen. In one aspect, the antibiotic regimen depends on which assays are positive and/or on the facility.

In one embodiment, in cases of detection of pneumonia caused by *Klebsiella* the subject is treated with aminoglycosides and/or cephalosporins. In another embodiment, with results indicating ESBL production by the *Klebsiella* the subject is treated with carbapenem. In some aspects, the specific treatment also depends on which organ system is affected.

In some embodiments, a threshold is used to generate a positive result. In one aspect, an amplicon sequence must match the reference sequence at the threshold or above in order to know that the organism being identified is indeed what the assay tests for. For example, if the threshold is 97% for a *Klebsiella pneumoniae* assay, then amplicon sequences that are less than 97% identical to the reference sequence will be ignored, as they represent organisms that are not *Klebsiella pneumoniae* and are a negative result on the assay. Sequences at 97% or greater similarity to the reference are a positive result for the *Klebsiella pneumoniae* assay. This may be particularly useful for certain assays where there is cross-reactivity of the primers with non-targets, but amplicon sequencing can distinguish targets from non-targets.

In some aspects, the threshold is about 90%, about 91%, about 92%, about 93%, about 94%, about 95%, about 96%, about 97%, about 98%, about 99% or about 100%.

As described in greater detail herein, some embodiments of the invention may include amplicon-based sequencing of the one or more markers to make the aforementioned determinations. Some embodiments of the invention include systems and methods of preparing samples for one or more downstream processes that can be used for assessing one or more markers for any of the previously mentioned purposes. Some embodiments of the invention may comprise a universal indexing sequencing strategy for use in downstream sequencing platform processes. By way of example only, some embodiments of the invention comprise a universal indexing sequencing strategy that can be used to amplify multiple genomic regions (e.g., markers, as described below) from a DNA sample simultaneously in a single reaction for the sequencing of one or more amplicons. One or more embodiments of the invention can be used with any desired sequencing platform, such as the ILLUMINA® Next Generation Sequencing (e.g., MiSEQ) platform, Life Technologies' Ion Torrent System, or any other sequencing system now known or developed in the future.

Some embodiments may be configured to enable relatively simple, rapid (e.g., microorganism-culture independent), inexpensive, and efficient preparation of samples for use on, in, and/or with downstream sequencing platforms. For example, some embodiments may use a sequence coupled to one or more oligonucleotides/primers (as used herein, oligonucleotides and primers are used interchangeably). More specifically, one or more amplicons per sample can be generated using a hybrid oligonucleotide that is designed for amplification of a marker and incorporation of at least one universal tail sequence into the resulting amplicon. As a result, additional steps that may be conventionally required to prepare samples for sequencing can be limited or removed entirely. Further information regarding the universal tail, amplicon-based sequencing strategy can be found in PCT/US2014/064890, which is hereby incorporated by reference in its entirety for all purposes.

In some embodiments, the methodology may include performing downstream sequencing on one or more amplicons. For example, in order to minimize and/or eliminate the need for cultures of microorganisms or large inputs of nucleic acids, methodologies of the instant invention may include an initial PCR step to create amplicons that correspond to the one or more pre-selected markers. As such, some embodiments require only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of some conventional systems.

Some embodiments of the invention can be used for and/or in complement with high-throughput amplicon sequencing of markers, which can be very useful for a variety of molecular genetic genotyping/predicted-phenotyping applications, including clinical sample analysis. For example, use of the systems and methods of the invention can be employed with sequencing platforms to provide rapid, high-yield sequence data, which can enable the sequencing of multiple markers/amplicons from many samples in a relatively short period of time. Specifically, in some embodiments, amplicons can be selected and PCR reactions can be designed to provide information that can be used to make clinically relevant determinations after sequencing of the amplicons.

In some preferred aspects, the methodology may include creating a series of oligonucleotides designed to provide multiplexed amplification of one or more markers to produce the desired amplicons. In particular, the one or more markers and amplicons thereof can be selected/amplified to provide users with clinically relevant information related to identification of one or more potentially infectious microorganisms and phenotypic and genotypic information about the microorganisms. After production of the amplicons (e.g., via PCR amplification), which may include the universal tail sequences, the method may include processing the resulting amplicons for downstream sequencing and thereafter sequencing the processed amplicons. After processing and analysis of the resulting sequencing data, one of skill in the art can make any necessary determinations regarding the identification of one or more microorganisms that may have been contained within the sample and predicted-phenotypic and/or genotypic information revealed.

Generally, some embodiments of the present invention can be used to detect, identify, assess, sequence, or otherwise evaluate a marker. A marker may be any molecular structure produced by a cell, expressed inside the cell, accessible on the cell surface or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof. Alternatively, a marker may be represented by a protein sequence. The concept of a marker is not limited to the exact nucleic acid sequence or protein sequence or products thereof; rather it encompasses all molecules that may be detected by a method of assessing the marker. Without being limited by the theory, the detection, identification, assessment, sequencing, or any other evaluation of the marker may encompass an assessment of a change in copy number (e.g., copy number of a gene or other forms of nucleic acid) or in the detection of one or more translocations. Moreover, in some embodiments, the marker may be relevant to a particular phenotype or genotype. By way of example only, in some embodiments, the marker may be related to phenotypes including antibiotic resistance, virulence, or any other phenotype.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

In some aspects, the markers may include one or more sets of amplifiable nucleic acids that can provide diagnostic information about the microorganisms. For example, the markers may include amplifiable nucleic acid sequences that can be used to assess the presence and/or absence of one or more microorganism that may have the potential to cause a diseased state in the subject. In some embodiments, the markers may include amplifiable nucleic acid sequences that can be used to identify one or more of the following exemplary microorganisms: *Klebsiella* spp. (including but not limited to *K. granulomatis, K. oxytoca, K. pneumoniae, K. terrigena,* and *K. variicola*).

In some embodiments, the methods may include the use of one or more than one marker per microorganism. Moreover, in some embodiments, one or more of the microorganisms may not be considered pathogenic to certain subjects, but the methodology employed herein can still rely on detection of pathogenic and non-pathogenic microorganisms for differential diagnoses/diagnostics. In some embodiments, the oligonucleotides (with or without the universal tail sequences detailed herein) listed in Table 4 can be used with embodiments of the invention to amplify one or more markers from the microorganisms to provide diagnostic/identification information to the user.

Moreover, in some embodiments, one or more the markers associated with the plurality of microorganisms can be amplified in a multiplex manner. For example, in some aspects, nucleic acids can be obtained from the sample and the oligonucleotides used to amplify one or more of the markers used to identify/diagnose can be added to a single mixture to produce a plurality of amplicons in a single reaction mixture. In other aspects, the oligonucleotides can be added to multiple mixtures to provide for the creation of multiple amplicons in multiple mixtures.

Moreover, in some embodiments, one or more the markers can be amplified in a multiplex manner. For example, in some aspects, nucleic acids can be obtained from the sample and the oligonucleotides used to amplify one or more of the markers used to identify the strain of the microorganism can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the markers used to identify microorganisms/diagnose an infection can also occur in a multiplex manner such that some or all of the amplicons are generated in a single reaction for a particular sample. In other aspects, amplification of the markers used to identify microorganisms/diagnose an infection can occur in multiple reaction vessels. Overall, as described in greater detail below, regardless of the multiplex nature of some embodiments of the invention, after amplification of the markers, the method may include processing and sequencing the resulting amplicons to provide information related to the identification, characterization, and strain identity of one or more microorganisms that may be present within the sample.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points ($C_P$) and cycle threshold values ($C_t$) at a constant level of fluorescence; or $C_P$ acquisition according to established mathematic algorithm.

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one marker-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

The algorithm for $C_t$ values in real time-PCR calculates the cycle at which each PCR amplification reaches a significant threshold. The calculated $C_t$ value is proportional to the number of marker copies present in the sample, and the $C_t$ value is a precise quantitative measurement of the copies of the marker found in any sample. In other words, $C_t$ values represent the presence of respective marker that the primer sets are designed to recognize. If the marker is missing in a sample, there should be no amplification in the Real Time-PCR reaction.

Alternatively, the $C_P$ value may be utilized. A $C_P$ value represents the cycle at which the increase of fluorescence is highest and where the logarithmic phase of a PCR begins. The LIGHTCYCLER® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and bacteria).

With respect to use of the sample or biological sample, embodiments of the claimed methodology provide improvements compared to conventional methodologies. Specifically, conventional methodologies of identifying and characterizing microorganisms include the need for morphological identification and culture growth. As such, conventional methodologies may take an extended period of time to identify the microorganism and may then require further time to identify whether the microorganism possesses and certain markers. Some embodiments of the invention can provide a user with information about any microorganisms present in a sample without the need for additional culturing because of the reliance of nucleic acid amplification and sequencing. In other words, direct extraction of nucleic acids coupled with amplification of the desired markers and downstream sequencing can reduce significantly the time required to obtain diagnostic and strain identifying information.

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfurylase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Nucleic acid sequences may be identified by the IUAPC letter code which is as follows: A—Adenine base; C—Cytosine base; G—guanine base; T or U—thymine or uracil base; I—inosine base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, as previously mentioned, the method may include the use of massively parallel sequencing, as detailed in U.S. Pat. Nos. 8,431,348 and 7,754,429, which are hereby incorporated by reference in their entirety.

Some embodiments of the invention comprise multiple steps and/or processes that are carried out to execute the universal tail indexing strategy to prepare amplicons corresponding to desired markers for sequencing. In some embodiments, one or more makers for a given sample or template can be selected, as described above. Some embodiments of the invention can be used in conjunction with an analysis of one or more markers (e.g., genes/alleles) associated with a particular phenotype (e.g., virulence).

After selection of the markers, marker-specific primers/oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 100 bp, 150 bp, 200 bp, 250 bp, 300 bp, 350 bp, 400 bp, 450 bp, 500 bp, 1,000 bp, or any size amplicon greater in size or therebetween.

As previously mentioned, some embodiments of the invention may include a multiplex PCR reaction. For example, marker-specific primers can be designed for multiple markers or multiple regions of the same marker such that multiple amplicons of between about 50 bp and 1,000 bp are being produced within a single PCR reaction vessel. In other words, the forward and reverse primers can be designed to function within a given set of temperature parameters such that more than one amplicon can be successfully amplified from a given template within a single PCR reaction mixture. As such, multiple amplicons can be prepared using the universal tail indexing strategy for sequencing preparation.

In some embodiments, the forward and reverse primers that have been designed for each of the markers can be modified to include a universal tail. For example, the universal tail sequences can be relatively or completely unique sequences of nucleotides that are coupled to the 5' ends of some or all of the forward and reverse marker-specific primers. In some aspects, the universal tail sequences can be selected such that there is little to no overlap in sequence between portions of the markers that are being amplified and the universal tail sequences. Moreover, the universal tail sequences can comprise a length between ten and twenty nucleotides in length. In some embodiments, the universal tail sequences can be any other length, as desired by the user to meet the needs and requirements of the reaction. As such, the universal tail sequences can exhibit a relatively negligible impact on binding of the forward and reverse marker-specific primers to the template sequence to enable amplification. Moreover, as a result of being included on the 5' end of the forward and reverse marker-specific primers, the universal tail sequences will form a portion of the resulting amplicons. In addition, in some aspects of the invention, the sequences selected for the universal tail sequences can be at least partially correlated with the chemical composition of the template nucleic acids. For example, in some aspects, the sequences selected for the universal tail sequences can be at least partially correlated with the G-C content of the organism from which the template is isolated.

In some aspects, some or all of the universal tail sequences can be at least partially unique. In some embodiments, each of the 5' ends of all of the forward marker-specific primers within a given PCR assay mixture can comprise the same or a similar universal tail sequence (e.g., a first universal tail sequence or UT1). Similarly, each of the 5' ends of all of the reverse marker-specific primers within the same PCR assay mixture can comprise a second universal tail sequence (UT2) that differs from the first universal tail sequence. As such, each respective sample from which a template sequence is used in the multiplex PCR assay will have two unique universal tail sequences. Accordingly, each forward and reverse marker-specific primer within a multiplex PCR mixture will include a unique universal tail sequence. For example, if the PCR includes 35 different samples, 35 universal tail sequences can be employed for the forward primers in each of the 35 unique reactions (i.e., not including technical replicates) and 35 universal tail sequences can be employed for the reverse primers in each of the 35 unique reactions (i.e., not including technical replicates). Overall, the forward and reverse marker-specific primers that each comprise the universal tail sequences can comprise a generally short length (e.g., 25-50 bp), which can facilitate simultaneous amplification of multiple targets in a single reaction.

In addition, some embodiments of the invention may comprise performing quantitative PCR to optimize the multiplex PCR assay. For example, after design of the forward and reverse marker-specific primers that each include a universal tail sequence, the contemplated multiplex PCR assays can be performed using quantitative PCR (e.g., using DNA as a template) to assess relative quantities of the amplicons produced. Accordingly, the sequence coverage of each amplicon is considered to be equal if the quantities of the amplicons produced by the multiplex quantitative PCR appear to be equal. If the quantities of the amplicons produced by the multiplex quantitative PCR do not appear to be equal, the forward and/or reverse marker-specific primers can be altered and re-optimized until adequate quantities of amplicons are produced.

After design and adequate optimization of the multiplex PCR assay comprising multiple forward and reverse marker-specific primers that each includes universal tail sequences, the multiplex PCR can be performed to obtain the amplicons associated with the above-described markers. In some embodiments, template that has been previously isolated from a sample can be used for the amplification of the amplicons. In some aspects, multiple PCR reaction replicates can be performed for each sample template and one or more control templates.

In some embodiments, after successful production of the amplicons during the multiplex PCR assay, the resulting amplicons can be further processed to provide sequencing-ready amplicons. For example, some embodiments of the invention may comprise an indexing extension step. In some aspects, the indexing extension step may comprise extending the optimized multiplex amplicons using a set of indexing and common primers that recognize the respective universal tail sequences used for the particular group of amplicons in a minimal cycle PCR assay (e.g., 5-10 total cycles). In particular, each multiplex set of amplicons to be sequenced can be extended with a different set of index oligonucleotides and common oligonucleotides that recognize UT1 and UT2, respectively. In some aspects, the index sequence of the index oligonucleotides can be custom designed to allow for the selection of an index sequence from potentially thousands of different index sequences.

After this step, the resulting products include a set of amplicons for each sample/template that comprise the same index and any necessary sequences that may be required for a particular sequencing platform (e.g., platform sequences associated with the ILLUMINA® Next Generation sequencing platform). Thereafter, the resulting extension-reaction products can be quantified, pooled, and sequenced using a desired platform. In some aspects, the inclusion of the universal tail sequences on the index and common primers can coincide with the use of genomic and index read primers in the mixture of sequencing primer reagents. For example, some embodiments of the invention are capable of pooling multiple amplicons with multiple indices in a single sequencing run to provide 40,000×-95,000× coverage across the amplicons. In other embodiments, the systems and methods associated with the invention can be configured to provide any level of sequencing coverage that is desirable to the user (e.g., higher or lower that the coverage levels discussed above). In some embodiments, after sequencing and generation of the sequence data, the resulting data can be demultiplexed and the sequence files can be aligned to the appropriate references sequences for subsequent sequence analyses.

Embodiments of the invention offer additional advantages relative to conventional systems. For example, some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems. Moreover, the inclusion of non-desirable template materials can also interfere in one or more downstream processes in conventional systems and methods. For example, if an investigation is being conducted that focuses on one or more organisms that may be associated with another organism (e.g., bacteria associated with a human); the sampling of the target organism may result in template contamination from the host organism.

In particular, in some aspects, obtaining samples of pathogenic or commensal bacteria from, on, or within a human may also result in the collection of human tissue. As such, when isolating the template, human nucleic acids may contaminate the bacterial template. Some embodiments of the invention are configured such that the contaminating template (e.g., from a human) would not interfere with downstream processes, including sequencing. For example, some embodiments of the invention operate such that only a limited amount of starting template (e.g., 500 femtograms or greater) can be used. Moreover, some embodiments are also configured such that the starting material (e.g., template contaminated with foreign nucleic acids) can still produce the required amplicons for sequencing in the presence of more than a 1,000-fold excess of contaminating template with no discernible inhibition of the multiplex PCR.

In certain aspects, the present invention provides an assay that works with as little as about 1 pg, about 900 fg, about 800 fg, about 700 fg, about 600 fg, about 500 fg, about 400 fg, about 300 fg, about 200 fg, or about 100 fg of genomic DNA.

The following examples are given for purely illustrative and non-limiting purposes of the present invention.

EXAMPLES

Example 1. Materials and Methods

Samples

Isolates for target identification and assay validation and DNA extracted from clinical specimens were acquired through collaborations with a large hospital reference laboratory that receives specimens from 10 system-wide medical centers in Arizona and from a high-volume private reference laboratory that receives specimens from regional inpatient, long-term care, and outpatient facilities. Isolates were identified with Vitek 2 (bioMérieux). Clinical specimen types included various respiratory specimens (nasal, ear, and throat swabs; sputum samples; tracheal aspirates; and bronchial alveolar lavage samples), urine, and wound swabs or tissue. DNA was extracted from isolates with the Qiagen DNeasy Blood and Tissue kit with additional lytic enzymes when appropriate. DNA was extracted from clinical specimens by NucliSENS easyMAG (bioMérietux, Durham, NC). DNA from healthy donor fecal samples was acquired from a family microbiome study; samples had been collected from members of seven families over multiple time points. DNA was extracted in accordance with the Earth Microbiome Project protocol (47). All of the samples were obtained from studies approved by the institutional review boards of the participating institutions.

Assay Target Identification and Assay Design.

FIG. 1 illustrates the methodologies and resources, also described below, utilized to amass a target library and develop several types of amplicon sequencing assays.

WGS, Single Nucleotide Polymorphism (SNP) Detection, and Phylogenetic Analysis

In-house genome libraries were prepared from 31 *Klebsiella* isolates and 6 non-*Klebsiella* isolates (to validate KlebSeq assays) with a 500-bp insert size with the KAPA Library Preparation kit and Standard PCR Library Amplification (Kapa Biosystems, Wilmington, MA) and sequenced on Illumina's GAIIx or MiSeq. Additional in-house genomes that we have previously described were also included and comprised 111 *K. pneumoniae*, 1 *K. quasipneumoniae*, and 5 *K. variicola* genomes. Public genome sequence data from 256 *K. pneumoniae*, 18 *K. quasipneumoniae*, and 13 *K. variicola* isolates were downloaded from the SRA database (http://www.ncbi.nlm.nih.gov/Traces/sra/), and genome sequence data from 177 *K. pneumoniae*, 4 *K. quasipneumoniae*, and 11 *K. variicola* isolates were downloaded from the Assembly database (http://www.ncbi.nlm.nih.gov/assembly), and all passed filters for high quality; i.e., assemblies and SRA data aligned with ≥80% of MGH 78578 or ≥88% of the strict core genome multilocus sequence typing (scgMLST) references (described below), SRA data at a ≥10× read depth.

NASP (48), developed for microbial genome analysis, was used to detect SNPs among genomes. In brief, reads were aligned with a reference genome, either one concatenated from scgMLST alleles (10) or MGH 78578 (GenBank accession no. CP000647) with Novoalign V3.04.04 (Novocraft Technologies, Selangor, Malaysia) and SNPs were called with GATK version 2.7-2 (49). Data filtered out included SNP loci with <10× coverage or with <90% consensus in any one sample, regions duplicated in the reference genome as identified by Nucmer, and SNP loci that were not present in all of the genomes in the data set. In NASP, results were output in a SNP matrix from a core genome common to all of the isolates in the analysis. Phylogenetic trees were generated from the NASP SNP matrices with MEGA 6.0 (50) and subsequently plotted by means of ITOL v2 or v3 (51).

Genomic Target Identification

To find whole gene targets for assay design, selected genomes were assembled with UGAP, which uses the SPAdes genome assembler, version 3.6, for this work (52). Assemblies were then run through LS-BSR (53), which generates a list of open reading frames (ORFs) that have high identity among target species genomes and that have low identity or are not present in nontarget genomes. Alleles of the candidate target ORFs were collected by BLAST, including alleles from nontarget genomes, if present. Lastly, alleles of candidate ORFs were aligned for assay design. Canonical SNPs (canSNPs) were identified from the SNP matrix generated by NASP. Sequence flanking each SNP was collected from the NASP reference genome.

AMR and Virulence Gene Target Collection

AMR and virulence gene sequences were identified and collected in several ways, including from the *Klebsiella* BIGSdb, public literature, and the NCBI. Public literature included a paper by Holt et al. (54) in which a species-wide analysis of *K. pneumoniae* genomes revealed several siderophore systems and other virulence factors associated more with infectious than with colonizing strains. AMR genes included the major ESBL and carbapenemase genes and plasmid-mediated quinolone resistance determinants, as well as the gyrA and parC chromosomal genes, several aminoglycoside resistance genes, trimethoprim-sulfamethoxazole, tetracycline, streptomycin, chloramphenicol, and fosfomycin resistance genes, and the recently discovered plasmid-mediated colistin resistance gene mcr-1. Virulence targets included several siderophore systems, for which multiple genes from each were used as assay targets; the regulator of the mucoid phenotype (an indicator of hypervirulence); the wzi gene for capsule typing, for which we used the previously published assay (55); and two genes highly associated with invasive infection, pK2044_00025 and pK2044_00325 (54). For genes that consist of highly diverse alleles, for example, blaCTX-M, qnrB, or dfrA, phylogenetic trees based on nucleotide sequences were generated in order to group similar alleles for assay design.

Assay Design and Validation

Gene-based target alleles were aligned in SeqMan (DNAStar, Madison, WI) to identify conserved regions for primer design, and assays were designed with guidance from RealTimeDesign (Biosearch Technologies, Petaluma, CA), or gene-based assays were generated with AlleleID (Premier Biosoft, Palo Alto, CA), which designs assays to capture alleles in an alignment rather than individual sequences. SNP assay primers were designed with RealTimeDesign, and primer sequences were checked for conservation in the NASP SNP matrix. Lastly, assays were run through BLAST (http://blast.ncbi.nlm.nih.gov/Blast.cgi) to check for cross-reactivity with other relevant targets or species, including human. Universal tails were added to each primer sequence for library preparation as described below. The assays and their primer sequences are listed in Table 4.

Individual assays were screened across positive controls when they were accessible and screened across several isolate genomic DNAs (gDNAs) to test robustness. Additionally, multiplex PCR was validated by initial gene-specific PCR (described below), followed by PCR product dilution and then screening of individual assays by Sybr green-based quantitative PCR (qPCR). For this, 10-µl reaction mixtures of 1× Platinum SYBR green qPCR SuperMix (ThermoFisher Scientific, Waltham, MA), 200 nM forward and reverse primers of one assay, and 1 µl of diluted multiplex PCR product were run at 95° C. for initial denaturation for 4 min and then 40 cycles of 95° C. for 15 s and 60° C. for 1 min. Lastly, several panels of known isolate DNAs were screened by the amplicon sequencing method to test the sensitivity and specificity of the species and strain identification assays. AMR and virulence gene assays were validated by comparing amplicon sequencing results with WGS data.

Amplicon Library Preparation and Sequencing

Amplicon library preparation with universal tails was described in detail previously (56). Here, assays were combined into three assay pools for multiplex PCR (see Table 4), requiring three initial PCRs for each sample. The initial gene-specific PCR mixture comprised 12.5 µl of Kapa Multiplex PCR Mastermix (Kapa Biosystems, Wilmington, MA), 10 µl of primer mix (final concentration of 200 nM each), and 2.5 µl of template DNA from each sample and was denatured at 95° C. for 3 min; cycled 25 times at 95° C. for 15 s, 60° C. for 30 s, and 72° C. for 1 min 30 s; and subjected to a final extension at 72° C. for 1 min. The three multiplex PCR products from the same sample were combined, and PCR products were cleaned with 1× Agencourt AMPure XP beads (Beckman Coulter, Indianapolis, IN). A second PCR with the universal tail-specific primers added Illumina's sample-specific index and sequencing adapters. This PCR mixture comprised 12.5 µl of 2× Kapa HiFi HotStart Ready Mix (Kapa Biosystems), 400 nM each primer, and 1 to 10 µl of cleaned gene-specific PCR product and was denatured at 98° C. for 2 min; cycled 6 to 12 times at 98° C. for 30 s, 65° C. for 20 s, and 72° C. for 30 s; and subjected to a final extension at 72° C. for 30 s. Final PCR products were cleaned with 0.8× Agencourt AMPure XP beads (Beckman Coulter). Amplicon libraries from individual samples were quantified by qPCR with the Kapa Library Quantification kit (Kapa Biosystems). Samples were then pooled in equimolar concentrations for sequencing on the Illumina MiSeq platform with the 2×250 bp version 2 kit.

Analysis

Amplicon sequencing results were automatically analyzed with a newly developed amplicon sequencing analysis pipeline (ASAP) (45) that uses a JavaScript Object Notation (JSON) file customized to describe all of the assays in a multiplex. The information in the JSON file includes (i) a category for each assay (presence/absence, SNP, gene variant, or region of interest) that dictates how ASAP will report results and (ii) reference sequences for read mapping. In ASAP, amplicon sequence reads are first trimmed of adapter or readthrough sequences with Trimmomatic (57) and then mapped to the reference sequences with an aligner of choice. BAM alignment files are analyzed alongside the JSON file assay descriptions to determine the presence, percent identity, and breadth and depth of coverage of the reference and proportions of nucleotide polymorphisms for each amplicon. User-defined parameters for KlebSeq-prepared samples included the bowtie2 aligner (58) for all of the assays except for wzi, for which bwa (59) was chosen (because the reference sequence is shorter than the expected amplicon and reads need to be clipped to align [55]), and thresholds for determining results of screening included percent identities listed in Table 4, 80% breadth at 100× depth of coverage for isolate DNA, 80% at 20× (clinical specimens) or 10× (fecal specimens) depth, and a ≥10% proportion of polymorphism for informative SNP loci for complex-specimen DNA (meaning that at least 10% of the reads had to share a SNP state at a given locus for it to be reported). For WGS-prepared data, the parameters were bwa aligner (for clipping) and 80% breadth at 5× depth. The ASAP output includes an XML file containing details of the analysis of each assay target for each sample, which can be converted into a webpage interface by XSLT transformations. An example of a KlebSeq ASAP output for one sample is shown in FIG. 2. SeqMan NGEN (DNAStar, Madison, WI) and Tablet (60) were used to verify results.

Klebseq Validation

Figure 3:
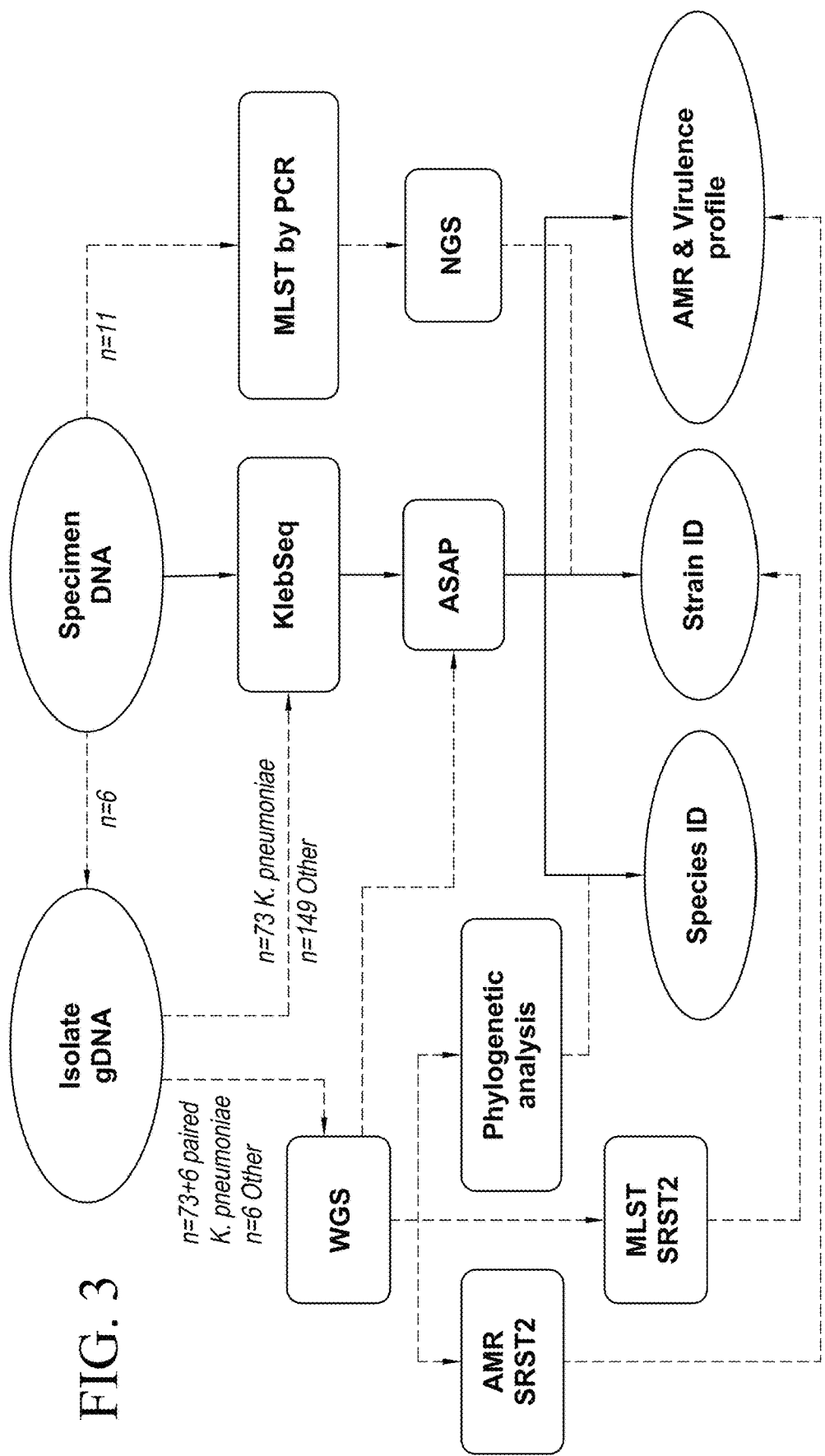
FIG. 3 depicts a workflow of the validation of KlebSeq. Dotted lines are methods used to confirm results from the workflow in solid lines (KlebSeq of specimen DNA). Strain identification validation was performed for 73 isolates plus 6 isolates that were cultured from KlebSeq-tested specimens (Tables 2 and 3). MLST PCR and sequencing were performed with 11 specimen DNA samples (Table 3). AMR gene detection validation is described in the text. NGS refers to next-generation sequencing.

FIG. 3 and the following text outline the processes used to validate KlebSeq, and Table 4 shows the extent to which each assay was validated in multiplex. First, WGS data from 73 *K. pneumoniae* samples were analyzed for AMR genes, subjected to MLST via SRST2 (61) and species identification confirmation via phylogenetic analysis, and also analyzed by ASAP. gDNA from these same 73 samples plus gDNA from 149 other species was screened with KlebSeq. To validate KlebSeq's *K. pneumoniae* strain identification and AMR gene profiles in specimens, six isolates that had been cultured and identified in six of the specimens were sequenced and analyzed. Additionally, a PCR for MLST was performed with selected specimen DNAs by the protocol from the *Klebsiella* BIGSdb. DNA libraries from the PCR products were prepared for sequencing by the same protocol as for whole gDNA. Sequence data were run through SRST2 to determine the ST of the *K. pneumoniae* present in the specimen.

Example 2. Phylogenetic Analysis and canSNP Identification

With the *Klebsiella* scgMLST (10) assembly as a reference, SNPs among a diverse set of genomes from *K. pneumoniae* and genomes from newly defined *K. quasipneumoniae* (22 from the public databases and 1 from in-house isolates) and *K. variicola* (24 from the public databases and 5 from in-house isolates) were identified with NASP. canSNPs that differentiate *K. quasipneumoniae* and *K. variicola* from *K. pneumoniae* were selected for assay development.

Figure 4:
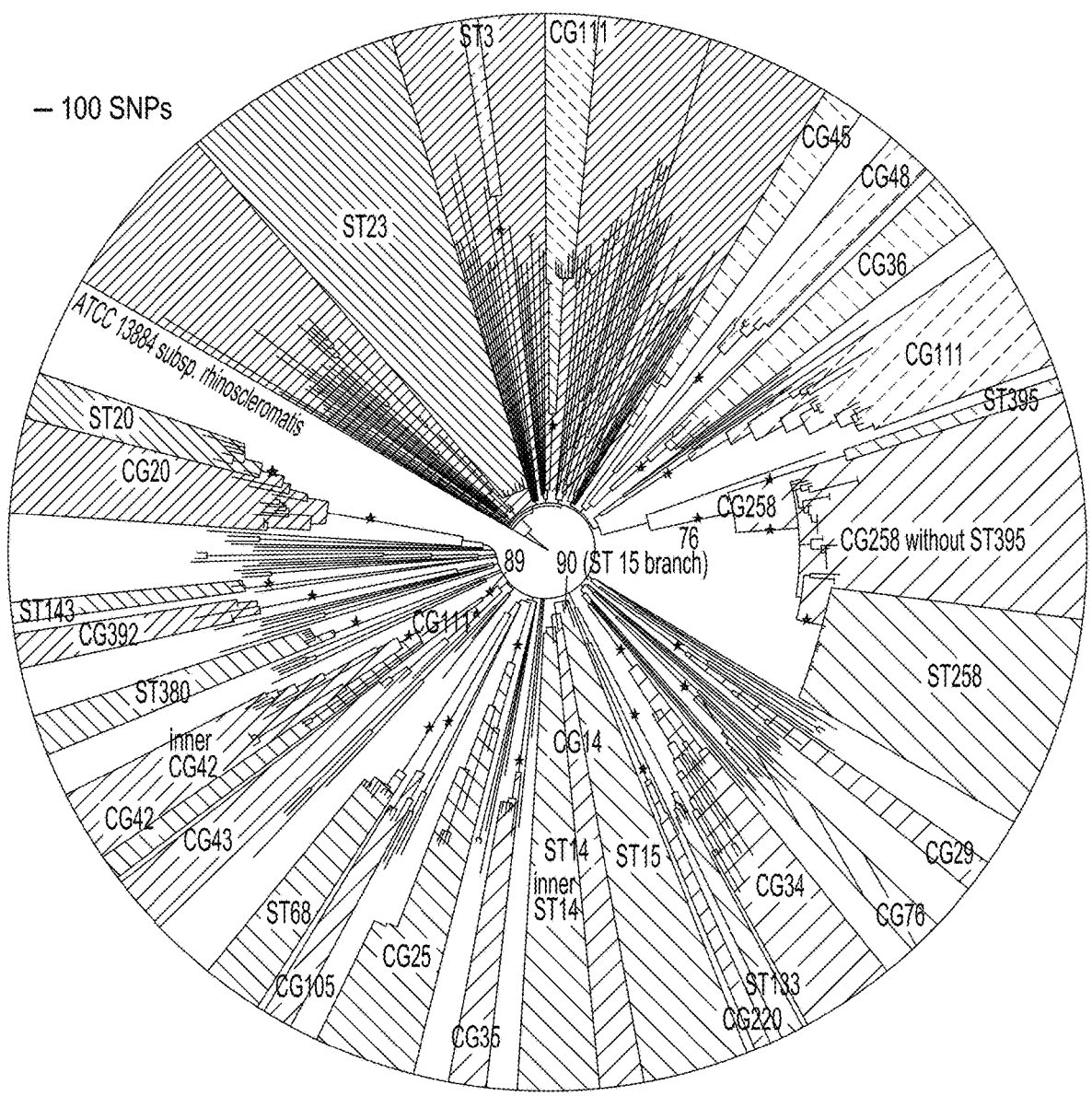
FIG. 4 depicts a maximum-parsimony tree with 100 bootstraps of the SNPs among 548 *K. pneumoniae* genomes. Major clonal groups are colored, and locations of canSNPs for strain identification assays are marked with stars. All of the branches labeled with canSNPs had >99% bootstrap support, except for the three branches indicated.

With the reference genome MGH 78578 and 547 diverse *K. pneumoniae* genomes, NASP generated a SNP matrix from which canSNPs for each of the major clonal groups were selected for assay development. Clonal groups and locations of canSNPs identifying 21 clonal groups and 12 STs in the context of the *K. pneumoniae* species are illustrated in FIG. 4. Redundancy was intentionally included in identifying canSNPs for the most epidemic strains of *K. pneumoniae*, such as ST14, ST20, and strains in CG258, in order to increase sensitivity and confidence in positive results.

Example 3. Assay Development

The identification of genomic targets, canSNPs, and AMR and virulence genes and subsequent assay design resulted in two assays specific to *K. pneumoniae* (Kp-M1 and Kp-M2), one each for *K. oxytoca* (Koxy_UT), *K. variicola* (Kvari_UT), and *K. quasipneumoniae* (Kquasi_UT), 37 assays to identify clonal groups or lineages within clonal groups of *K. pneumoniae*, 76 AMR gene assays, and 15 virulence gene assays (see Table 4). The canSNP states for each strain identification assay are specific to that clonal group of *K. pneumoniae*, except in the case of CG35, where the amplicon must match the reference sequence 98%, allowing up to four additional SNPs, in order to be called CG35. Otherwise, identity thresholds for each strain identification assay are optional; they merely make the assays completely *Klebsiella* specific, regardless of the canSNP state.

Example 4. KlebSeq Validation on Isolate DNA

Figure 5:
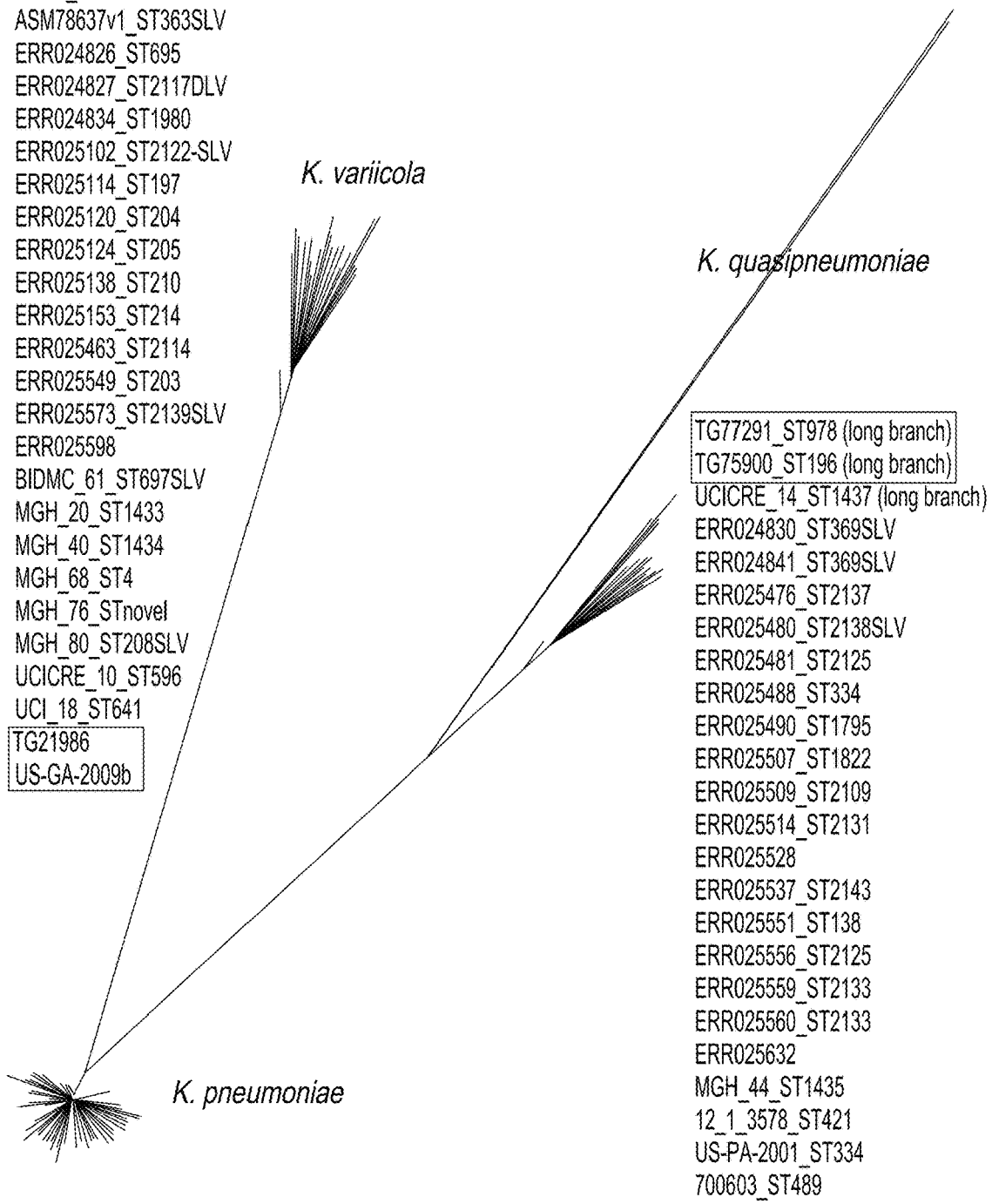
FIG. 5 depicts a neighbor-joining tree with 100 bootstraps of the SNPs in the diverse set of *K. pneumoniae, K. variicola,* and *K. quasipneumoniae* genomes used in this study. Unknown isolates that were identified as *K. variicola* and *K. quasipneumoniae* are boxed.

To validate the species and clonal group identification assays, gDNA from 73 *K. pneumoniae* isolates whose whole genomes were sequenced (4 of which were later identified as *K. quasipneumoniae* and *K. variicola* [see below]), 22 *K. oxytoca* isolates, and 157 other enteric opportunistic pathogen isolates, which included *E. coli*, *Enterobacter aerogenes*, *E. amnigenus*, *E. cloacae*, *E. hormaechei*, *Enterococcus faecalis*, *E. faecium*, an unknown *Enterococcus* species, *Proteus mirabilis*, *Providencia stuartii*, and *Serratia marcescens*, and 1 *Acinetobacter baumannii* isolate, were screened with KlebSeq. Sensitivity and specificity results of the species identification assays compared with clinical microbiological identification (Vitek 2) are in Table 1. With the redundancy built into the multiplex by including two assays, Kp-M1 and Kp-M2, that target two different *K. pneumoniae* species-specific genes (M1 and M2), 100% sensitivity is achieved. One isolate previously identified as *K. pneumoniae* was identified as *K. quasipneumoniae*, and two were identified as *K. variicola*. These isolates' whole genomes were added to the phylogenetic analysis of these three species that was previously run to find the species-specific canSNPs (see Materials and Methods). The *K. quasipneumoniae* and *K. variicola* genomes identified by our assay clustered with their respective species in the phylogeny (FIG. 5). Clinical methods do not currently distinguish among all three of these species, so assay sensitivity and specificity were not calculated for *K. quasipneumoniae* and *K. variicola* (Table 1).

TABLE 1

Results of KlebSeq species identification assays of genomic DNA from isolates whose whole genomes were also sequenced, DNA from specimens for which clinical culture results are known, and DNA from specimens with unknown content.

| DNA type (no. of samples) and species identified by clinical methods or parameter[a] | Total no. screened | No. of isolates identified by amplicon sequencing assay[b] | | | | | |
|---|---|---|---|---|---|---|---|
| | | Kp-M1 | Kp-M2 | Kp-M1 + Kp-M2 | Kquasi_UT | Kvari_UT | Koxy_UT |
| Isolate DNA (252) | | | | | | | |
| K. pneumoniae | 69 | 68 | 67 | 69 | 0 | 0 | 0 |
| K. quasipneumoniae | 2 | 0 | 0 | 0 | 2 | 0 | 0 |
| K. variicola | 2 | 2 | 0 | 2 | 0 | 2 | 0 |
| K. oxytoca | 14 | 0 | 0 | 0 | 0 | 0 | 14 |
| Nontarget species | 149 | February-88 | 0/88 | February-88 | 0/155 | 0/155 | 0/135 |
| % Sensitivity | | 99 | 97 | 100 | 100 | 100 | 100 |
| % Specificity | | 98 | 100 | 98 | 100 | 100 | 100 |
| Urine DNA (46) | | | | | | | |
| K. pneumoniae | 16 | 14 | 15 | 16 | 2 (1 mix)[c] | 1 (mix)[c] | 0 |
| K. oxytoca | 6 | 1 | 1 | 1 (CG34) | 0 | 0 | 6 |
| Other species | 24 | 1 | 1 | 1 | 0 | 0 | 0 |
| Unknown | 0 | 0 | 0 | 0 | 0 | 0 | 0 |
| % Sensitivity | | 88 | 94 | 100 | | | 100 |
| % Specificity | | 90 | 93 | 93 | | | 100 |
| Wound DNA (40) | | | | | | | |
| K. pneumoniae | 1 | 0 | 0 | 0 | 0 | 1 | 0 |
| K. oxytoca | 1 | 0 | 0 | 0 | 0 | 0 | 1 |
| Other species | 31 | 0 | 0 | 0 | 0 | 0 | 0 |
| Unknown | 7 | 1 | 1 | 1 (CG29) | 0 | 0 | 1 |
| % Sensitivity | | 0 | 0 | 0 | | | 100 |
| % Specificity | | 100 | 100 | 100 | | | 100 |
| Respiratory specimen DNA (87) | | | | | | | |
| K. pneumoniae | 6 | 6 | 6 | 6 | 0 | 0 | 0 |
| K. oxytoca | 1 | 0 | 0 | 0 | 0 | 0 | 1 |
| Other species | 77 | 7 (1 ST258) | 5 | 7 (2 CG36, 1 CG37) | 0 | 0 | 1 |
| Unknown | 3 | 0 | 0 | 0 | 0 | 0 | 0 |
| % Sensitivity | | 100 | 100 | 100 | | | 100 |
| % Specificity | | 91 | 94 | 91 | | | 99 |
| Fecal specimen DNA (89) | 89 | 9 | 5 | 9 | 1 (mix)[c] | 3 (2 mix)[c] | 13 |
| All specimens (isolates not included) (262) | | | | | | | |
| K. pneumoniae | 23 | 20 | 21 | 22 | 2 | 2 | 0 |
| K. oxytoca | 8 | 1 | 1 | 1 | 0 | 0 | 8 |
| Other species | 132 | 8 | 6 | 8 | 0 | 0 | 1 |
| Unknown | 99 | 10 | 6 | 10 | 1 | 3 | 14 |
| % Sensitivity | | 87 | 91 | 96 | | | 100 |
| % Specificity | | 94 | 95 | 94 | | | 99 |

[a]K. quasipneumoniae is not distinguished from K. pneumoniae by the clinical identification method used (Vitek 2).
[b]Kp-M1 and Kp-M2 are K. pneumoniae species identification assays that detect targets M1 and M2 in the K. pneumoniae genome. Kquasi_UT, Kvari_UT, and Koxy_UT are K. quasipneumoniae-, K. variicola-, and K. oxytoca-specific assays, respectively.
[c]These species were found as mixtures with K. pneumoniae on the basis of a proportion (≥10%) of the sequencing reads containing the species-defining SNP.

Table 2 shows the KlebSeq results of the K. pneumoniae clonal group identification and capsule typing assays of isolate DNA. Each isolate's strain type was correctly captured by the appropriate assays or not captured in cases where no assay was designed for that clonal group. Included in Table 2 are results from partial sequencing of the wzi gene for capsule typing. This gave surprisingly clear results, given that approximately 75 bp of the informative region are missing from our sequence output, as the PCR amplicon is approximately 580 bp (55), which is too long to cover with the Illumina version 2 sequencing chemistry. However, full capsule typing by wzi sequencing would be possible with longer-read chemistry (i.e., Illumina version 3 chemistry, for 600-bp reads). Results from screening of nontarget organisms showed that several of the K. pneumoniae clonal group assays amplified DNA from other organisms, as expected. An identity threshold can be applied (see Table 4); however, all of the SNP states that define a particular clonal group are specific to that clonal group, except for CG35, so the identity threshold is optional except for this assay. Sequence analysis by ASAP reports when a clonal group is present only if the defining canSNP state is present and reports nothing if it is not.

TABLE 2

Isolates used for assay validation and results of strain typing by amplicon sequencing[a]

| Isolate ST | No. of isolates | ASAP strain typing assay result(s) | Capsule typing result(s) by partial wzi sequencing[b] |
|---|---|---|---|
| ST11 | 3 | CG258, CG258 without 395 | wzi-39 or -75, wzi-74, not typeable |
| ST14 | 5 | CG14, ST14, inner ST14 | All wzi-2 |

TABLE 2-continued

Isolates used for assay validation and results of strain typing by amplicon sequencing[a]

| Isolate ST | No. of isolates | ASAP strain typing assay result(s) | Capsule typing result(s) by partial wzi sequencing[b] |
|---|---|---|---|
| ST14 SLV[d] | 1 | CG14 | wzi-16 |
| ST15 | 2 | CG14, ST15 | All wzi-24 or -45 |
| ST20 | 2 | CG20, ST20 | wzi-84, wzi-118 |
| ST23 | 8 | ST23 | wzi-1 |
| ST34, ST34 SLV | 2 | CG34 | wzi-114, wzi-12 |
| ST36 | 2 | CG36 | All wzi-27 or -79 |
| ST37 | 2 | CG37 | wzi-50, wzi-39 or -75 |
| ST39 | 1 | No group | wzi-2 |
| ST42 | 2 | CG42, inner CG42 | All wzi-29 |
| ST43 | 1 | CG43 | wzi-30 |
| ST45 | 1 | CG45 | wzi-133 |
| ST65 | 1 | CG25 | wzi-72 |
| ST101 | 2 | CG43 | wzi-29, wzi-137 |
| ST107 | 1 | No group | wzi-74 |
| ST111 | 1 | CG111 | wzi-63 |
| ST147 | 1 | CG392 | wzi-64 |
| ST152 | 1 | CG105 | wzi-150 |
| ST228 | 1 | CG34 | wzi-116c |
| ST234 | 1 | No group | wzi-114 |
| ST249 | 2 | No group | All wzi-128 |
| ST258, no clade | 6 | CG258, CG258 without ST395, ST258 | All wzi-154 |
| ST258, clade 1 | 3 | CG258, CG258 without ST395, ST258, clade 1 | All wzi-29 |
| ST258, clade 2 | 2 | CG258, CG258 without ST395, ST258, clade 2 | All wzi-154 |
| ST277 | 1 | No group | wzi-97 or -185 |
| ST334 | 1 | K. quasipneumoniae | wzi-68 |
| ST340 | 2 | CG258, CG258 without ST395, ST340 | wzi-50, wzi-173 |
| ST376 | 1 | CG42, inner CG42 | wzi-2 |
| ST380 | 1 | ST380 | wzi-203 |
| ST437 | 1 | CG258, CG258 without 395, ST437 | wzi-109 |
| ST636 | 1 | No group | wzi-155 |
| ST719 | 1 | No group | wzi-192 |
| ST776 | 1 | No group | wzi-39[c] or -75[c] or -193[c] |
| ST833 | 1 | CG258, CG258 without 395 | wzi-50 |
| ST978 | 1 | K. quasipneumoniae | wzi-212[c] |
| ST1401 | 1 | No group | wzi-96 |
| ST82 | 2 | No group | All wzi-128 |
| ST260 | 1 | No group | wzi-1 |
| ST360 SLV | 1 | K. variicola | wzi-53 |
| ST427 SLV | 1 | No group | wzi-64 |
| ST513 SLV | 1 | No group | wzi-87 |
| ST815 SLV | 1 | No group | wzi-114[c] |
| ST244 SLV | 1 | No group | wzi-162[c] |
| ST2006 | 1 | K. variicola | wzi-227 |
| ST2055 | 1 | No group | wzi-14 |

[a]Table 5 lists the genome accession numbers of the isolates.
[b]The Illumina version 2 chemistry used provides approximately 500 bp of sequence data. The amplicon size for the wzi assay is approximately 580 bp (55).
[c]The wzi allele represents the best match; one or more SNPs were present.
[d]SLV, single-locus variant.

AMR gene detection by amplicon sequencing was validated by comparing ASAP results with AMR gene screening of WGS with SRST2 (61) and with ASAP. Results showed an almost perfect correlation between KlebSeq ASAP and WGS ASAP, indicating that the KlebSeq PCRs are performing well. There were a few discrepancies with SRST2, which reported uncertainty (SNPs or low-coverage indicators) for most of the discrepancies. Some discrepancies were in the presence of the dfrA gene. This group of genes is very diverse, so it may be that KlebSeq does not capture the full repertoire of dfrA genes. Virulence gene detection was validated by comparing ASAP results from WGS data with those from amplicon sequence data, and results showed concordance. In addition, by targeting multiple genes that are part of the same virulence factors (i.e., siderophore systems), sensitivity and confidence in results were increased.

These results also confirm that KlebSeq is applicable to pure isolates as well as complex specimens. Screening of isolate DNA has the added benefit of traceability of the AMR and virulence genes, which are often carried on mobile genetic elements, to their host. Isolate screening could be used for surveillance and other purposes for identifying or characterizing Klebsiella.

Example 5. Specimen Sample Results

KlebSeq was run on DNA from 87 respiratory specimens, 46 urine specimens, 40 wound specimens, and 89 fecal samples from healthy. Sensitivity and specificity results of the species identification assays compared with those of clinical microbiological methods are shown in Table 1. In most cases, sensitivity was high, except in the wound specimens, where the one sample clinically identified as K. pneumoniae was identified as K. variicola. Some sensitivity and specificity calculations may be misleadingly low, as amplicon sequencing identified some samples as containing K. pneumoniae that actually contained K. quasipneumoniae or K. variicola, and several as containing Klebsiella that went undetected by clinical microbiological methods, including several in which clonal groups were also detected. In the healthy donor specimens, K. oxytoca (n=13) was more prevalent than K. pneumoniae (n=9). Sequencing read depth was low in some samples; this may have been due to dilution of the DNA samples before screening, as each was diluted 1:10 in water.

Important Klebsiella clonal groups were detected in multiple specimens. In the 17 urine samples positive for K. pneumoniae, clonal identifications included CG34, ST20, CG45, CG392 (which includes the NDM producer ST147 [62], though this sample was negative for blaNDM), ST133, and CG111. In wounds, the only sample K. pneumoniae positive by KlebSeq was CG29. From respiratory specimens, groups CG37 (n=2), ST134 (n=1), ST258 (n=2), CG36 (n=3), and inner ST14 (n=1) were identified. Interestingly, several clonal groups were identified in the healthy donor fecal specimens as well. In the nine K. pneumoniae-positive samples, the groups included ST20, CG37, and CG76, which are all members of multidrug-resistant outbreak strain types (11, 12, 15), along with ST133 and ST380. ST380 is associated with a K2 capsule type and hypervirulence and causes pyogenic liver abscesses in healthy people, especially those of Asian ethnicity (63). Many Asians are colonized by hypervirulent K1 or K2 capsule strain types; however, the level of risk of subsequent liver infection is unknown (63). For this sample, no wzi gene sequence was obtained; thus, the capsule type is unknown. A majority of the K. pneumoniae isolates in our samples did not fall into the major clonal groups targeted by KlebSeq. These strains probably all belong to lesser-known clonal groups, as more studies are showing that many K. pneumoniae infections are caused by nonepidemic, sporadic strains (64, 65).

Numerous and variable AMR genes were detected in the specimens, including different variants of the same gene that confer different phenotypes. With sequence-based information, we demonstrate that seven of the *K. pneumoniae* had key mutations in the gyrA gene known to confer resistance to fluoroquinolones. Additionally, several samples contained the aac(6')-Ib gene for aminoglycoside resistance, and five of those contained the sequence variant aac(6')-Ib-cr for fluoroquinolone resistance; mixtures of these two genes were also detected. Many of the infection specimens (non-healthy donor specimens), both positive and negative for *K. pneumoniae*, were positive for other aminoglycoside resistance genes, as well as tetracycline, trimethoprim-sulfamethoxazole, streptomycin, fosfomycin, and chloramphenicol resistance genes. A few contained plasmid-mediated quinolone resistance genes. Several samples, especially the respiratory specimens, were also positive for KPC and CTX-M group 1 and 9 genes. Most of the healthy donor specimens were positive for trimethoprim-sulfamethoxazole resistance genes, and many were positive for streptomycin, aminoglycoside, tetracycline, and fosfomycin resistance genes. Interestingly, 39 of the 89 were positive for npmA, a relatively recently described pan-aminoglycoside resistance gene (66). These specimens were the only samples positive for this gene. Three specimens contained plasmid-mediated quinolone resistance genes. Fortunately, none were found to contain ESBL or carbapenemase genes. No complex specimens in this study were positive for genes encoding the important carbapenemases OXA-48, VIM, and NDM, and none were positive for the plasmid-mediated colistin resistance gene mcr-1.

These sets of samples did not appear to contain especially virulent strains of *K. pneumoniae*. The yersiniabactin siderophore genes were, by far, the most prevalent of the virulence genes tested, although positive samples made up less than half of the *K. pneumoniae*-positive samples. No specimens were positive for rmpA, the regulator of mucoid phenotype gene, including the ST380-containing sample, and few were positive for the salmochelin siderophore genes, which are associated with invasive *K. pneumoniae* infection (54). One respiratory specimen that contained an ST14 strain was positive for a K2 capsule type by partial wzi sequencing. K2 strains of *K. pneumoniae* are associated with hypermucoviscosity and hypervirulence, as previously mentioned. However, this respiratory sample was not positive for rmpA, and a recent study proposed that the presence of multiple siderophore system genes (linked to K1 or K2 capsule genes) explains hypervirulence rather than capsule type (54). In our data, *K. pneumoniae*-containing samples were positive for multiple siderophores or other virulence-associated genes only 15% of the time. Sequencing of wzi revealed a variety of capsule types and cases in which the same clonal groups had different wzi genotypes and in which they had the same genotype. This character would help identify or rule out a transmission event when patients carrying the same strain are found.

On an interesting note, in the healthy donor fecal samples collected from members of the same families over time, out of the nine *K. pneumoniae*-positive samples, only two came from the same person over time. The characterization assays suggest that the same strain of *K. pneumoniae* was present at both time points. *K. pneumoniae*-positive samples were found in multiple members of two of the seven families. In one of these families, the positive members carried strains different from one another, and in the other, it appears that two members had CG37 isolates with the same capsule type. The sample set is too small to draw conclusions from these data; however, the data raise interesting questions about community *K. pneumoniae* carriage.

Example 6. Validation of KlebSeq Strain Identification in Specimens

Table 3 shows MLST results from WGS data of six isolates cultured from specimens run on KlebSeq and from MLST PCR and sequencing of 11 specimens run on KlebSeq. In each case, KlebSeq appears to have identified the correct strain. Two isolates for which no strain type was identified by KlebSeq have novel STs. Sample TG75900 was identified as *K. quasipneumoniae* by KlebSeq and typed as ST196 on the basis of whole-genome data. This genome was added to the phylogeny of the three species and clustered with *K. quasipneumoniae* (FIG. 5). MLST of the specimen DNA did not yield results for all of the MLST loci of all 11 samples, which is to be expected given the complexity of the specimen DNA sample. In cases where only partial data were retrieved, at least three alleles from each match the strain identified by KlebSeq.

TABLE 3

Results of KlebSeq strain identification validation by MLST of isolates cultured from specimens tested by KlebSeq and MLST of specimens tested by KlebSeq

| Sample | Type | KlebSeq identification of original specimen | No. of loci retrieved from sequence data | ST by MLST |
|---|---|---|---|---|
| TG69923 | Isolate | CG29 | 7 | Novel; DLV[a] of ST29 |
| TG75899 | Isolate | CG392 | 7 | ST392 |
| TG75900 | Isolate | *K. quasipneumoniae* | 7 | ST196 |
| TG75901 | Isolate | ST133 | 7 | Novel; SLV[b] of ST133 |
| TG75902 | Isolate | No strain ID | 7 | Novel; DLV of ST248 |
| TG75911 | Isolate | Mixture of *K. pneumoniae* with no strain ID and *K. variicola* | 7 | Novel; TLV[c] of ST633 |
| TG69737 | Urine | CG34 | 7 | Novel; 4 alleles match ST34 |
| TG69766 | Urine | CG45 | 6 | 6 alleles match ST45 |
| TG69776 | Urine | CG111 | 7 | Novel; DLV of ST111 |
| TG69861 | Respiratory | No strain ID | 7 | Novel; SLV of ST393 |
| TG69865 | Respiratory | ST134 | 6 | 5 alleles match ST134 |
| TG69871 | Respiratory | CG37 | 3 | 3 alleles match ST37 |
| TG69883 | Respiratory | ST258 | 7 | Novel; 3 alleles match ST258 |
| TG73885 | Respiratory | CG36 | 7 | Novel; 3 alleles match ST36 |
| TG73911 | Respiratory | Mixture of *K. pneumoniae* with no strain ID and CG36 | 6 | 4 alleles match ST36 |
| TG73916 | Respiratory | Inner ST14 | 7 | Novel; 4 alleles match ST14 |

TABLE 3-continued

Results of KlebSeq strain identification validation by
MLST of isolates cultured from specimens tested by
KlebSeq and MLST of specimens tested by KlebSeq

| Sample | Type | KlebSeq identification of original specimen | No. of loci retrieved from sequence data | ST by MLST |
|---|---|---|---|---|
| TG74003 | Respiratory | Mixture of K. pneumoniae no strain ID and CG36 | 7 | Novel; DLV of ST461 |

[a]DLV, double-locus variant.
[b]SLV, single-locus variant.
[c]TLV, triple-locus variant.

In the United States, HAI is estimated to affect 1 in 25 hospital patients, totaling hundreds of thousands of patients, with significant mortality (2). HAIs have a significant impact on health care costs; a 2009 CDC report estimated upwards of $45 billion in annual additional cost (67). Infections with AMR organisms cause significantly higher mortality rates, significantly more intensive care unit (ICU) admissions, and significant excess costs, including hospitalization, medical care, and antimicrobial therapy, than do infections with susceptible strains (5, 68). HAI prevention measures, although costly in and of themselves (69), have the potential to save thousands of lives and billions of dollars (67). Periodic patient screening and isolation of AMR organism carriers have proven successful in controlling transmission and outbreaks in several hospitals (31, 34-37). Use of a highly informative screening and surveillance tool such as KlebSeq has cost-effective and life-saving potential.

Early detection of colonization of health care patients by K. pneumoniae, especially multidrug-resistant K. pneumoniae, would allow health care staff to make more informed patient management decisions. In outbreak situations, rapid identification of transmissions before subsequent infections would allow for proactive measures to curb an outbreak. In nonoutbreak situations, identification of particular strains and AMR genes would help to assess the risk of K. pneumoniae carriage to the host patient, as well as to other patients, as some strains are more closely associated with adverse outcomes (e.g., outbreaks, HAI, AMR, and treatment failure) than others (7-13, 70). Although our understanding of many Klebsiella virulence factors is limited, identification of virulence genes gains us understanding of the correlations between particular virulence factors and the risk of disease (54). Additionally, many K. pneumoniae infections, including HAIs and non-multidrug-resistant infections, are caused by nonepidemic, lesser-known strain types (64, 65). Classifying the K. pneumoniae isolate in each patient sample would help an institution to decide when and which intervention procedures should be enacted and also to understand more about transmission dynamics and local strain type circulation.

KlebSeq has several characteristics that make it attractive as a health care screening approach. With a single assay, enough information is garnered about a patient's Klebsiella carriage status to contribute greatly to patient management and to infection control decisions. Indexing samples by means of the universal tail during sample preparation allows the characterization of a large number of specimens in one run, minimizing sequencing costs per specimen and allowing for high-throughput screening of hundreds of patient samples simultaneously at a cost of tens of dollars per patient. KlebSeq uses DNA extracted directly from a specimen, so targets from entire populations of a species are analyzed to capture different strains in the same sample, which can be numerous (71, 72). If culture-based methods are used for screening, different strains are missed when one genotype (i.e., colony) is chosen for characterization, and the resulting information is limited. Additionally, culture-based methods can miss "silent" multidrug-resistant K. pneumoniae strains that test negative for carbapenemases in vitro (16), and if used for high-throughput screening, they can be laborious, time-consuming, costly, and subjective (31, 38). If screening of large numbers of patients by amplicon sequencing is cost-prohibitive, it can be limited to the highest-risk groups of patients, i.e., long-term care facility patients (31, 73), travelers returning from regions where Klebsiella carriage is endemic (74, 75), ICU patients (28), patients with previous K. pneumoniae carriage (75-77), patients who have shared a room with a known carrier (78) or case contacts of carriers (79), those who have recently taken antibiotics (80, 81), or patients on mechanical ventilation or enteral feeds or who have had prior Clostridium difficile infections (82). Additionally, using ASAP makes the analysis in KlebSeq streamlined and results are easily interpretable. Lastly, the amplicon sequencing and ASAP package is customizable and updateable (45). Individual assays can be added or removed, adding only the cost of new primers.

The results we present here show that KlebSeq is effective with DNA from numerous sample types, including pure organism culture, or complex, multiorganism samples and swab samples with low-level microbial DNA in a presumably high human DNA background without culture methods. In addition to clinically important clonal lineages of K. pneumoniae, KlebSeq also reliably distinguishes among the Klebsiella species, two of which, K. quasipneumoniae and K. variicola, are continuously misidentified as K. pneumoniae (as exemplified in our study) and cause invasive disease (83, 84). Additionally, we highlight several instances where culture methods failed to produce a positive K. pneumoniae result, including one sample that contained the critical ST258 strain. The sensitivity of KlebSeq is superior to that of culture-based methods for complex specimens, lowering the risk of false negatives in patient screening. We identified dozens of AMR and virulence genes within individual samples, demonstrating the additional function of profiling for clinically important characteristics, and were able to distinguish minor genotype differences that confer different phenotypes, such as the gyrA gene, aac(6')-Ib versus aac(6')-Ib-cr, and the wzi gene.

Notably, our data show that healthy individuals may carry clinically important strains of K. pneumoniae and frequently K. oxytoca, as well as many AMR genes and siderophore virulence systems. For our purposes, these healthy donor fecal DNA samples were used to validate the use of our amplicon sequencing approach with highly complex fecal metagenome samples. Much more study is needed to elucidate the implications of healthy host carriage of known pathogenic strains of K. pneumoniae and their virulence factors. Furthermore, the fact that we observed carriage of the hypervirulence-associated ST380 strain from a healthy person and the hypervirulence-associated K2 capsule type in an ST14 strain from a respiratory infection lends credence to the idea that we need much more information about K. pneumoniae carriage strains to be able to draw conclusions about these associations. Aside from these important observations, other observations from these data raise questions about the dynamics of K. pneumoniae carriage and microbiome sharing. The fact that there were not more cases of positive results from the same person at multiple rather than single time points is interesting. This could be due to intermittent shedding of *K. pneumoniae* in feces, intermittent colonization by *K. pneumoniae*, or heterogeneity in the sample itself, underrepresenting the full microbial community when a small sample is taken; this observation further warrants periodic rather than one-time screening of patients at risk. Of the two instances where two family members carried *K. pneumoniae*, each tells a different story about microbiome sharing. An amplicon sequencing-based diagnostic approach would facilitate longitudinal patient screening because of ease of use and limited costs.

Among the many pathogens encountered in health care institutions, we focus only on *Klebsiella* because of its high priority in public health and the high risk of CPE establishment in a facility. Additionally, although many other HAI agents cause devastating and costly infections, directing a complex assay such as KlebSeq at a subset of those agents greatly simplifies the validation process and speeds the availability of assay results (especially in the case of validation for FDA approval [85]). KlebSeq is an important step toward a comprehensive yet accessible tool for all pathogen identification and characterization. Metagenomic analysis is attractive in its breadth of coverage capabilities, but its current costs and complexities are prohibitive. Amplicon assays targeting the other ESKAPE (*Enterococcus faecium, Staphylococcus aureus, Klebsiella pneumoniae, Acinetobacter baumannii, Pseudomonas aeruginosa*, and *Enterobacter* species) pathogens and more AMR determinants could relatively easily be added to the tool described here, with a step-by-step validation process. We have not found the limit of the multiplexing capacity. (We run three multiplexed PCRs merely because the PCR volume limits the number of primers that can be added; future assays will utilize primers at a higher concentration to test the multiplexing limit.) The multiplexing limit is also presumably dependent on the number and sizes of targets that are present in a sample, potentially exhausting the polymerase or sequencing space. These pieces are unpredictable for specimens of unknown content. Lastly, our report serves as evidence in favor of the concept that highly multiplexed amplicon sequencing is one good answer to the call for early detection tools in infection control.

KlebSeq is designed for screening and periodic surveillance in high-risk situations with a rule-in/rule-out determination of the possibility of transmission events and through identification of high-risk multidrug-resistant or epidemic strains of *Klebsiella*. For these purposes, KlebSeq is ideal. The specimen types used for validation could be considered a limitation, as we did not test rectal swabs, a specimen type commonly used for CPE surveillance. However, we show that KlebSeq works with different swab types and fecal specimens, which addresses the challenges of detection in rectal swabs. The turnaround time from sample collection to result is dependent only on current technology (not organism culture), and we recently conducted a proof-of-concept study of a 24-h sample-to-answer test with different targets (data not shown). This test was done on an Illumina MiSeq with only 60 cycles. Other platforms and upcoming technology may allow this turnaround time to be decreased even further.

Rapid amplicon sequencing with automated analysis and reporting is a promising response to the need for constant surveillance for highly transmissible or highly drug-resistant pathogens. Our model system, directed at *Klebsiella*, can easily be adapted to multiple other pathogens and to different purposes, such as environmental sampling and community host screening and, as smaller, more on-demand next-generation systems become available, to diagnostics and individual patient monitoring. The targeted, highly multiplexed nature of amplicon sequencing and the ability to interpret the data instantly make it an applicable tool for health care facility surveillance. As these technologies are adopted, considerable coordination within the health care facility is paramount to the success of infection and outbreak prevention, with the integration of isolation and barrier precautions, excellent communication, and good stewardship. Nevertheless, several institutions have shown that the combination of surveillance and systematic response reduces outbreaks and multidrug-resistant infections (31, 33-37).

TABLE 4

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| Species Identification Assays | | | | | | | | | |
| Kp-M1_UT | presence/absence | Kp_M1_UT1_F<br>Kp_M1_UT1_R | CGTTCCTCAC CGTAGTCG<br>TCCAGCGACAT AATCGG | 1<br>2 | 321 | See Table 1 | | 97% (10) | 1 |
| Kp-M2_UT | presence/absence | Kp_M2_UT1_F<br>Kp_M2_UT1_R | TGCCTATCGCCACT TTATTGA<br>CGGTCGTTAATCGC CTTCT | 3<br>4 | 366 | See Table 1 | | 94% (20) to include identification of K. varicola and K. quasipneumoniae | 1 |
| Koxy_UT | presence/absence | Koxy_UT_F<br>Koxy_UT_R | CCGTCGCCGTATTA CTGAT<br>TCTCTACAACACGC TACCCTA | 5<br>6 | 362 | See Table 1 | | 97% (15) | 1 |
| Kvari_UT | SNP (T43 to G, T67 to C, C91 to T, G126 to A, G143 to T, T181 to C, G184 to T, A220 to G, A235 to G) | Kvari_UT_F<br>Kvari_UT_R | TCAGCTATCGCCTG GAGTGCTA<br>CTGCTCCTGCCGA CAAAC | 7<br>8 | 287 | See Table 4, FIG 3 | | 91% (26) | 3 |
| Kquasi_UT | SNP (A39 to G, A51 to G, G63 to A, A78 to C, G82 to C, T147 to C) | Kquasi_UT_F<br>Kquasi_UT_R | GCCATAATGCAGC CTTTGC<br>ATCCGCTGAACGT CAGCTTCT | 9<br>10 | 187 | See Table 4, FIG 3 | | 92% (15) | 3 |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| Clonal Group Identification Assays | | | | | | | | | |
| ST3_UT | SNP (C25 to T) | ST3_UT_F<br>ST3_UT_R | GCAGCCGTACAGA CCGA<br>CYATTCGCCAGCA GGACTA | 11<br>12 | 237 | Sequence type not available | KlebSeq on non-ST3 K. pneumoniae | 98% (5); also identifies K. variicola and K. quasi-pneumoniae | 3 |
| CG14_UT | SNP (G42 to A) | CG14_UT_F<br>CG14_UT_R | GGGATCGASTTCAC GTCCAC<br>ACGCCGAGGGACA RGAGM | 13<br>14 | 271 | See Table 4 | | 94% (17) | 3 |
| ST14_UT | SNP (T33 to A) | ST14_UT_F<br>ST14_UT_R | GCAGATTTAACCG AGCTGGTCT<br>AGAGCGATGGCGA AGAGA | 15<br>16 | 205 | See Table 4 | | 98% (5) | 3 |
| innerST14_UT | SNP (G37 to A) | innerST14_UT_F<br>innerST14_UT_R | CGACAACCGCTTC GCTACC<br>AGYACCGGGCGCA GATTG | 17<br>18 | 273 | See Table 4 | | 96.5% (10) | 3 |
| ST15_UT | SNP (C26 to T) | ST15_UT_F<br>ST15_UT_R | GMACGCCGACGTC ATYCT<br>CAGTGCTTGCATA GTGTCCTCTT | 19<br>20 | 271 | See Table 4 | | 93.5% (18) | 3 |
| CG20_UT | SNP (T37 to C) | CG20_UT_F<br>CG20_UT_R | CGGTCGTGTTTGTC TGAACG<br>CAGGTGCGGATCT TGTCAATG | 21<br>22 | 144 | See Table 4 | | 98% (3) | 3 |
| ST20_UT | SNP (G35 to A) | ST20_UT_F<br>ST20_UT_R | TCTTTGATCTTGTC CGGGTTGA<br>CCTCGGCGATATG GACTTCA | 23<br>24 | 240 | See Table 4 | | 98% (5); also identifies K. variicola and K. quasipneumoniae | 3 |
| ST23_UT | SNP (T36 to A) | ST23_UT_F<br>ST23_UT_R | GCTRCCGTTGACCT TTATTGC<br>GCCGAAGCGTTCA TAGAAATCC | 25<br>26 | 247 | See Table 4 | | 97% (8); also identifies K. variicola and K. quasipneumoniae | 3 |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| CG25_UT | SNP (C57 to T) | CG25_UT_F | GGCATTGGCGTCA ATAAAGC | 27 | 266 | See Table 4 | | 96% (11) | 3 |
| | | CG25_UT_R | ATAGCCGCCAGAC GAATTACCA | 28 | | | | | |
| CG29_UT | SNP (C30 to G) | CG29_UT_F | TCGACACATCGT CGTCTTTC | 29 | 259 | See Table 3 | | 98% (6) | 3 |
| | | CG29_UT_R | TGCTGCACAGCAC TCGTAAG | 30 | | | | | |
| CG34_UT | SNP (C36 to T) | CG34_UT_F | GACGATGTYGATG TGGCGATT | 31 | 293 | See Table 4 | | 96% (12) | 3 |
| | | CG34_UT_R | ACGCCCTGCCCGT GAATG | 32 | | | | | |
| CG35_UT[b] | SNP (C34 to T) | CG35_UT_F | GTCGTCTGGTTCGG TCATTC | 33 | 247 | Sequence type not available | KlebSeq on non-CG35 K. pneumoniae | 98% (5) | 3 |
| | | CG35_UT_R | GGTGTACAGCGAG GTCATAAAGG | 34 | | | | | |
| CG36_UT2 | SNP (A31 to G) | CG36_UT2_F | GCAGGCATGGAGC GTGT | 35 | 245 | See Table 4 | | 97% (8); also identifies K. variicola and K. quasipneumoniae | 3 |
| | | CG36_UT2_R | GCTTCGCAGTAA ACCGTAA | 36 | | | | | |
| CG37_UT | SNP (G40 to A) | CG37_UT_F | CCCGTTGGCCATCG TATGTC | 37 | 250 | See Table 4 | | 96.5% (9) | 3 |
| | | CG37_UT_R | GAGCGCATAGAAG TGACCATTC | 38 | | | | | |
| CG42_UT | SNP (C40 to A) | CG42_UT_F | CTCYAGCACGATG TCGTAAGG | 39 | 248 | See Table 4 | | 97.5% (7) | 3 |
| | | CG42_UT_R | GCGAGCATCGYGA GATTAGYG | 40 | | | | | |
| innerCG42_UT | SNP (C41 to T) | innerCG42_UT_F | GCCCAAAGCATGG TCTATGAAC | 41 | 248 | See Table 4 | | 96.5% (9) | 3 |
| | | innerCG42_UT_R | CGCACGTCGGTTAT TTGGTTG | 42 | | | | | |
| CG43_UT | SNP (T24 to C) | CG101_UT_F | GGRCCCAGCTATG TGC | 43 | 264 | See Table 4 | | 96% (11); also identifies K. variicola and K. quasipneumoniae | 3 |
| | | CG101_UT_R | CCACCATTCRATGC TTGCTTT | 44 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| CG45_UT | SNP (C27 to A) | CG45_UT_F | ACCGGCTCGTCGC CTTTC | 45 | 228 | See Table 4 | | 96.5% (8) | 3 |
| | | CG45_UT_R | TCACACCAGCCCA TATACCA | 46 | | | | | |
| CG48_UT | SNP (T34 to A) | CG48_UT_F | GCTTCGCATTCGG TAGCTGT | 47 | 164 | Sequence type not available | KlebSeq on non-CG48 K. pneumoniae | 97% (5); also identifies K. variicola and K. quasipneumoniae | 3 |
| | | CG48_UT_R | CAACTCGGCRCTGT TCGT | 48 | | | | | |
| CG76_UT | SNP (G29 to A) | CG76_UT_F | TAGCCGCTCTTGTT GATGGA | 49 | 236 | Sequence type not available | KlebSeq on non-CG76 K. pneumoniae | 98% (5); also identifies K. variicola and K. quasipneumoniae | 3 |
| | | CG76_UT_R | ACGCTGTGGACGC AGTA | 50 | | | | | |
| CG86_UT | SNP (C31 to T) | CG86_UT_F | ATACCCGGCGGAA GAYCT | 51 | 240 | Sequence type not available | KlebSeq on non-CG86 K. pneumoniae | 97.5% (6) | 3 |
| | | CG86_UT_R | AGGGCCAGCATCG CTTTCAG | 52 | | | | | |
| CG105_UT | SNP (C27 to T) | CG105_UT_F | CAGCCAGGACGCT TTCGTTAG | 53 | 258 | See Table 4 | | 96.5% (10) | 3 |
| | | CG105_UT_R | TCGGCGTTGAGGTT RCT | 54 | | | | | |
| CG111_UT | SNP (C41 to T) | CG111_UT_F | CCAGCAACTGCGC TTTGTC | 55 | 270 | See Table 4 | | 96% (11) | 3 |
| | | CG111_UT_R | CGTCTGGAGCATG GAAGATGA | 56 | | | | | |
| ST133_UT | SNP (C40 to T) | ST133_UT_F | CGTTCTCAGCAGTT CGATTTCATCT | 57 | 277 | See Table 3 | | 90% (28) | 3 |
| | | ST133_UT_R | CGCCGATAAGCAG TCGCT | 58 | | | | | |
| ST134_UT | SNP (G34 to T) | ST134_UT_F | CCGATGGCGACAA ATAAACCA | 59 | 263 | Sequence type not available | Specimen MLST KlebSeq on non-ST134 K. pneumoniae | 97% (8) | 3 |
| | | ST134_UT_R | GCAGTGGAAGAGG CTCTGTA | 60 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| CG220_UT | SNP (G31 to A) | CG220_UT_F | CAACCCGCGCAC TTTC | 61 | 253 | Sequence type not available | KlebSeq on non-CG220 K. pneumoniae | 98% (6); also identifies K. variicola and K. quasipneumoniae | 3 |
| | | CG220_UT_R | CCGTCCAGACGA TATCTTTG | 62 | | | | | 3 |
| CG258_UT | SNP (G45 to A) | CG258_UT_F | TTRACAGAATGGC AGAGAAGAAGG | 63 | 234 | See Table 4 | | 98% (5) | 3 |
| | | CG258_UT_R | GTGGCGGCGTTTA CAAATCAG | 64 | | | | | |
| CG258wo395_UT | SNP (T42 to G) | CG258wo395_UT_F | GAGCTGACCGAAG AGTTCATCA | 65 | 259 | See Table 4 | | 98% (6); also identifies K. variicola and K. quasipneumoniae | 3 |
| | | CG258wo395_UT_R | GCAGTTCCAGAGC CTGTTTC | 66 | | | | | |
| ST258_UT1[c] | SNP (T35 to C) | ST258_UT1_F | ATGTGTGTCGCGC AGTG | 67 | 120 | See Table 4 | | 95% (6); also identifies K. variicola and K. quasipneumoniae | 3 |
| | | ST258_UT1_R | GCTGACCGAGACG TTGTC | 68 | | | | | |
| ST258_UT2 | SNP (T30 to A) | ST258_UT2_F | TCAGTTTGCCAGTC TCGTTT | 69 | 238 | See Table 4 | | 97% (9) | 3 |
| | | ST258_UT2_R | GCGTCTGGCGTAA GAGGTA | 70 | | | | | |
| ST258clade1_UT | SNP (C35 to A) | ST258clade1_UT_F | GATCAGATCCAAC GGGCAGAAG | 71 | 234 | See Table 4 | | 96.5% (9) | 3 |
| | | ST258clade1_UT_R | TTGCCGCTTAATC AATTGC | 72 | | | | | |
| ST258clade2_UT | SNP (G37 to T) | ST258clade2_UT_F | GCTACCTGCGGG TTGTTT | 73 | 230 | See Table 4 | | 95% (12) | 3 |
| | | ST258clade2_UT_R | GCCACGATCTTCCT GCTGAA | 74 | | | | | |
| ST340_UT | SNP (C38 to A) | ST340_UT_F | TCGAGCCGGTTTGT TCATCG | 75 | 256 | See Table 4 | | 97% (8) | 3 |
| | | ST340_UT_R | CCGGACTACAGGA CACTACA | 76 | | | | | |
| ST380_UT | SNP (C34 to T) | ST380_UT_F | GACAGTCACCCTT ACCTACTACC | 77 | 300 | See Table 4 | | 97.5% (8) | 3 |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| | | ST380_UT_R | CAGGTGCCGGATTAAACTC | 78 | | | | | |
| CG392_UT | SNP (G37 to A) | CG392_UT_F | CATGCAGGAGAAGGCAAA | 79 | 255 | See Table 4 | | 96% (11) | 3 |
| | | CG392_UT_R | ACCCAGGCGAAGCGATGTTC | 80 | | | | | |
| ST395_UT | SNP (C34 to T) | ST395_UT_F | CCCTTTGGGCGGCRCAT | 81 | 261 | Sequence type not available | | 97% (8) | 3 |
| | | ST395_UT_R | AACGCTCAGGCGGAAGAC | 82 | | | | | |
| ST437_UT | SNP (G35 to T) | ST437_UT_F | CGACCATGATATGGCGGTGTTC | 83 | 290 | See Table 4 | | 97% (9) | 3 |
| | | ST437_UT_R | TGACCGCGCCTTTACGAT | 84 | | | | | |
| AMR Gene Assays | | | | | | | | | |
| blaKPC_UT1 | presence/absence | blaKPC_UT1_F | CGTCTAGTTCTGCTGTCTTGT | 85 | 338 | TG79504 | | | 1 |
| | | blaKPC_UT1_R | ACCGTCATGCCTGTTGTC | 86 | | | | | |
| blaKPC_UT2 | presence/absence | blaKPC_UT2_F | TTGTTGATTGGCTAAAGGGAAAAC | 87 | 133 | TG79504 | | | 1 |
| | | blaKPC_UT2_R | CAGACGACGGCATAGTCATT | 88 | | See Table 4 | | | |
| blaNDM_UT1 | presence/absence | blaNDM_UT1_F | GGACAAGATGGGCGGTATG | 89 | 323 | US-CA-2010b (Bioproject PRJNA252957) | | | 1 |
| | | blaNDM_UT1_R | CGGCGTAGTGCTCAGTG | 90 | | | | | |
| blaNDM_UT2 | presence/absence | blaNDM_UT2_F | CAACTGGATCAAGCAGGAGAT | 91 | 130 | US-CA-2010b (Bioproject PRJNA252957) | | | 1 |
| | | blaNDM_UT2_R | CGACAACGCATTGGCATAAG | 92 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| blaVIM_UT | presence/absence | blaVIM_UT_F1 | GGCGGGCGTTGATGTCCTT | 93 | 237 | US-WA-2010 (Bioproject PRJNA252957) | | | 1 |
| | | blaVIM_UT_R1 | GGCACAACCACCGTATAGCA | 94 | | | | | |
| | | blaVIM_UT_R2 | CGCACACCACCATAGAGCA | 95 | | | | | |
| blaOXA-48_UT | presence/absence | blaOXA-48_UT_F1 | TGGCTCGAYGGTGGTATTCG | 96 | 201 | No positive available | | | 1 |
| | | blaOXA-48_UT_F2 | GGCTCGATGGCGGCATTC | 97 | | | | | |
| | | blaOXA-48_UT_R1 | GACCCACCAGCCAATCTTAG | 98 | | | | | |
| | | blaOXA-48_UT_R2 | GACCCACCAACCGATCTGAG | 99 | | | | | 1 |
| blaCTX-M-G1_64_UT | presence/absence | blaCTX-M-G1_64_UT_F | CCGTCACGCTGTTGTTAGG | 100 | 157 | TG79504 | | | 1 |
| | | blaCTX-M-G1_64_UT_R | CGCTCATCAGCACGATAAAGT | 101 | | | | | |
| blaCTX-M-G1_UT1 | presence/absence | blaCTX-M-G1_UT2_F | GACGATGTCACTGGCTGAG | 102 | 350 | TG79504 | | | 1 |
| | | blaCTX-M-G1_UT2_R | CCACAACCCAGGAAGCAG | 103 | | | | | |
| blaCTX-M-G2_UT1 | presence/absence | blaCTX-M-G2_UT1_F | TGGCGCAGACCCTGAAAA | 104 | 181 | US-NY-2005d (Bioproject PRJNA252957) | | | 1 |
| | | blaCTX-M-G2_UT1_R | ATATCGTTGGTGGTGCCATAA | 105 | | | | | |
| blaCTX-M-G2_UT2 | presence/absence | blaCTX-M-G2_UT2_F | ATGGCGCAGACCCTGAAA | 106 | 158 | US-NY-2005d (Bioproject PRJNA252957) | | | 3 |
| | | blaCTX-M-G2_UT2_R | CCGCTGCCGGTTTTATCG | 107 | | | | | |
| blaCTX-M-G8_G25_UT1 | presence/absence | blaCTX-M-G8G25_UT1_F | GAGCCGACGCTCAACACC | 108 | 201 | No positive available | | | 1 |
| | | blaCTX-M-G8G25_UT1_R | CCCGACAACCCACGATGT | 109 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| blaCTX-M-G8_G25_UT2 | presence/absence | blaCTX-M-G8G25_UT2_F<br>blaCTX-M-G8G25_UT3_R | GCTCAACACCGCG ATCCC<br>CCCGACAACCCAC GATGT | 110<br>111 | 193 | No positive available | | | 3 |
| blaCTX-M-G9_UT1 | presence/absence | blaCTX-M-G9_UT1_F<br>blaCTX-M-G9_UT1_R | TTCGTCTGGATCGC ACTGA<br>GATGATTCTCGCCG CTGAAG | 112<br>113 | 374 | TG28186 (*Escherichia coli*) | | | 1 |
| blaCTX-M-G9_UT2 | presence/absence | blaCTX-M-G9_UT2_F<br>blaCTX-M-G9_UT2_R | CGCTGGTTCTGGTG ACCTA<br>GATGATTCTCGCCG CTGAAG | 114<br>115 | 86 | TG28186 (*Escherichia coli*) | | | 1 |
| blaGES_UT | presence/absence | blaGES_UT_F<br>blaGES_UT_R | GGTGCAGCTTAGC GACAATG<br>CTCCCGTTTGGTTT CCGATCAG | 116<br>117 | 275 | No positive available | | | 1 |
| gyrA_Kleb_UT1 | region of interest quinolone resistance determining region at nucleotides 77-91. Wild type is SAVYD. | gyrA_Kleb_UT1_F<br>gyrA_Kleb_UT1_R | CAATGACTGGAAC AAAGCCT<br>CGATGGAACCAAA GTTACCC | 118<br>119 | 170 | susceptible: TG22086 (Bioproject PRJEB7967) resistant: TG22074 | | 95% (9); also identifies *K. quasipneumoniae* and *K. varicola* gyrA | 1 |
| parC_Kleb_UT2 | region of interest quinolone resistance determining region at nucleotides 77-85. Wild type is CYE. | parC_Kleb_UT2_F<br>parC_Kleb_UT2_R | CAGCGCGAAATTC AAAAAGT<br>GCGAAAGATTTGG GATCGTC | 120<br>121 | 180 | susceptible: TG22074 resistant: No positive available | | 97.5% (5) | 1 |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| qnrA_UT | presence/absence | qnrA_UT_F<br>qnrA_UT_R | GATTTGAGYGACA<br>GCCGTTT<br>GCAGAAGTACATC<br>TTATGGCTGA | 122<br>123 | 297 | Brazil-2009b (Bioproject PRJNA252957) | | | 2 |
| qnrC_UT | presence/absence | qnrC_UT_F<br>qnrC_UT_R | GCTAATTTCTCACA<br>GGCAAACTTT<br>ACAACCCGTAATG<br>TAAGCAGAG | 124<br>125 | 78 | No positive available | | | 2 |
| qnrD_UT | presence/absence | qnrD_UT_F<br>qnrD_UT_R | CGACAGAATAGC<br>TTGGAAGG<br>CCAGTTATCACAGT<br>GCCATTC | 126<br>127 | 306 | No positive available | | | 2 |
| qnrS_UT2 | presence/absence | qnrS_UT_F<br>qnrS_UT_R1<br>qnrS_UT_R2 | GTGCTAACTTGCGT<br>GATACGA<br>TCCATATTGGCATA<br>GGAAAGATTACA<br>TCCATATTGGCATA<br>AGACAGGTTACA | 128<br>129<br>130 | 286 | US-FL-2008 (Bioproject PRJNA252957) | | | 2 |
| qnrB-C1_UT | presence/absence | qnrB-C1_UT_F<br>qnrB-C1_UT_R | CGACGTTCAGTGG<br>TTCRGATCT<br>GCKGCTCGCCAGT<br>CGAAA | 131<br>132 | 61 | TG22084 | | | 2 |
| qnrB-C2_UT | presence/absence | qnrB-C2_UT_F<br>qnrB-C2_UT_R | ACCAATCTAAGCT<br>ACGCCAACTT<br>CCTGAGTTCCCATC<br>CAGCG | 133<br>134 | 82 | No positive available | Positive specimen analysis | | 2 |
| qnrB-C3_UT | presence/absence | qnrB-C3_UT_F<br>qnrB-C3_UT_R | CGCATATATCACC<br>AATACCAACTT<br>GTTCCAGGAKCAA<br>CGATGCC | 135<br>136 | 281 | TG41249 (Providencia stuartii) | | | 2 |
| aac6-Ib_UT | presence/absence and SNP (T36 to A or C AND G267 to T confers | aac6-Ib_UT_F1<br>aac6-Ib_UT_F2<br>ac6-Ib_UT_R | CCCAGTCGTACGTT<br>GCTCTTG<br>GCTCAGTCGTACAT<br>TGCACTC<br>CCTGGCGTGTTGA<br>ACCATGTAC | 137<br>138<br>139 | 303 | aac6-Ib: TG22074<br>aac6-Ib-cr: US-VA-2007 (Bioproject PRJNA252957) | | | 2 |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| | quinolone resistance rather than aminoglycoside resistance) | | | | | | | | |
| aac3-II_UT | presence/absence | aac3-II_UT_F | CGCGTCGAACAGG TAGCA | 140 | 210 | TG79504 | | | 2 |
| | | aac3-II_UT_R | CGGTGGGTGACGT ATGAGATG | 141 | | | | | |
| aph3-I_UT | presence/absence | aph3-I_UT_F | GCGTTGCCAATGA TGTTACAGA | 142 | 277 | TG22074 | | | 2 |
| | | aph3-I_UT_R | GCCTGAGCGAGAC GAAATACG | 143 | | | | | |
| aadB_UT | presence/absence | aadB_UT_F | GCGCGTCAYGGAG GAGTTG | 144 | 268 | US-MD-2006 (Bioproject PRJNA252957) | | | 2 |
| | | aadB_UT_R | TGCGAGCCTGTAG GACTCTA | 145 | | | | | |
| aadA_UT | presence/absence | aadA_UT_F | GGCAGGCCAATGA CATTCTTG | 146 | 241 | TG22074 | | | 2 |
| | | aadA_UT_R | CGGGACAACGTAA GCACTACA | 147 | | | | | |
| arr_UT | presence/absence | arr_UT_F1 | CCACGGCGCTTTA AGTCCTC | 148 | 245 | TG22074 | | | 2 |
| | | arr_UT_F2 | CATGTAAACCACG ACGTTTAAATCTTC | 149 | | | | | |
| | | arr_UT_R | GGAGCTGAACTTG CTATGTCACT | 150 | | | | | |
| aadA5_UT | presence/absence | aadA5_UT_F | GCTGCGACACTGG ACACAATC | 151 | 211 | Israel-2007b (Bioproject PRJNA252957) | | | 2 |
| | | aadA5_UT_R | CGCTTCGAGCGAC AACAGTTAG | 152 | | | | | |
| armA | presence/absence | armA_UT1_F | ACTATTCTGCCTAT CCTAATTGGG | 153 | 121 | TG22074 | | | 2 |
| | | armA_UT1_R | TCATTTAATGTTGC GACTCTTTCA | 154 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| rmtA_UT1 | presence/absence | rmtA_UT1_F | GAATTGGACTGCC TCTACGATT | 155 | 123 | No positive available | | | 2 |
| | | rmtA_UT1_R | GCACGCCATACA GATGT | 156 | | | | | |
| rmtB_UT1 | presence/absence | rmtB_UT1_F | AAGGCATGGAGGC GAAC | 157 | 100 | No positive available | | | 2 |
| | | rmtB_UT1_R | AAGTATATAAGTT CTGTTCCGATGGT | 158 | | | | | |
| rmtC_UT1 | presence/absence | rmtC_UT1_F | AATACTCCACACTT TATCCACCAA | 159 | 97 | Guatemala-2009 (Bioproject PRJNA252957) | | | 2 |
| | | rmtC_UT1_R | TTCTTGCGAACCTC CTTCTC | 160 | | | | | |
| rmtD1&D2 | presence/absence | rmtD1&D2_F | AACGATGCGACGA TCCATT | 161 | 142 | No positive available | | | 2 |
| | | rmtD1&D2_R | GCGATTTGCTGTGC GAAA | 162 | | | | | |
| npmA | presence/absence | npmA_UT1_F | CCGCTTGCTGGTAC ATATCTA | 163 | 102 | No positive available | Positive specimen analysis | | 2 |
| | | npmA_UT1_R | CCTATCTCGTCCGC TATCTG | 164 | | | | | |
| dfrA1_UT | presence/absence | dfrA1_UT_F | AATGGCTGTTGGTT GGACG | 165 | 63 | TG42433 | | | 2 |
| | | dfrA1_UT_R | CATACTTTCGGTTG GGTAATGCT | 166 | | | | | |
| dfrA15_UT | presence/absence | dfrA15_UT_F | AATATGCCGTTGTA ACTCGTTCA | 167 | 117 | No positive available | | | 2 |
| | | dfrA15_UT_R | ACACAATCACATG ATCCGTTATCG | 168 | | | | | |
| dfrA16_UT | presence/absence | dfrA16_UT_F | AGTATGCAGTTGT AACTCGCTCTA | 169 | 129 | No positive available | | | 2 |
| | | dfrA16_UT_R | CACCACCACCAGA AACGATAAC | 170 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| dfrA14-30_UT | presence/absence | dfrA14-30_UT_F | GTGATTGGTTGCG GTCCA | 171 | 261 | US-PA-2001 (Bioproject PRJNA252957) | | | 2 |
| | | dfrA14-30_UT_R | CCCGCCACCAGAC ACTAT | 172 | | | | | |
| dfrA6-31_UT | presence/absence | dfrA6-31_UT_F | YGAGAATGGAGTA ATTGCTCT | 173 | 277 | No positive available | | | 2 |
| | | dfrA6-31_UT_R | WATTTCACCACCA CCAGAAACAAA | 174 | | | | | |
| dfrA26-13_UT | presence/absence | dfrA26-13_UT_F | GGGWGCCAATCGG GTTAT | 175 | 85 | US-CA-2007a (Bioproject PRJNA252957) | | | 2 |
| | | dfrA26-13_UT_R1 | CTCAGTGAGTCTGC GAAA | 176 | | | | | |
| | | dfrA26-13_UT_R2 | CTCGGTGAGCCTG CGAAA | 177 | | | | | |
| dfrA8_UT | presence/absence | dfrA8_UT_F | AAAGACTACGAGC AGAATGCC | 178 | 60 | Brazil-2009b (Bioproject PRJNA252957) | | | 2 |
| | | dfrA8_UT_R | ACGGTAAGTGAAG TAAGTGTGAAG | 179 | | | | | |
| dfrA3b_UT | presence/absence | dfrA3b_UT_F | AACGCTGCCATTGT TACCA | 180 | 107 | No positive available | | | 2 |
| | | dfrA3b_UT_R | AAGCCTTGAAGTG TTCTGGAG | 181 | | | | | |
| dfrA9_UT | presence/absence | dfrA9_UT_F | AAGACAGGAGGTA TCCGATTTGA | 182 | 319 | No positive available | | | 2 |
| | | dfrA9_UT_R | CGTAGGCAGCTAA GTTCTCGTA | 183 | | | | | |
| dfrA24_UT | presence/absence | dfrA24_UT_F | AAGACCCGCATCAA TATCGTCATC | 184 | 60 | No positive available | | | 2 |
| | | dfrA24_UT_R | CATAGCAAGCCGT CCAAGAA | 185 | | | | | |
| dfrA27-28_UT | presence/absence | dfrA27-28_UT_F | AAGACTCTTACGA ACCATGTTGTT | 186 | 109 | Colombia-2009a (Bioproject PRJNA252957) | | | 2 |
| | | dfrA27-28_UT_R | CCTCTGCTCGGA ATCTATTG | 187 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| dfrA25_UT | presence/absence | dfrA25_UT_F | AAGCACTGACCTA TAACCAATGG | 188 | 302 | TG22010 | | | 2 |
| | | dfrA25_UT_R | CCCAGGAATGTTC GGAAAGAAA | 189 | | | | | |
| dfrA10_UT | presence/absence | dfrA10_UT_F | AAGCATTCAGAGA CACACCAA | 190 | 51 | TG21173 (Acinetobacter baumannii) | | | 2 |
| | | dfrA10_UT_R | AACCAACACCACC AATGACAT | 191 | | | | | |
| dfrA32_UT | presence/absence | dfrA32_UT_F | AAGGTGAGCAGCT AATCTTTAAGG | 192 | 134 | No positive available | Positive specimen analysis | | 2 |
| | | dfrA32_UT_R | TGACCCTGAAATTC CATTCTTTGA | 193 | | | | | |
| dfrA20_UT | presence/absence | dfrA20_UT_F | AAGTCGCACAACA TCTTGAAGG | 194 | 63 | No positive available | | | 2 |
| | | dfrA20_UT_R | AGATTTGAGCACC ACCAATAATGA | 195 | | | | | |
| dfrA23_UT | presence/absence | dfrA23_UT_F | AATCAATATCACG ACAGCGATCAA | 196 | 222 | No positive available | | | 2 |
| | | dfrA23_UT_R | CTTCACGGGATGG GTCTCA | 197 | | | | | |
| dfrA7_UT | presence/absence | dfrA7_UT_F | AATCAGTGGCTCCT TGTTGG | 198 | 53 | TG21968 | | | 2 |
| | | dfrA7_UT_R | GGAAGAACACCCA TAGAGTCAAAT | 199 | | | | | |
| dfrA29_UT | presence/absence | dfrA29_UT_F | AATCAGTGGCTTCT TGTCGG | 200 | 246 | No positive available | | | 2 |
| | | dfrA29_UT_R | GTGGATGATAGAT AAGTGGATGGT | 201 | | | | | |
| dfrA17_UT | presence/absence | dfrA17_UT_F | AATGGCGTAATCG GTAGTGG | 202 | 174 | No positive available | Positive specimen analysis | | 2 |
| | | dfrA17_UT_R | GCTTTGAAATTCCGT TCTTTGACA | 203 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| dfrA18_UT | presence/absence | dfrA18_UT_F | ACGCATTGCTGTCA TTGGT | 204 | 160 | US-MD-2005 (Bioproject PRJNA252957) | | | 2 |
| | | dfrA18_UT_R | CTCGCTGGCACTG GAATC | 205 | | | | | |
| dfrA3_UT | presence/absence | dfrA3_UT_F | ACTCTATGCCGAG GCTCTG | 206 | 186 | No positive available | | | 2 |
| | | dfrA3_UT_R | CGCTGACGACTCA AGGTAAC | 207 | | | | | |
| dfrB1-8_UT | presence/absence | dfrB1-8_UT_F | WATGGGAGATGCG GTGCG | 208 | 67 | CAS813 (Bioproject PRJEB79967) | | | 2 |
| | | dfrB1-8_UT_R | GCWGTACCACCCG ACAATCT | 209 | | | | | |
| dfrB2-7_UT | presence/absence | dfrB2-7_UT_F | GCAGGGTCAAGTY GTCGG | 210 | 66 | No positive available | | | 3 |
| | | dfrB2-7_UT_R | TCGGACTCGACSGC ATAG | 211 | | | | | |
| dfrB3_1_UT | presence/absence | dfrB3_1_UT_F | ACCCGACAACTTG ACCCT | 212 | 129 | No positive available | | | 2 |
| | | dfrB3_1_UT_R | ACCAACACAACAA TGGAGTCA | 213 | | | | | |
| dfrB4_UT | presence/absence | dfrB4_UT_F | AATCTCACCCAGG CTCAGT | 214 | 50 | No positive available | | | 2 |
| | | dfrB4_UT_R | CCGTTCAAGCGCA GTCAT | 215 | | | | | |
| sul1_UT | presence/absence | sul1_UT_F | GCTGGTGGTTATGC ACTCAG | 216 | 287 | TG22074 | | | 2 |
| | | sul1_UT_R | CGCCAAGAAGGA TTTCCG | 217 | | | | | |
| sul2_UT | presence/absence | sul2_UT_F | CATCATTTTCGGCA TCGTCAAC | 218 | 278 | TG22074 | | | 2 |
| | | sul2_UT_R | GCGACAAGGCATA GGCTT | 219 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| sul3_UT | presence/absence | sul3_UT_F | AAAGCCTTAATGACAGGTTTGAGTGAAGATGGAGCAGATGTGATTGAT | 220 | 110 | US-IL-2009b (Bioproject PRJNA252957) | | | 2 |
| | | sul3_UT_R | | 221 | | | | | |
| catA_UT | presence/absence | catA_UT_F | CGCAAGATGTGGCGTGTTAC | 222 | 225 | US-IL-2009b (Bioproject PRJNA252957) | | | 2 |
| | | catA_UT_R | ARACGGCATGATGAACCTGAATC | 223 | | | | | |
| cm1A-B_UT | presence/absence | cm1A-B_UT_F | TCGCCACAGCGGTATCTG | 224 | 216 | TG22074 | | | 2 |
| | | cm1A-B_UT_R | GGGAAACACAAGACAGACCGA | 225 | | | | | |
| floR_UT | presence/absence | floR_UT_F1 | GGCGACGGCCAATTCTACTTG | 226 | 220 | US-MO-2006 (Bioproject PRJNA252957) | | | 2 |
| | | floR_UT_F2 | GACGGCCGATCCTGCTTG | 227 | | | | | |
| | | floR_UT_R1 | AACGCCAGCAYCGAACTGAA | 228 | | | | | |
| | | floR_UT_R2 | AACGCCAGHATCGAACTGAA | 229 | | | | | |
| mphA_UT | presence/absence | mphA_UT_F | GCCGATACCTCCCAACTGTAC | 230 | 219 | TG22074 | | | 2 |
| | | mphA_UT_R | GAACGGCAGGCGATTCTTG | 231 | | | | | |
| strA_UT | presence/absence | strA_UT_F | GCGCTGCCCAGTTCTCTTC | 232 | 279 | TG22074 | | | 2 |
| | | strA_UT_R | CCCGCAATGCCGTCAATC | 233 | | | | | |
| strB_UT | presence/absence | strB_UT_F | CGTTTCGCAACCTGTTCTCATTG | 234 | 217 | TG22074 | | | 2 |
| | | strB_UT_R | CCCGGCATATTCGAGCAACATC | 235 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| mcr-1_UT | presence/absence | mcr-1_UT_F | TGGCAGCGACAAAGTCATC | 236 | 273 | No positive available | | | 2 |
| | | mcr-1_UT_R | TGCCGTGTATGTTCAGCTATC | 237 | | | | | |
| tetA_UT | presence/absence | tetA_UT_F1 | TTGCCGCATTTGGCATTCTG | 238 | 204 | TG32076 | | | 2 |
| | | tetA_UT_F2 | CGCTTGCCCGCATTTGGTATTC | 239 | | | | | |
| | | tetA_UT_R | GCGCCGGCATTCCGA | 240 | | | | | |
| tetB_UT | presence/absence | tetB_UT_F | TCGCTGCGTTGCTAAATATTGTC | 241 | 310 | No positive available | | | 2 |
| | | tetB_UT_R | ATTCCAAGCCTTTGTGGCAGG | 242 | | | | | |
| tetG_UT | presence/absence | tetG_UT_F1 | CCACGACCGTCGGCTT | 243 | 165 | TG21548 | | | 2 |
| | | tetG_UT_F2 | CACCACGACTGTTGGTTTGTC | 244 | | | | | |
| | | tetG_UT_F3 | ACACCGCGACCGTTGGTTT | 245 | | | | | |
| | | tetG_UT_R | GCGTGRCAAAAGCCAGAAGA | 246 | | | | | |
| tetD_UT | presence/absence | tetD_UT_F | TGAACAGCATTCTCGCTATCAAA | 247 | 251 | TG20538 (Escherichia coli) | | | 2 |
| | | tetD_UT_R | CAGCCGCTTTCGTCAAACG | 248 | | | | | |
| Virulence Gene Assays |
| rmpA_UT | presence/absence | rmpA_UT_F | AAGAGTATTGGTTGACWGCAGGATT | 249 | 256 | TG60548 | | | 3 |
| | | rmpA_UT_R | TGTTAGCCGTGGATAATGTTTACAA | 250 | | | | | |
| clbA-colibactin_UT | presence/absence | clbA-colibactin_UT_F | GCGAGCTTGGTGTCGATATTGA | 251 | 322 | TG60548 | | | 3 |
| | | clbA-colibactin_UT_R | GTGATGAGTGGAGAGCTAATGC | 252 | | | | | |

TABLE 4-continued

| Assay Name | Assay type | Primer Name | Primer Sequence without Universal Tail[a] | SEQ ID NO: | Amplicon length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| clbC-colibactin_UT | presence/absence | clbC-colibactin_UT_F | GCCGCCGAGTGAT ACAAGT | 253 | 316 | TG60548 | | | 3 |
| | | clbC-colibactin_UT_R | GGTAGCAGGTTCA TCCAGGTT | 254 | | | | | |
| clbP-colibactin_UT | presence/absence | clbP-colibactin_UT_F | GCTATGCCTCCGCC AATTATGA | 255 | 345 | TG60548 | | | 3 |
| | | clbP-colibactin_UT_R | CACTATTACCACGC CAACTGTTACT | 256 | | | | | |
| clbQ-colibactin_UT | presence/absence | clbQ-colibactin_UT_F | AGCCGCTGTGTCTT ACGATG | 257 | 258 | TG60548 | | | 3 |
| | | clbQ-colibactin_UT_R | CGATCTTTCCATA AACGCCTGAT | 258 | | | | | |
| iroB-salmochelin_UT | presence/absence | iroB-salmochelin_UT_F | AAACGACGGCGAA CCCATT | 259 | 182 | TG60548 | | | 3 |
| | | iroB-salmochelin_UT_R | CGACTTCACTGGC GGAATCC | 260 | | | | | |
| irp2-yersiniabactin_UT | presence/absence | irp2-yersiniabactin_UT_F | ATTGCGGCGGACG AGAG | 261 | 274 | TG60548 | | | 3 |
| | | irp2-yersiniabactin_UT_R | GCTGACGACGGCG AACA | 262 | | | | | |
| ybtE-yersiniabactin_UT | presence/absence | ybtE-yersiniabactin_UT_F | CGGCGACATGCCG ACTAT | 263 | 319 | TG60548 | | | 3 |
| | | ybtE-yersiniabactin_UT_R | CGCCGCCTGCCTG AAT | 264 | | | | | |
| ybtQ-yersiniabactin_UT | presence/absence | ybtQ-yersiniabactin_UT_F | GCAGAACCGATGG CGATGT | 265 | 349 | TG60548 | | | 3 |
| | | ybtQ-yersiniabactin_UT_R | GCGTCAGGCGGCG AATA | 266 | | | | | |
| ybtS-yersiniabactin_UT | presence/absence | ybtS-yersiniabactin_UT_F | GAAGAGTGTTATG TCTATGAGCGTCAA | 267 | 399 | TG60548 | | | 3 |
| | | ybtS-yersiniabactin_UT_R | TGCGTTCTGCGTCG TTGT | 268 | | | | | |

TABLE 4-continued

| Assay Name | Assay type | Primer Name | Primer Sequence without Universal Tail[a] | SEQ ID NO: | Ampli-con length | Example isolate used for WGS validation of assay | Validation method when no isolate available | Threshold of identity to reference where appropriate (Maximum number of SNPs allowed) | Multiplex Assay Pool |
|---|---|---|---|---|---|---|---|---|---|
| iucD-aerobactin_UT | presence/absence | iucD-aerobactin_UT_F<br>iucD-aerobactin_U_TR | GGCGGCAAGCGAG<br>TCA<br>TCAGGCGTGAAGT<br>ATTCGTTGG | 269<br>270 | 170 | TG60548 | | | 3 |
| iutA-aerobactin_UT | presence/absence | iutA-aerobactin_UT_F<br>iutA-aerobactin_UT_R | CCGAACTGGAACA<br>GCAGATTCA<br>GCATCGCCGTTACC<br>GTCAA | 271<br>272 | 469 | TG60548 | | | 3 |
| ABCt-00025_UT | presence/absence | ABCt-00025_UT_F1<br>ABCt-00025_UT_F2<br>ABCt-00025_UT_R | CCACTGGTAAACG<br>GTTTATCCTC<br>CCGCTGGTAAAAG<br>GTTTATCCTC<br>GAACTGGCACMSA<br>AATATCCC | 273<br>274<br>275 | 374 | TG60548 | | | 3 |
| CobW-00325_UT | presence/absence | CobW-00325_UT_F1<br>CobW-00325_UT_F2<br>CobW-00325_UT_R1<br>CobW-00325_UT_R2 | AACGACACTGCTT<br>AACCACATCCTGAA<br>AACGACACTGCTT<br>AACCATATTCTGAA<br>CGGTGGACTCAAT<br>GACAAGT<br>CGGTAGACTCAAT<br>AACAAGT | 276<br>277<br>278<br>279 | 254 | TG60548 | | | 3 |
| wzi_UT[d] | sequence-based | wzi_UT_F<br>wzi_UT_R | CGCGAGYGCTTTCT<br>ATCTTG<br>GAGASCCACTGGTT<br>CCAGAA | 280<br>281 | 580 | See Table 2 | | | 3 |

[a]Universal tail sequences are ACCCAACTGAATGGAGC (SEQ ID NO: 282) for forward read and ACGCACTTGACTTGTCTTC (SEQ ID NO: 283) for reverse read. The universal tail sequences precede the assay-specific primer sequence, for example, the primer sequence with the universal tail for the wzi_UT assay is ACCCAACTGAATGGAGCCGCGAGYGCTTTCTATCTTG (i.e., SEQ ID NO: 284) consisting of SEQ ID NOs: 280 and 282) for the forward primer and ACGCACTTGACTTGTCTTCGAGASCCACTGGTTCCAGAA (SEQ ID NO: 285 consting of SEQ ID NOs: 281 and 283) for the reverse primer.
[b]CG35 is the only assay for which the identity threshold must be applied if the SNP state indicates CG35 is present (Some strains of Enterobacter aerogenes amplify and have C34T for this target). For all other assays, the canonical SNP state is specific to that clonal group of K. pneumoniae; the identity threshold just makes the assay Klebsiella-specific.
[c]CG258wo395 is the assay that captures all of CG258 except for ST395 (as shown in FIG. 4).
[d]From Bowers JR, Kitchel B, Driebe EM, MacCannell DR, Roe C, Lemmer D, de Man T, Rasheed JK, Engelthaler DM, Kelim P, Limbago BM. 2015. Genomic Analysis of the Emergence and Rapid Global Dissemination of the Clonal Group 258 Klebsiella pneumoniae Pandemic. PLoS One 10:e0133727.
[e]From Brisse S, Passet V, Haugaard AB, Babosan A, Kassis-Chikhani N, Struve C, Decre D. 2013. wzi Gene sequencing, a rapid method for determination of capsular type for Klebsiella strains. J Clin Microbiol 51:4073-4078.

TABLE 5

In-house genomes used for KlebSeq strain identification validaton.

| Sample | Species | K. pneumoniae sequence type | Accession information |
| --- | --- | --- | --- |
| 8045 | K. pneumoniae | 82 | Bioproject PRJEB7967 |
| A5054 | K. pneumoniae | 82 | Bioproject PRJEB7967 |
| Brazil-2009b | K. pneumoniae | ST437 | Bioproject PRJNA252957 |
| C3091 | K. pneumoniae | NF | Bioproject PRJEB7967 |
| Canada-2009a | K. pneumoniae | 512 | Bioproject PRJNA252957 |
| Canada-2009b | K. pneumoniae | 20 | Bioproject PRJNA252957 |
| Canada-2009c | K. pneumoniae | 152 | Bioproject PRJNA252957 |
| Canada-2009d | K. pneumoniae | SLVST815 | Bioproject PRJNA252957 |
| CAS698 | K. pneumoniae | 23 | Bioproject PRJEB7967 |
| CAS726 | K. pneumoniae | 23 | Bioproject PRJEB7967 |
| CAS727 | K. pneumoniae | 23 | Bioproject PRJEB7967 |
| CAS813 | K. pneumoniae | 23 | Bioproject PRJEB7967 |
| Guatemala-2009 | K. pneumoniae | 11 | Bioproject PRJNA252957 |
| India-2007a | K. pneumoniae | 101 | Bioproject PRJNA252957 |
| India-2007b | K. pneumoniae | 43 | Bioproject PRJNA252957 |
| Israel-2007a | K. pneumoniae | 512 | Bioproject PRJNA252957 |
| Israel-2007b | K. pneumoniae | 277 | Bioproject PRJNA252957 |
| Israel-2007c | K. pneumoniae | 340 | Bioproject PRJNA252957 |
| Israel-2007d | K. pneumoniae | 376 | Bioproject PRJNA252957 |
| Sp221 | K. pneumoniae | 249 | Bioproject PRJEB7967 |
| Sp29 | K. pneumoniae | 249 | Bioproject PRJEB7967 |
| TG22074 | K. pneumoniae | 15 | TBD* |
| TG22084 | K. pneumoniae | 15 | TBD* |
| TG22086 | K. pneumoniae | 34 | Bioproject PRJEB7967 |
| TG22092 | K. variicola | 2006 | TBD* |
| TG28459 | K. pneumoniae | 36 | Bioproject PRJEB7967 |
| TG31708 | K. pneumoniae | 23 | TBD* |
| TG31716 | K. pneumoniae | 23 | TBD* |
| TG31732 | K. pneumoniae | 23 | TBD* |
| TG31736 | K. pneumoniae | 260 | TBD* |
| TG32076 | K. pneumoniae | 42 | TBD* |
| TG64566 | K. pneumoniae | 101 | TBD* |
| TG64698 | K. pneumoniae | 23 | TBD* |
| TG65600 | K. pneumoniae | 2055 | TBD* |
| TG69833 | K. pneumoniae | 36 | TBD* |
| TG69835 | K. pneumoniae | 111 | TBD* |
| TG69845 | K. pneumoniae | 776 | TBD* |
| TG77275 | K. pneumoniae | 636 | TBD* |
| TG77291 | K. quasipneumoniae | 978 | TBD* |
| TG79500 | K. pneumoniae | 1401 | TBD* |
| TG79504 | K. pneumoniae | Unknown | TBD* |
| TG79508 | K. pneumoniae | 380 | TBD* |
| TG79512 | K. pneumoniae | SLV of ST34 | TBD* |
| TG79516 | K. pneumoniae | Unknown | TBD* |
| TG79520 | K. pneumoniae | 107 | TBD* |
| US-CA-2007a | K. pneumoniae | 340 | Bioproject PRJNA252957 |
| US-CA-2008 | K. pneumoniae | 833 | Bioproject PRJNA252957 |
| US-CA-2010a | K. pneumoniae | 11 | Bioproject PRJNA252957 |
| US-CA-2010b | K. pneumoniae | 37 | Bioproject PRJNA252957 |
| US-CA-2011 | K. pneumoniae | 14 | Bioproject PRJNA252957 |
| US-FL-2008 | K. pneumoniae | SLVST513 | Bioproject PRJNA252957 |
| US-GA-2006b | K. pneumoniae | 20 | Bioproject PRJNA252957 |
| US-GA-2009b | K. variicola | 1 SNP from ST360 | Bioproject PRJNA252957 |
| US-IL-2008b | K. pneumoniae | 14 | Bioproject PRJNA252957 |
| US-IL-2009a | K. pneumoniae | 258 | Bioproject PRJNA252957 |
| US-IL-2009b | K. pneumoniae | 258 | Bioproject PRJNA252957 |
| US-MD-2005 | K. pneumoniae | 228 | Bioproject PRJNA252957 |
| US-MD-2006 | K. pneumoniae | 11 | Bioproject PRJNA252957 |
| US-MD-2011 | K. pneumoniae | 14 | Bioproject PRJNA252957 |
| US-MI-2008 | K. pneumoniae | 14 | Bioproject PRJNA252957 |
| US-MO-2006 | K. pneumoniae | 14 | Bioproject PRJNA252957 |
| US-NC-1996 | K. pneumoniae | 37 | Bioproject PRJNA252957 |
| US-NM-2007 | K. pneumoniae | 258 | Bioproject PRJNA252957 |
| US-NY-2004a | K. pneumoniae | 234 | Bioproject PRJNA252957 |
| US-NY-2004c | K. pneumoniae | SLVST244 | Bioproject PRJNA252957 |
| US-NY-2004d | K. pneumoniae | 42 | Bioproject PRJNA252957 |
| US-NY-2005b | K. pneumoniae | 65 | Bioproject PRJNA252957 |
| US-NY-2005c | K. pneumoniae | ST258 clade 1 | Bioproject PRJNA252957 |
| US-NY-2009a | K. pneumoniae | ST258 clade 1 | Bioproject PRJNA252957 |
| US-PA-2001 | K. quasipneumoniae | 334 | Bioproject PRJNA252957 |
| US-SD-2012 | K. pneumoniae | 258 | Bioproject PRJNA252957 |
| US-TX-2001 | K. pneumoniae | SLVST427 | Bioproject PRJNA252957 |
| US-TX-2011 | K. pneumoniae | 39 | Bioproject PRJNA252957 |
| US-VA-2007 | K. pneumoniae | 45 | Bioproject PRJNA252957 |
| US-VA-2008a | K. pneumoniae | ST258 clade 1 | Bioproject PRJNA252957 |

TABLE 5-continued

In-house genomes used for KlebSeq strain identification validaton.

| Sample | Species | K. pneumoniae sequence type | Accession information |
|---|---|---|---|
| US-VA-2008b | K. pneumoniae | 719 | Bioproject PRJNA252957 |
| US-WA-2010 | K. pneumoniae | 147 | Bioproject PRJNA252957 |
| TG75900 | K. quasipneumoniae | 196 | TBD* |
| 8045 | K. pneumoniae | 82 | Bioproject PRJEB7967 |
| A5054 | K. pneumoniae | 82 | Bioproject PRJEB7967 |
| Brazil-2009b | K. pneumoniae | ST437 | Bioproject PRJNA252957 |
| C3091 | K. pneumoniae | NF | Bioproject PRJEB7967 |
| Canada-2009a | K. pneumoniae | 512 | Bioproject PRJNA252957 |
| Canada-2009b | K. pneumoniae | 20 | Bioproject PRJNA252957 |
| Canada-2009c | K. pneumoniae | 152 | Bioproject PRJNA252957 |
| Canada-2009d | K. pneumoniae | SLVST815 | Bioproject PRJNA252957 |
| CAS698 | K. pneumoniae | 23 | Bioproject PRJEB7967 |
| CAS726 | K. pneumoniae | 23 | Bioproject PRJEB7967 |
| CAS727 | K. pneumoniae | 23 | Bioproject PRJEB7967 |
| CAS813 | K. pneumoniae | 23 | Bioproject PRJEB7967 |
| Guatemala-2009 | K. pneumoniae | 11 | Bioproject PRJNA252957 |
| India-2007a | K. pneumoniae | 101 | Bioproject PRJNA252957 |
| India-2007b | K. pneumoniae | 43 | Bioproject PRJNA252957 |
| Israel-2007a | K. pneumoniae | 512 | Bioproject PRJNA252957 |
| Israel-2007b | K. pneumoniae | 277 | Bioproject PRJNA252957 |
| Israel-2007c | K. pneumoniae | 340 | Bioproject PRJNA252957 |
| Israel-2007d | K. pneumoniae | 376 | Bioproject PRJNA252957 |
| Sp221 | K. pneumoniae | 249 | Bioproject PRJEB7967 |
| Sp29 | K. pneumoniae | 249 | Bioproject PRJEB7967 |
| TG22074 | K. pneumoniae | 15 | TBD* |
| TG22084 | K. pneumoniae | 15 | TBD* |
| TG22086 | K. pneumoniae | 34 | Bioproject PRJEB7967 |
| TG22092 | K. variicola | 2006 | TBD* |
| TG28459 | K. pneumoniae | 36 | Bioproject PRJEB7967 |
| TG31708 | K. pneumoniae | 23 | TBD* |
| TG31716 | K. pneumoniae | 23 | TBD* |
| TG31732 | K. pneumoniae | 23 | TBD* |
| TG31736 | K. pneumoniae | 260 | TBD* |
| TG32076 | K. pneumoniae | 42 | TBD* |
| TG64566 | K. pneumoniae | 101 | TBD* |
| TG64698 | K. pneumoniae | 23 | TBD* |
| TG65600 | K. pneumoniae | 2055 | TBD* |
| TG69833 | K. pneumoniae | 36 | TBD* |
| TG69835 | K. pneumoniae | 111 | TBD* |
| TG69845 | K. pneumoniae | 776 | TBD* |
| TG77275 | K. pneumoniae | 636 | TBD* |
| TG77291 | K. quasipneumoniae | 978 | TBD* |
| TG79500 | K. pneumoniae | 1401 | TBD* |
| TG79504 | K. pneumoniae | Unknown | TBD* |
| TG79508 | K. pneumoniae | 380 | TBD* |
| TG79512 | K. pneumoniae | SLV of ST34 | TBD* |
| TG79516 | K. pneumoniae | Unknown | TBD* |
| TG79520 | K. pneumoniae | 107 | TBD* |
| US-CA-2007a | K. pneumoniae | 340 | Bioproject PRJNA252957 |
| US-CA-2008 | K. pneumoniae | 833 | Bioproject PRJNA252957 |
| US-CA-2010a | K. pneumoniae | 11 | Bioproject PRJNA252957 |
| US-CA-2010b | K. pneumoniae | 37 | Bioproject PRJNA252957 |
| US-CA-2011 | K. pneumoniae | 14 | Bioproject PRJNA252957 |
| US-FL-2008 | K. pneumoniae | SLVST513 | Bioproject PRJNA252957 |
| US-GA-2006b | K. pneumoniae | 20 | Bioproject PRJNA252957 |
| US-GA-2009b | K. variicola | 1 SNP from ST360 | Bioproject PRJNA252957 |
| US-IL-2008b | K. pneumoniae | 14 | Bioproject PRJNA252957 |
| US-IL-2009a | K. pneumoniae | 258 | Bioproject PRJNA252957 |
| US-IL-2009b | K. pneumoniae | 258 | Bioproject PRJNA252957 |
| US-MD-2005 | K. pneumoniae | 228 | Bioproject PRJNA252957 |
| US-MD-2006 | K. pneumoniae | 11 | Bioproject PRJNA252957 |
| US-MD-2011 | K. pneumoniae | 14 | Bioproject PRJNA252957 |
| US-MI-2008 | K. pneumoniae | 14 | Bioproject PRJNA252957 |
| US-MO-2006 | K. pneumoniae | 14 | Bioproject PRJNA252957 |
| US-NC-1996 | K. pneumoniae | 37 | Bioproject PRJNA252957 |
| US-NM-2007 | K. pneumoniae | 258 | Bioproject PRJNA252957 |
| US-NY-2004a | K. pneumoniae | 234 | Bioproject PRJNA252957 |
| US-NY-2004c | K. pneumoniae | SLVST244 | Bioproject PRJNA252957 |
| US-NY-2004d | K. pneumoniae | 42 | Bioproject PRJNA252957 |
| US-NY-2005b | K. pneumoniae | 65 | Bioproject PRJNA252957 |
| US-NY-2005c | K. pneumoniae | ST258 clade 1 | Bioproject PRJNA252957 |
| US-NY-2009a | K. pneumoniae | ST258 clade 1 | Bioproject PRJNA252957 |
| US-PA-2001 | K. quasipneumoniae | 334 | Bioproject PRJNA252957 |
| US-SD-2012 | K. pneumoniae | 258 | Bioproject PRJNA252957 |
| US-TX-2001 | K. pneumoniae | SLVST427 | Bioproject PRJNA252957 |

TABLE 5-continued

In-house genomes used for KlebSeq strain identification validaton.

| Sample | Species | K. pneumoniae sequence type | Accession information |
|---|---|---|---|
| US-TX-2011 | K. pneumoniae | 39 | Bioproject PRJNA252957 |
| US-VA-2007 | K. pneumoniae | 45 | Bioproject PRJNA252957 |
| US-VA-2008a | K. pneumoniae | ST258 clade 1 | Bioproject PRJNA252957 |
| US-VA-2008b | K. pneumoniae | 719 | Bioproject PRJNA252957 |
| US-WA-2010 | K. pneumoniae | 147 | Bioproject PRJNA252957 |
| TG75900 | K. quasipneumoniae | 196 | TBD* |

*Uploaded this study

In one aspect, the clonal group and/or subgroup detected is one or more of those shown in Table 6.

TABLE 6

| Clonal subgroup | Assay name | SEQ ID NOs |
|---|---|---|
| CG258 | | |
| CG258 | CG258_UT | 63/64 |
| | CG258wo395_UT | 65/66 |
| ST258 | ST258_UT1 | 67/68 |
| | ST258_UT2 | 69/70 |
| | ST258clade1_UT | 71/72 |
| | ST258clade2_UT | 73/74 |
| ST340 | ST340_UT | 75/76 |
| ST395 | ST395_UT | 81/82 |
| ST437 | ST437_UT | 83/84 |
| CG20 | CG20_UT | 21/22 |
| ST20 | ST20_UT | 23/24 |
| ST23 | ST23_UT | 25/26 |
| ST380 | ST380_UT | 77/78 |
| CG37 | CG37_UT | 37/38 |
| CG14 | CG14_UT | 13/14 |
| ST14 | ST14_UT | 15/16 |
| | innerST14_UT | 17/18 |
| ST15 | ST15_UT | 19/20 |

In another aspect, the AMR gene detected is one or more of those shown in Table 7.

TABLE 7

| AMR genes | Assay name | SEQ ID NOs |
|---|---|---|
| beta-lactamase genes c | blaKPC_UT1 | 85/86 |
| | blaKPC_UT2 | 87/88 |
| | blaNDM_UT1 | 89/90 |
| | blaNDM_UT2 | 91/92 |
| | blaVIM_UT | 93/94-95 |
| | blaOXA-48_UT | 96-97/98-99 |
| | blaCTX-M-G1_64_UT | 100/101 |
| | blaCTX-M-G1_UT | 102/103 |
| | blaCTX-M-G2_UT1 | 104/105 |
| | blaCTX-M-G2_UT2 | 106/107 |
| | blaCTX-M-G8_G25_UT1 | 108/109 |
| | blaCTX-M-G8_G25_UT2 | 110/111 |
| | blaCTX-M-G9_UT1 | 112/113 |
| | blaCTX-M-G9_UT2 | 114/115 |
| | blaGES_UT | 116/117 |
| colistin resistance gene | mcr-1_UT | 236/237 |

In yet another aspect, the virulence gene detected is one or more of those shown in Table 8.

TABLE 8

| Virulence genes | Assay name | SEQ ID NOs |
|---|---|---|
| rmpA | blaKPC_UT1 | 249/250 |
| wzi | wzi_UT | 280/281 |

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Montgomerie J Z. 1979. Epidemiology of Klebsiella and hospital-associated infections. Rev Infect Dis 1:736-753.10.1093/clinids/1.5.736.
2. Magill S S, Edwards J R, Bamberg W, Beldays Z G, Dumyati G, Kainer M A, Lynfield R, Maloney M, McAllister-Hollod L, Nadle J, Ray S M, Thompson D L, Wilson L E, Fridkin S K, Emerging Infections Program Healthcare-Associated Infections, Antimicrobial Use Prevalence Survey Team. 2014. Multistate point-prevalence survey of health care-associated infections. N Engl J Med 370: 1198-1208.10.1056/NEJMoa1306801.
3. Centers for Disease Control and Prevention. 2013. Antibiotic resistance threats in the United States, 2013. Centers for Disease Control and Prevention, Atlanta, GA
4. Xu Y, Gu B, Huang M, Liu H, Xu T, Xia W, Wang T. 2015. Epidemiology of carbapenem resistant Enterobacteriaceae (CRE) during 2000-2012 in Asia. J Thorac Dis 7:376-385.10.3978/j.issn.2072-1439.2014.12.33.

5. World Health Organization. 2014. Antimicrobial resistance global report on surveillance. World Health Organization, Geneva, Switzerland.
6. Correa L, Martino M D, Siqueira I, Pasternak J, Gales A C, Silva C V, Camargo T Z, Scherer P F, Marra A R. 2013. A hospital-based matched case-control study to identify clinical outcome and risk factors associated with carbapenem-resistant *Klebsiella pneumoniae* infection. BMC Infect Dis 13:80.10.1186/1471-2334-13-80.
7. Kitchel B, Sundin D R, Patel J B. 2009. Regional dissemination of KPC-producing *Klebsiella pneumoniae*. Antimicrob Agents Chemother 53:4511-4513.10.1128/AAC.00784-09.
8. Frasson I, Lavezzo E, Franchin E, Toppo S, Barzon L, Cavallaro A, Richter S N, Palu G. 2012. Antimicrobial treatment and containment measures for an extremely drug-resistant *Klebsiella pneumoniae* ST101 isolate carrying pKPN101-IT, a novel fully sequenced bla(KPC-2) plasmid. J Clin Microbiol 50:3768-3772.10.1128/JCM.01892-12.
9. Lascols C, Peirano G, Hackel M, Laupland K B, Pitout J D. 2013. Surveillance and molecular epidemiology of *Klebsiella pneumoniae* isolates that produce carbapenemases: first report of OXA-48-like enzymes in North America. Antimicrob Agents Chemother 57:130-136.10.1128/AAC.01686-12.
10. Bialek-Davenet S, Criscuolo A, Ailloud F, Passet V, Jones L, Delannoy-Vieillard A S, Garin B, Le Hello S, Arlet G, Nicolas-Chanoine M H, Decre D, Brisse S. 2014. Genomic definition of hypervirulent and multidrug-resistant *Klebsiella pneumoniae* clonal groups. Emerg Infect Dis 20:1812-1820.10.3201/eid2011.140206.
11. Nagasaka Y, Kimura K, Yamada K, Wachino J, Jin W, Notake S, Yanagisawa H, Arakawa Y. 2015. Genetic profiles of fluoroquinolone-nonsusceptible *Klebsiella pneumoniae* among cephalosporin-resistant *K. pneumoniae*. Microb Drug Resist 21:224-233.10.1089/mdr.2014.0150.
12. Liu Y, Wan L G, Deng Q, Cao X W, Yu Y, Xu Q F. 2015. First description of NDM-1-, KPC-2-, VIM-2- and IMP-4-producing *Klebsiella pneumoniae* strains in a single Chinese teaching hospital. Epidemiol Infect 143:376-384.10.1017/S0950268814000995.
13. Cubero M, Grau I, Tubau F, Pallares R, Dominguez M A, Linares J, Ardanuy C. 2016. Hypervirulent *Klebsiella pneumoniae* clones causing bacteraemia in adults in a teaching hospital in Barcelona, Spain (2007-2013). Clin Microbiol Infect 22:154-160.10.1016/j.cmi.2015.09.025.
14. Jacobson R K, Manesen M R, Moodley C, Smith M, Williams S G, Nicol M P, Bamford C M. 2015. Molecular characterisation and epidemiological investigation of an outbreak of blaOXA-181 carbapenemase-producing isolates of *Klebsiella pneumoniae* in South Africa. S Afr Med J 105:1030-1035.10.7196/SAMJ.2015.v105i12.9926.
15. Zhu J, Sun L, Ding B, Yang Y, Xu X, Liu W, Zhu D, Yang F, Zhang H, Hu F. 2016. Outbreak of NDM-1-producing *Klebsiella pneumoniae* ST76 and ST37 isolates in neonates. Eur J Clin Microbiol Infect Dis 10.1007/s10096-016-2578-z.
16. Viau R A, Hujer A M, Marshall S H, Perez F, Hujer K M, Briceno D F, Dul M, Jacobs M R, Grossberg R, Toltzis P, Bonomo R A. 2012. "Silent" dissemination of *Klebsiella pneumoniae* isolates bearing *K. pneumoniae* carbapenemase in a long-term care facility for children and young adults in northeast Ohio. Clin Infect Dis 54:1314-1321.10.1093/cid/cis036.
17. Bowers J R, Kitchel B, Driebe E M, MacCannell D R, Roe C, Lemmer D, de Man T, Rasheed J K, Engelthaler D M, Keim P, Limbago B M. 2015. Genomic analysis of the emergence and rapid global dissemination of the clonal group 258 *Klebsiella pneumoniae* pandemic. PLoS One 10:e0133727.10.1371/journal.pone.0133727.
18. Zheng R, Zhang Q, Guo Y, Feng Y, Liu L, Zhang A, Zhao Y, Yang X, Xia X. 2016. Outbreak of plasmid-mediated NDM-1-producing *Klebsiella pneumoniae* ST105 among neonatal patients in Yunnan, China. Ann Clin Microbiol Antimicrob 15:10.10.1186/s12941-016-0124-6.
19. Pena I, Picazo J J, Rodriguez-Avial C, Rodriguez-Avial I. 2014. Carbapenemase-producing Enterobacteriaceae in a tertiary hospital in Madrid, Spain: high percentage of colistin resistance among VIM-1-producing *Klebsiella pneumoniae* ST11 isolates. Int J Antimicrob Agents 43:460-464.10.1016/j.ijantimicag.2014.01.021.
20. Voulgari E, Gartzonika C, Vrioni G, Politi L, Priavali E, Levidiotou-Stefanou S, Tsakris A. 2014. The Balkan region: NDM-1-producing *Klebsiella pneumoniae* ST11 clonal strain causing outbreaks in Greece. J Antimicrob Chemother 69:2091-2097.10.1093/jac/dku105.
21. Woodford N, Turton J F, Livermore D M. 2011. Multiresistant Gram-negative bacteria: the role of high-risk clones in the dissemination of antibiotic resistance. FEMS Microbiol Rev 35:736-755.10.1111/j.1574-6976.2011.00268.x.
22. Swaminathan M, Sharma S, Poliansky Blash S, Patel G, Banach D B, Phillips M, LaBombardi V, Anderson K F, Kitchel B, Srinivasan A, Calfee D P. 2013. Prevalence and risk factors for acquisition of carbapenem-resistant Enterobacteriaceae in the setting of endemicity. Infect Control Hosp Epidemiol 34:809-817.10.1086/671270.
23. Pena C, Pujol M, Ardanuy C, Ricart A, Pallares R, Linares J, Ariza J, Gudiol F. 1998. Epidemiology and successful control of a large outbreak due to *Klebsiella pneumoniae* producing extended-spectrum beta-lactamases. Antimicrob Agents Chemother 42:53-58.
24. Tischendorf J, de Avila R A, Safdar N. 2016. Risk of infection following colonization with carbapenem-resistant Enterobactericeae [sic]: a systematic review. Am J Infect Control 44:539-543.10.1016/j.ajic.2015.12.005.
25. Amit S, Mishali H, Kotlovsky T, Schwaber M J, Carmeli Y. 2015. Bloodstream infections among carriers of carbapenem-resistant *Klebsiella pneumoniae*: etiology, incidence and predictors. Clin Microbiol Infect 21:30-34.10.1016/j.cmi.2014.08.001.
26. Thaden J T, Lewis S S, Hazen K C, Huslage K, Fowler V G, Jr, Moehring R W, Chen L F, Jones C D, Moore Z S, Sexton D J, Anderson D J. 2014. Rising rates of carbapenem-resistant enterobacteriaceae in community hospitals: a mixed-methods review of epidemiology and microbiology practices in a network of community hospitals in the southeastern United States. Infect Control Hosp Epidemiol 35:978-983.10.1086/677157.
27. Bassyouni R H, Gaber S N, Wegdan A A. 2015. Fecal carriage of extended-spectrum beta-lactamase- and AmpC-producing *Escherichia coli* among healthcare workers. J Infect Dev Ctries 9:304-308.10.3855/jidc.5633.
28. Papadimitriou-Olivgeris M, Marangos M, Fligou F, Christofidou M, Sklavou C, Vamvakopoulou S, Anastassiou E D, Filos K S. 2013. KPC-producing *Klebsiella pneumoniae* enteric colonization acquired during intensive care unit stay: the significance of risk factors for its 29. Monari C, Merlini L, Nardelli E, Cacioni M, Repetto A, Mencacci A, Vecchiarelli A. 2016. Carbapenem-resistant *Klebsiella pneumoniae*: results of a laboratory surveillance program in an Italian general hospital (August 2014-January 2015): surveillance of carbapenem-resistant *Klebsiella pneumoniae*. Adv Exp Med Biol 901:91-101.10.1007/5584_2015_5018.
30. Voor in't Holt A F, Severin J A, Goessens W H, Te Witt R, Vos M C. 2015. Instant typing is essential to detect transmission of extended-spectrum beta-lactamase-producing *Klebsiella* species. PLoS One 10:e0136135.10.1371/journal.pone.0136135.
31. Viau R, Frank K M, Jacobs M R, Wilson B, Kaye K, Donskey C J, Perez F, Endimiani A, Bonomo R A. 2016. Intestinal carriage of carbapenemase-producing organisms: current status of surveillance methods. Clin Microbiol Rev 29:1-27.10.1128/CMR.00108-14.
32. Lee B Y, Bartsch S M, Wong K F, McKinnell J A, Slayton R B, Miller L G, Cao C, Kim D S, Kallen A J, Jernigan J A, Huang S S. 2016. The potential trajectory of carbapenem-resistant Enterobacteriaceae, an emerging threat to health-care facilities, and the impact of the Centers for Disease Control and Prevention toolkit. Am J Epidemiol 183:471-479.10.1093/aje/kwv299.
33. Parker V A, Logan C K, Currie B. 2014. Carbapenem-resistant Enterobacteriaceae (CRE) control and prevention toolkit. Agency for Healthcare Research and Quality, Rockville, MD
34. Lucet J C, Decre D, Fichelle A, Joly-Guillou M L, Pernet M, Deblangy C, Kosmann M J, Regnier B. 1999. Control of a prolonged outbreak of extended-spectrum beta-lactamase-producing Enterobacteriaceae in a university hospital. Clin Infect Dis 29:1411-1418.10.1086/313511.
35. Schwaber M J, Carmeli Y. 2014. An ongoing national intervention to contain the spread of carbapenem-resistant enterobacteriaceae. Clin Infect Dis 58:697-703.10.1093/cid/cit795.
36. Hayden M K, Lin M Y, Lolans K, Weiner S, Blom D, Moore N M, Fogg L, Henry D, Lyles R, Thurlow C, Sikka M, Hines D, Weinstein R A, Centers for Disease Control and Prevention Epicenters Program. 2015. Prevention of colonization and infection by *Klebsiella pneumoniae* carbapenemase-producing Enterobacteriaceae in long-term acute-care hospitals. Clin Infect Dis 60:1153-1161.10.1093/cid/ciu1173.
37. Epson E E, Pisney L M, Wendt J M, MacCannell D R, Janelle S J, Kitchel B, Rasheed J K, Limbago B M, Gould C V, Kallen A J, Barron M A, Bamberg W M. 2014. Carbapenem-resistant *Klebsiella pneumoniae* producing New Delhi metallo-beta-lactamase at an acute care hospital, Colorado, 2012. Infect Control Hosp Epidemiol 35:390-397.10.1086/675607.
38. Pisney L M, Barron M A, Kassner E, Havens D, Madinger N E. 2014. Carbapenem-resistant Enterobacteriaceae rectal screening during an outbreak of New Delhi metallo-beta-lactamase-producing *Klebsiella pneumoniae* at an acute care hospital. Infect Control Hosp Epidemiol 35:434-436.10.1086/675597.
39. Dhar S, Martin E T, Lephart P R, McRoberts J P, Chopra T, Burger T T, Tal-Jasper R, Hayakawa K, Ofer-Friedman H, Lazarovitch T, Zaidenstein R, Perez F, Bonomo R A, Kaye K S, Marchaim D. 2016. Risk factors and outcomes for carbapenem-resistant *Klebsiella pneumoniae* isolation, stratified by its multilocus sequence typing: ST258 versus non-ST258. Open Forum Infect Dis 3:ofv213.10.1093/ofid/ofv213.
40. Wendt J M, Kaul D, Limbago B M, Ramesh M, Cohle S, Denison A M, Driebe E M, Rasheed J K, Zaki S R, Blau D M, Paddock C D, McDougal L K, Engelthaler D M, Keim P S, Roe C C, Akselrod H, Kuehnert M J, Basavaraju S V. 2014. Transmission of methicillin-resistant *Staphylococcus aureus* infection through solid organ transplantation: confirmation via whole genome sequencing. Am J Transplant 14:2633-2639.10.1111/ajt.12898.
41. Snitkin E S, Zelazny A M, Thomas P J, Stock F, NISC Comparative Sequencing Program Group, Henderson D K, Palmore T N, Segre J A. 2012. Tracking a hospital outbreak of carbapenem-resistant *Klebsiella pneumoniae* with whole-genome sequencing. Sci Transl Med 4:148ra116.10.1126/scitranslmed.3004129.
42. Iqbal S, Quigley E M. 2016. Progress in our understanding of the gut microbiome: implications for the clinician. Curr Gastroenterol Rep 18:49.10.1007/s11894-016-0524-y.
43. Cope E K, Lynch S V. 2015. Novel microbiome-based therapeutics for chronic rhinosinusitis. Curr Allergy Asthma Rep 15:504.10.1007/s11882-014-0504-y.
44. Millares L, Perez-Brocal V, Ferrari R, Gallego M, Pomares X, Garcia-Nunez M, Monton C, Capilla S, Monso E, Moya A. 2015. Functional metagenomics of the bronchial microbiome in COPD. PLoS One 10:e0144448.10.1371/journal.pone.0144448.
45. Colman R E, Anderson J, Lehmkuhl E, Lemmer D, Heaton H, Georghiou S B, Wiggins K, Crudu V, Cohen T, Rodwell T C, Engelthaler D M. 2016. Rapid drug susceptibility testing of drug resistant *Mycobacterium tuberculosis* directly from clinical samples by use of amplicon sequencing: a proof-of-concept study. J Clin Microbiol 54:2058-2067.10.1128/JCM.00535-16.
46. Laine S. 2013. FDA allows marketing of four "next generation" gene sequencing devices. U.S. Food and Drug Administration, Silver Spring, MD
47. Gilbert J A, Meyer F, Jansson J, Gordon J, Pace N, Tiedje J, Ley R, Fierer N, Field D, Kyrpides N, Glockner F O, Klenk H P, Wommack K E, Glass E, Docherty K, Gallery R, Stevens R, Knight R. 2010. The Earth Microbiome Project: meeting report of the "1 EMP Meeting on Sample Selection and Acquisition" at Argonne National Laboratory Oct. 6, 2010. Stand Genomic Sci 3:249-253.10.4056/aigs.1443528.
48. Sahl J W, Lemmer D, Travis J, Schupp J, Gillece J, Aziz M, Driebe E, Drees K, Hicks N, Williamson C, Hepp C, Smith D, Roe C, Engelthaler D, Wagner D, Keim P. 2016. The northern Arizona SNP pipeline (NASP): accurate, flexible, and rapid identification of SNPs in WGS datasets. bioRxiv 10.1101/037267.
49. McKenna A, Hanna M, Banks E, Sivachenko A, Cibulskis K, Kernytsky A, Garimella K, Altshuler D, Gabriel S, Daly M, DePristo M A. 2010. The Genome Analysis Toolkit: a MapReduce framework for analyzing next-generation DNA sequencing data. Genome Res 20:1297-1303.10.1101/gr.107524.110.
50. Tamura K, Stecher G, Peterson D, Filipski A, Kumar S. 2013. MEGA6: Molecular evolutionary genetics analysis version 6.0. Mol Biol Evol 30:2725-2729.10.1093/molbev/mst197.
51. Letunic I, Bork P. 2011. Interactive Tree Of Life v2: online annotation and display of phylogenetic trees made easy. Nucleic Acids Res 39:W475-478.10.1093/nar/gkr201.

52. Bankevich A, Nurk S, Antipov D, Gurevich A A, Dvorkin M, Kulikov A S, Lesin V M, Nikolenko S I, Pham S, Prjibelski A D, Pyshkin A V, Sirotkin A V, Vyahhi N, Tesler G, Alekseyev M A, Pevzner P A. 2012. SPAdes: a new genome assembly algorithm and its applications to single-cell sequencing. J Comput Biol 19:455-477.10.1089/cmb.2012.0021.

53. Sahl J W, Caporaso J G, Rasko D A, Keim P. 2014. The large-scale blast score ratio (LS-BSR) pipeline: a method to rapidly compare genetic content between bacterial genomes. PeerJ 2:e332.10.7717/peerj.332.

54. Holt K E, Wertheim H, Zadoks R N, Baker S, Whitehouse C A, Dance D, Jenney A, Connor T R, Hsu L Y, Severin J, Brisse S, Cao H, Wilksch J, Gorrie C, Schultz M B, Edwards D J, Nguyen K V, Nguyen T V, Dao T T, Mensink M, Minh V L, Nhu N T, Schultsz C, Kuntaman K, Newton P N, Moore C E, Strugnell R A, Thomson N R. 2015. Genomic analysis of diversity, population structure, virulence, and antimicrobial resistance in *Klebsiella pneumoniae*, an urgent threat to public health. Proc Natl Acad Sci USA 112:E3574-3581.10.1073/pnas.1501049112.

55. Brisse S, Passet V, Haugaard A B, Babosan A, Kassis-Chikhani N, Struve C, Decre D. 2013. wzi Gene sequencing, a rapid method for determination of capsular type for *Klebsiella* strains. J Clin Microbiol 51:4073-4078.10.1128/JCM.01924-13.

56. Colman R E, Schupp J M, Hicks N D, Smith D E, Buchhagen J L, Valafar F, Crudu V, Romancenco E, Noroc E, Jackson L, Catanzaro D G, Rodwell T C, Catanzaro A, Keim P, Engelthaler D M. 2015. Detection of low-level mixed-population drug resistance in *Mycobacterium tuberculosis* using high fidelity amplicon sequencing. PLoS One 10:e0126626.10.1371/journal.pone.0126626.

57. Bolger A M, Lohse M, Usadel B. 2014. Trimmomatic: a flexible trimmer for Illumina sequence data. Bioinformatics 30:2114-2120.10.1093/bioinformatics/btu170.

58. Langmead B, Salzberg S L. 2012. Fast gapped-read alignment with Bowtie 2. Nat Methods 9:357-359.10.1038/nmeth.1923.

59. Li H, Durbin R. 2009. Fast and accurate short read alignment with Burrows-Wheeler transform. Bioinformatics 25:1754-1760.10.1093/bioinformatics/btp324.

60. Milne I, Stephen G, Bayer M, Cock P J, Pritchard L, Cardle L, Shaw P D, Marshall D. 2013. Using Tablet for visual exploration of second-generation sequencing data. Brief Bioinform 14:193-202.10.1093/bib/bbs012.

61. Inouye M, Dashnow H, Raven L A, Schultz M B, Pope B J, Tomita T, Zobel J, Holt K E. 2014. SRST2: rapid genomic surveillance for public health and hospital microbiology labs. Genome Med 6:90.10.1186/s13073-014-0090-6.

62. Li J J, Munoz-Price L S, Spychala C N, DePascale D, Doi Y. 2016. New Delhi metallo-beta-lactamase-1-producing *Klebsiella pneumoniae*, Florida, USA(1). Emerg Infect Dis 22:744-746.10.3201/eid2204.151176.

63. Shon A S, Bajwa R P, Russo T A. 2013. Hypervirulent (hypermucoviscous) *Klebsiella pneumoniae*: a new and dangerous breed. Virulence 4:107-118.10.4161/viru.22718.

64. Davis G S, Waits K, Nordstrom L, Weaver B, Aziz M, Gauld L, Grande H, Bigler R, Horwinski J, Porter S, Stegger M, Johnson J R, Liu C M, Price L B. 2015. Intermingled *Klebsiella pneumoniae* populations between retail meats and human urinary tract infections. Clin Infect Dis 61:892-899.10.1093/cid/civ428.

65. Ocampo A M, Chen L, Cienfuegos A V, Roncancio G, Chavda K D, Kreiswirth B N, Jimenez J N. 2016. A two-year surveillance in five Colombian tertiary care hospitals reveals high frequency of non-CG258 clones of carbapenem-resistant *Klebsiella pneumoniae* with distinct clinical characteristics. Antimicrob Agents Chemother 60:332-342.10.1128/AAC.01775-15.

66. Wachino J, Shibayama K, Kurokawa H, Kimura K, Yamane K, Suzuki S, Shibata N, Ike Y, Arakawa Y. 2007. Novel plasmid-mediated 16S rRNA m1A1408 methyltransferase, NpmA, found in a clinically isolated *Escherichia coli* strain resistant to structurally diverse aminoglycosides. Antimicrob Agents Chemother 51:4401-4409.10.1128/AAC.00926-07.

67. Scott R D, I I. 2009. The direct medical costs of healthcare-associated infections in U.S. hospitals and the benefits of prevention. Centers for Disease Control and Prevention, Atlanta, GA 68. Patel T S, Nagel J L. 2015. Clinical outcomes of Enterobacteriaceae infections stratified by carbapenem MICs. J Clin Microbiol 53:201-205.10.1128/JCM.03057-14.

69. Daroukh A, Delaunay C, Bigot S, Ceci J M, Siddhoun N, Bukreyeva I, Raisin J, Porcheret H, Maisonneuve L, Bouldouyre M A. 2014. Characteristics and costs of carbapenemase-producing enterobacteria carriers (2012/2013). Med Mal Infect 44:321-326.10.1016/j.medmal.2014.06.004.

70. van Duin D, Cober E, Richter S S, Perez F, Kalayjian R C, Salata R A, Evans S, Fowler V G, Jr, Kaye K S, Bonomo R A. 2015. Impact of therapy and strain type on outcomes in urinary tract infections caused by carbapenem-resistant *Klebsiella pneumoniae*. J Antimicrob Chemother 70:1203-1211.10.1093/jac/dku495.

71. Sahl J W, Sistrunk J R, Fraser C M, Hine E, Baby N, Begum Y, Luo Q, Sheikh A, Qadri F, Fleckenstein J M, Rasko D A. 2015. Examination of the enterotoxigenic *Escherichia coli* population structure during human infection. mBio 6:e00501-15.10.1128/mBio.00501-15.

72. Stoesser N, Sheppard A E, Moore C E, Golubchik T, Parry C M, Nget P, Saroeun M, Day N P, Giess A, Johnson J R, Peto T E, Crook D W, Walker A S, Modernizing Medical Microbiology Informatics Group. 2015. Extensive within-host diversity in fecally carried extended-spectrum-beta-lactamase-producing *Escherichia coli* isolates: implications for transmission analyses. J Clin Microbiol 53:2122-2131.10.1128/JCM.00378-15.

73. Lin M Y, Lyles-Banks R D, Lolans K, Hines D W, Spear J B, Petrak R, Trick W E, Weinstein R A, Hayden M K, Centers for Disease Control and Prevention Epicenters Program. 2013. The importance of long-term acute care hospitals in the regional epidemiology of *Klebsiella pneumoniae* carbapenemase-producing Enterobacteriaceae. Clin Infect Dis 57:1246-1252.10.1093/cid/cit500.

74. Janvier F, Delacour H, Tesse S, Larreche S, Sanmartin N, Ollat D, Rapp C, Merens A. 2014. Faecal carriage of extended-spectrum beta-lactamase-producing enterobacteria among soldiers at admission in a French military hospital after aeromedical evacuation from overseas. Eur J Clin Microbiol Infect Dis 33:1719-1723.10.1007/s10096-014-2141-8.

75. Allyn J, Angue M, Belmonte O, Lugagne N, Traversier N, Vandroux D, Lefort Y, Allou N. 2015. Delayed diagnosis of high drug-resistant microorganisms carriage in repatriated patients: three cases in a French intensive care unit. J Travel Med 22:215-217.10.1111/jtm.12194.

76. Bart Y, Paul M, Eluk O, Geffen Y, Rabino G, Hussein K. 2015. Risk factors for recurrence of carbapenem-resistant Enterobacteriaceae carriage: case-control study. Infect Control Hosp Epidemiol 36:936-941.10.1017/ice.2015.82.
77. Kim K R, Lee J Y, Park H Y, Kwak S H, Lim Y J, Hong M J, Kim S K, Park S Y, Kim H J, Choi H S, Kim M N, Choi H R, Jeong J S, Choi S H. 2015. Clearance rate of carbapenemase-producing Enterobacteriaceae carriage among hospitalized patients. Infect Control Hosp Epidemiol 36:1361-1362.10.1017/ice.2015.169.
78. Torres-Gonzalez P, Cervera-Hernandez M E, Niembro-Ortega M D, Leal-Vega F, Cruz-Hervert L P, Garcia-Garcia L, Galindo-Fraga A, Martinez-Gamboa A, Bobadilla-Del Valle M, Sifuentes-Osornio J, Ponce-de-Leon A. 2015. Factors associated to prevalence and incidence of carbapenem-resistant Enterobacteriaceae fecal carriage: a cohort study in a Mexican tertiary care hospital. PLoS One 10:e0139883.10.1371/journal.pone.0139883.
79. Gagliotti C, Ciccarese V, Sarti M, Giordani S, Barozzi A, Braglia C, Gallerani C, Gargiulo R, Lenzotti G, Manzi O, Martella D, Moro M L. 2013. Active surveillance for asymptomatic carriers of carbapenemase-producing *Klebsiella pneumoniae* in a hospital setting. J Hosp Infect 83:330-332.10.1016/j.jhin.2012.11.024.
80. Ludden C, Cormican M, Vellinga A, Johnson J R, Austin B, Morris D. 2015. Colonisation with ESBL-producing and carbapenemase-producing Enterobacteriaceae, vancomycin-resistant enterococci, and meticillin-resistant *Staphylococcus aureus* in a long-term care facility over one year. BMC Infect Dis 15:168.10.1186/s12879-015-0880-5.
81. Armand-Lefevre L, Angebault C, Barbier F, Hamelet E, Defrance G, Ruppe E, Bronchard R, Lepeule R, Lucet J C, El Mniai A, Wolff M, Montravers P, Plesiat P, Andremont A. 2013. Emergence of imipenem-resistant Gram-negative bacilli in intestinal flora of intensive care patients. Antimicrob Agents Chemother 57:1488-1495.10.1128/AAC.01823-12.
82. Prasad N, Labaze G, Kopacz J, Chwa S, Platis D, Pan C X, Russo D, LaBombardi V J, Osorio G, Pollack S, Kreiswirth B N, Chen L, Urban C, Segal-Maurer S. 2016. Asymptomatic rectal colonization with carbapenem-resistant Enterobacteriaceae and *Clostridium difficile* among residents of a long-term care facility in New York City. Am J Infect Control 44:525-532.10.1016/j.ajic.2015.11.021.
83. Breurec S, Melot B, Hoen B, Passet V, Schepers K, Bastian S, Brisse S. 2016. Liver abscess caused by infection with community-acquired *Klebsiella* quasipneumoniae subsp. quasipneumoniae. Emerg Infect Dis 22:529-531.10.3201/eid2203.151466.
84. Maatallah M, Vading M, Kabir M H, Bakhrouf A, Kalin M, Naucler P, Brisse S, Giske C G. 2014. *Klebsiella variicola* is a frequent cause of bloodstream infection in the Stockholm area, and associated with higher mortality compared to *K. pneumoniae*. PLoS One 9:e113539.10.1371/journal.pone.0113539.
85. Sichtig H. 2016. Infectious disease next generation sequencing based diagnostic devices: microbial identification and detection of antimicrobial resistance and virulence markers, draft guidance for industry and Food and Drug Administration staff. Division of Microbiology Devices, U.S. Food and Drug Administration, Rockville, MD

---

What is claimed is:

1. A method of detecting *Klebsiella pneumoniae* within a sample from a subject, the method comprising:

selecting one or more primer pairs, wherein the one or more primer pairs comprises a first primer and a second primer, each consisting of a universal tail sequence and a *Klebsiella pneumoniae* specific sequence, and wherein the *Klebsiella pneumoniae* specific sequence of the first primer consists of SEQ ID NO: 1 and the *Klebsiella pneumoniae* specific sequence of the second primer consists of SEQ ID NO: 2;

subjecting DNA, RNA, or both from the sample to a PCR amplification reaction using the one or more primer pairs; and detecting the *Klebsiella pneumoniae* by detecting amplification products resulting from the PCR amplification reaction, wherein the amplification products resulting from the PCR amplification reaction are detected by next-generation sequencing (NGS), wherein *Klebsiella pneumoniae* is detected if the amplicon sequences are greater than or equal to 90% identical to a *Klebsiella pneumoniae* reference sequence.

2. The method of claim 1, wherein the PCR amplification reaction is a multiplex amplification reaction.

3. The method of claim 1, wherein the subject has pneumonia, and the method further comprises treating the subject with an aminoglycoside, cephalosporin, or both upon detection of the *Klebsiella pneumoniae*.

4. A composition for detecting *Klebsiella pneumoniae* comprising:

a primer pair, wherein the primer pair comprises a first primer and a second primer, each consisting of a universal tail sequence and a *Klebsiella pneumoniae* specific sequence, wherein the *Klebsiella pneumoniae* specific sequence of the first primer consists of SEQ ID NO: 1 and the *Klebsiella pneumoniae* specific sequence of the second primer consists of SEQ ID NO: 2, and the universal tail sequence of the first primer consists of SEQ ID NO: 282 and the universal tail sequence of the second primer consists of SEQ ID NO: 283; and a nucleotide polymerase, buffer, diluent, excipient, or combinations thereof.

5. A composition for detecting *Klebsiella pneumoniae* comprising a primer pair, wherein the primer pair comprises a first primer and a second primer, each consisting of a universal tail sequence and a *Klebsiella pneumoniae* specific sequence, wherein the *Klebsiella pneumoniae* specific sequence of the first primer consists of SEQ ID NO: 1 and the *Klebsiella pneumoniae* specific sequence of the second primer consists of SEQ ID NO: 2, and the universal tail sequence of the first primer consists of SEQ ID NO: 282 and the universal tail sequence of the second primer consists of SEQ ID NO: 283.

6. The method of claim 1, wherein *Klebsiella pneumoniae* is detected if the amplicon sequences are greater than or equal to 97% identical to a *Klebsiella pneumoniae* reference sequence.

7. The method of claim 1, wherein *Klebsiella pneumoniae* is detected if the amplicon sequences include 10 or less single nucleotide polymorphisms (SNPs) as compared to a *Klebsiella pneumoniae* reference sequence.

* * * * *

SEQUENCE LISTING

<160> NUMBER OF SEQ ID NOS: 285

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cgttcctcac cgtagtgg                                                 18

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
tccagcgtga cataatcgg                                                19

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tgcctatcgc cactttattg a                                             21

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
cggtcgttaa tcgccttct                                                    19

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ccgtcgccgt attactgat                                                    19

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tctctacaac acgctaccct a                                                 21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
tcagctatcg cctggagtgc ta                                                22

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctgctcctgg ccgacaaac                                                    19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gccataatgc agcctttgc                                                    19

<210> SEQ ID NO 10
<211> LENGTH: 21
<212> TYPE: DNA
<213> ORGANISM: Artificial Sequence
<220> FEATURE:

<223> OTHER INFORMATION: Primer

<400> SEQUENCE: 10
atcgcgtgaa cgtcagcttc t                                                21

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
gcagccgtac agaccga                                                     17

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
cyattcgcca gcaggacta                                                   19

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gggatcgast tcacgtccac                                                  20

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
acgccgaggg acargagm                                                    18

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gcagatttaa ccgagctggt ct                                               22

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
agagcgatgg cgaagaga                                                    18

```
<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
cgacaaccgc ttcgctacc                                              19

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
agyaccgggc gcagattg                                               18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
gmacgccgac gtcatyct                                               18

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
cagtgcttgc atagtgtcct ctt                                         23

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cggtggtgtt tgtctgaacg                                             20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
caggtgcgga tcttgtcaat g                                           21

<210> SEQ ID NO 23
<211> LENGTH: 22
<212> TYPE: DNA
<213> ORGANISM: Artificial Sequence
<220> FEATURE:
<223> OTHER INFORMATION: Primer
```

```
<400> SEQUENCE: 23
tctttgatct tgtccgggtt ga                                              22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cctcggcgat atggacttca                                                 20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
gctrccgttg acctttattg c                                               21

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gccgaagcgt tcatagaaat cc                                              22

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ggcattggcg tcaataaagc                                                 20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
atagccgcca gacgaattac ca                                              22

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
tcgacaacat cgtcgtcttt c                                               21

<210> SEQ ID NO 30
<211> LENGTH: 20
```

```
<212> TYPE: DNA
<213> ORGANISM: Artificial Sequence
<220> FEATURE:
<223> OTHER INFORMATION: Primer

<400> SEQUENCE: 30
tgctgcacag cactcgtaag                                               20

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gacgatgtyg atgtggcgat t                                             21

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
acgccctgcc cgtgaatg                                                 18

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gtcgtctggt tcggtcattc                                               20

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
ggtgtacagc gaggtcataa agg                                           23

<210> SEQ ID NO 35
<211> LENGTH: 17
<212> TYPE: DNA
<213> ORGANISM: Artificial Sequence
<220> FEATURE:
<223> OTHER INFORMATION: Primer

<400> SEQUENCE: 35
gcaggcatgg agcgtgt                                                  17

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
```
gcttcggcag taaaccgtaa                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cccgttggcc atcgtatgtc                                               20

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
gagcgcatag aagtgaccat tc                                            22

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
ctcyagcacg atgtcgtaag g                                             21

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gcgagcatcg ygagattagy g                                             21

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
gcccaaagca tggtctatga ac                                            22

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
cgcacgtcgg ttatttggtt g                                             21

<210> SEQ ID NO 43
<211> LENGTH: 16
<212> TYPE: DNA
<213> ORGANISM: Artificial Sequence

```
<220> FEATURE:
<223> OTHER INFORMATION: Primer

<400> SEQUENCE: 43
ggrcccagct atgtgc                                                    16

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ccaccattcr atgcttgctt t                                              21

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45
accggctcgt cgcctttc                                                  18

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
tcacaccagc ccatatacca                                                20

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
gcttcgcatt ctggtagctg t                                              21

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
caactcggcr ctgttcgt                                                  18

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tagccgctct tgttgatgga                                                20
```

```
<210> SEQ ID NO 50
<211> LENGTH: 17
<212> TYPE: DNA
<213> ORGANISM: Artificial Sequence
<220> FEATURE:
<223> OTHER INFORMATION: Primer

<400> SEQUENCE: 50
acgctgtgga cgcagta                                                      17

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
atacccggcg gaagayct                                                     18

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
agggccagca tcgctttcag                                                   20

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
cagccaggac gctttcgtta g                                                 21

<210> SEQ ID NO 54
<211> LENGTH: 17
<212> TYPE: DNA
<213> ORGANISM: Artificial Sequence
<220> FEATURE:
<223> OTHER INFORMATION: Primer

<400> SEQUENCE: 54
tcggcgttga ggttrct                                                      17

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
ccagcaactg cgctttgtc                                                    19

<210> SEQ ID NO 56
<211> LENGTH: 21
<212> TYPE: DNA
<213> ORGANISM: Artificial Sequence
<220> FEATURE:
<223> OTHER INFORMATION: Primer
```

-continued

<400> SEQUENCE: 56
cgtctggagc atggaagatg a           21

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
cgttctcagc agttcgattt catct           25

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
cgccgataag cagtcgct           18

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
ccgatggcga caaataaacc a           21

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gcagtggaag aggctctgta           20

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
caacccggcg cactttc           17

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
cgcgtccaga cgatatcttt g           21

<210> SEQ ID NO 63

```
<211> LENGTH: 25
<212> TYPE: DNA
<213> ORGANISM: Artificial Sequence
<220> FEATURE:
<223> OTHER INFORMATION: Primer

<400> SEQUENCE: 63 ttacagaat ggcagagaag aaagg                                          25

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
gtggcggcgt ttacaaatca g                                             21

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gagctgaccg aagagttcat ca                                            22

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gcagttccag agcctgtttc                                               20

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
atggtggtgc gccagtg                                                  17

<210> SEQ ID NO 68
<211> LENGTH: 18
<212> TYPE: DNA
<213> ORGANISM: Artificial Sequence
<220> FEATURE:
<223> OTHER INFORMATION: Primer

<400> SEQUENCE: 68
gctgaccgag acgttgtc                                                 18

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
```

-continued tcagtttgcc agtctcggtt t                                                  21

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
gcgtctggcg taagaggta                                                     19

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
gatcagatcc aacgggcaga ag                                                 22

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
ttgcgcgctt aatcattgc                                                     19

<210> SEQ ID NO 73
<211> LENGTH: 19
<212> TYPE: DNA
<213> ORGANISM: Artificial Sequence
<220> FEATURE:
<223> OTHER INFORMATION: Primer

<400> SEQUENCE: 73
gctgacctgc gggttgttt                                                     19

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gccacgatct tcctgctgaa                                                    20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
tcgagccggt ttgttcatcg                                                    20

<210> SEQ ID NO 76
<211> LENGTH: 20
<212> TYPE: DNA

```
<213> ORGANISM: Artificial Sequence
<220> FEATURE:
<223> OTHER INFORMATION: Primer

<400> SEQUENCE: 76
ccggactaca ggacactaca                                              20

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
gacagtcacc cttacctact acc                                          23

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
caggtggccg gattaaactc                                              20

<210> SEQ ID NO 79
<211> LENGTH: 19
<212> TYPE: DNA
<213> ORGANISM: Artificial Sequence
<220> FEATURE:
<223> OTHER INFORMATION: Primer

<400> SEQUENCE: 79
catgcaggga gaaggcaaa                                               19

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
acccaggcga agcgatgttc                                              20

<210> SEQ ID NO 81
<211> LENGTH: 17
<212> TYPE: DNA
<213> ORGANISM: Artificial Sequence
<220> FEATURE:
<223> OTHER INFORMATION: Primer

<400> SEQUENCE: 81
ccctttgggc ggcrcat                                                 17

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
aacgctcagg cggaagac                                                18
```

<210> SEQ ID NO 83
<211> LENGTH: 22
<212> TYPE: DNA
<213> ORGANISM: Artificial Sequence
<220> FEATURE:
<223> OTHER INFORMATION: Primer

<400> SEQUENCE: 83
cgaccatgat atggcggtgt tc                                              22

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
tgaccgcgcc tttacgat                                                   18

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
cgtctagttc tgctgtcttg t                                               21

<210> SEQ ID NO 86
<211> LENGTH: 18
<212> TYPE: DNA
<213> ORGANISM: Artificial Sequence
<220> FEATURE:
<223> OTHER INFORMATION: Primer

<400> SEQUENCE: 86
accgtcatgc ctgttgtc                                                   18

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
ttgttgattg gctaaaggga aac                                             23

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
cagacgacgg catagtcatt                                                 20

<210> SEQ ID NO 89
<211> LENGTH: 19
<212> TYPE: DNA
<213> ORGANISM: Artificial Sequence
<220> FEATURE:

```
<223> OTHER INFORMATION: Primer

<400> SEQUENCE: 89
ggacaagatg ggcggtatg                                                  19

<210> SEQ ID NO 90
<211> LENGTH: 17
<212> TYPE: DNA
<213> ORGANISM: Artificial Sequence
<220> FEATURE:
<223> OTHER INFORMATION: Primer

<400> SEQUENCE: 90
cggcgtagtg ctcagtg                                                    17

<210> SEQ ID NO 91
<211> LENGTH: 21
<212> TYPE: DNA
<213> ORGANISM: Artificial Sequence
<220> FEATURE:
<223> OTHER INFORMATION: Primer

<400> SEQUENCE: 91
caactggatc aagcaggaga t                                               21

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
cgacaacgca ttggcataag                                                 20

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
ggcggcgttg atgtcctt                                                   18

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ggcacaacca ccgtatagca                                                 20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
cgcacaacca ccatagagca                                                 20
```

```
<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
tggctcgayg gtggtattcg                                               20

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
ggctcgatgg cggcattc                                                 18

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gacccaccag ccaatcttag                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
gacccaccaa ccgatctgag                                               20

<210> SEQ ID NO 100
<211> LENGTH: 19
<212> TYPE: DNA
<213> ORGANISM: Artificial Sequence
<220> FEATURE:
<223> OTHER INFORMATION: Primer

<400> SEQUENCE: 100
ccgtcacgct gttgttagg                                                19

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
cgctcatcag cacgataaag t                                             21

<210> SEQ ID NO 102
<211> LENGTH: 19
<212> TYPE: DNA
<213> ORGANISM: Artificial Sequence
<220> FEATURE:
<223> OTHER INFORMATION: Primer
```

```
<400> SEQUENCE: 102
gacgatgtca ctggctgag                                                 19

<210> SEQ ID NO 103
<211> LENGTH: 18
<212> TYPE: DNA
<213> ORGANISM: Artificial Sequence
<220> FEATURE:
<223> OTHER INFORMATION: Primer

<400> SEQUENCE: 103
ccacaaccca ggaagcag                                                  18

<210> SEQ ID NO 104
<211> LENGTH: 18
<212> TYPE: DNA
<213> ORGANISM: Artificial Sequence
<220> FEATURE:
<223> OTHER INFORMATION: Primer

<400> SEQUENCE: 104
tggcgcagac cctgaaaa                                                  18

<210> SEQ ID NO 105
<211> LENGTH: 21
<212> TYPE: DNA
<213> ORGANISM: Artificial Sequence
<220> FEATURE:
<223> OTHER INFORMATION: Primer

<400> SEQUENCE: 105
atatcgttgg tggtgccata a                                              21

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
atggcgcaga ccctgaaa                                                  18

<210> SEQ ID NO 107
<211> LENGTH: 18
<212> TYPE: DNA
<213> ORGANISM: Artificial Sequence
<220> FEATURE:
<223> OTHER INFORMATION: Primer

<400> SEQUENCE: 107
ccgctgccgg ttttatcg                                                  18

<210> SEQ ID NO 108
<211> LENGTH: 18
<212> TYPE: DNA
<213> ORGANISM: Artificial Sequence
<220> FEATURE:
<223> OTHER INFORMATION: Primer

<400> SEQUENCE: 108
gagccgacgc tcaacacc                                                  18

<210> SEQ ID NO 109
<211> LENGTH: 18
```

-continued

<212> TYPE: DNA
<213> ORGANISM: Artificial Sequence
<220> FEATURE:
<223> OTHER INFORMATION: Primer

<400> SEQUENCE: 109
cccgacaacc cacgatgt                                                18

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
gctcaacacc gcgatccc                                                18

<210> SEQ ID NO 111
<211> LENGTH: 18
<212> TYPE: DNA
<213> ORGANISM: Artificial Sequence
<220> FEATURE:
<223> OTHER INFORMATION: Primer

<400> SEQUENCE: 111
cccgacaacc cacgatgt                                                18

<210> SEQ ID NO 112
<211> LENGTH: 19
<212> TYPE: DNA
<213> ORGANISM: Artificial Sequence
<220> FEATURE:
<223> OTHER INFORMATION: Primer

<400> SEQUENCE: 112
ttcgtctgga tcgcactga                                               19

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
gatgattctc gccgctgaag                                              20

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
cgctggttct ggtgaccta                                               19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
gatgattctc gccgctgaag                                                 20

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
ggtgcagctt agcgacaatg                                                 20

<210> SEQ ID NO 117
<211> LENGTH: 22
<212> TYPE: DNA
<213> ORGANISM: Artificial Sequence
<220> FEATURE:
<223> OTHER INFORMATION: Primer

<400> SEQUENCE: 117
ctcccgtttg gtttccgatc ag                                              22

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
caatgactgg aacaaagcct                                                 20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
cgatggaacc aaagttaccc                                                 20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
cagcgcgaaa ttcaaaaagt                                                 20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
gcgaaagatt tgggatcgtc                                                 20

<210> SEQ ID NO 122
<211> LENGTH: 20
<212> TYPE: DNA
<213> ORGANISM: Artificial Sequence

```
<220> FEATURE:
<223> OTHER INFORMATION: Primer

<400> SEQUENCE: 122
gatttgagyg acagccgttt                                              20

<210> SEQ ID NO 123
<211> LENGTH: 23
<212> TYPE: DNA
<213> ORGANISM: Artificial Sequence
<220> FEATURE:
<223> OTHER INFORMATION: Primer

<400> SEQUENCE: 123
gcagaagtac atcttatggc tga                                          23

<210> SEQ ID NO 124
<211> LENGTH: 24
<212> TYPE: DNA
<213> ORGANISM: Artificial Sequence
<220> FEATURE:
<223> OTHER INFORMATION: Primer

<400> SEQUENCE: 124
gctaatttct cacaggcaaa cttt                                         24

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
acaacccgta atgtaagcag ag                                           22

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
cgacaggaat agcttggaag g                                            21

<210> SEQ ID NO 127
<211> LENGTH: 21
<212> TYPE: DNA
<213> ORGANISM: Artificial Sequence
<220> FEATURE:
<223> OTHER INFORMATION: Primer

<400> SEQUENCE: 127
ccagttatca cagtgccatt c                                            21

<210> SEQ ID NO 128
<211> LENGTH: 21
<212> TYPE: DNA
<213> ORGANISM: Artificial Sequence
<220> FEATURE:
<223> OTHER INFORMATION: Primer

<400> SEQUENCE: 128
gtgctaactt gcgtgatacg a                                            21
```

```
<210> SEQ ID NO 129
<211> LENGTH: 26
<212> TYPE: DNA
<213> ORGANISM: Artificial Sequence
<220> FEATURE:
<223> OTHER INFORMATION: Primer

<400> SEQUENCE: 129
tccatattgg cataggaaag attaca                                          26

<210> SEQ ID NO 130
<211> LENGTH: 26
<212> TYPE: DNA
<213> ORGANISM: Artificial Sequence
<220> FEATURE:
<223> OTHER INFORMATION: Primer

<400> SEQUENCE: 130
tccatattgg cataagacag gttaca                                          26

<210> SEQ ID NO 131
<211> LENGTH: 22
<212> TYPE: DNA
<213> ORGANISM: Artificial Sequence
<220> FEATURE:
<223> OTHER INFORMATION: Primer

<400> SEQUENCE: 131
cgacgttcag tggttcrgat ct                                              22

<210> SEQ ID NO 132
<211> LENGTH: 18
<212> TYPE: DNA
<213> ORGANISM: Artificial Sequence
<220> FEATURE:
<223> OTHER INFORMATION: Primer

<400> SEQUENCE: 132
gckgctcgcc agtcgaaa                                                   18

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
accaatctaa gctacgccaa ctt                                             23

<210> SEQ ID NO 134
<211> LENGTH: 19
<212> TYPE: DNA
<213> ORGANISM: Artificial Sequence
<220> FEATURE:
<223> OTHER INFORMATION: Primer

<400> SEQUENCE: 134
cctgagttcc catccagcg                                                  19

<210> SEQ ID NO 135
<211> LENGTH: 24
<212> TYPE: DNA
<213> ORGANISM: Artificial Sequence
<220> FEATURE:
<223> OTHER INFORMATION: Primer
```

```
<400> SEQUENCE: 135
cgcatatatc accaatacca actt                                          24

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
gttccaggak caacgatgcc                                               20

<210> SEQ ID NO 137
<211> LENGTH: 21
<212> TYPE: DNA
<213> ORGANISM: Artificial Sequence
<220> FEATURE:
<223> OTHER INFORMATION: Primer

<400> SEQUENCE: 137
cccagtcgta cgttgctctt g                                             21

<210> SEQ ID NO 138
<211> LENGTH: 21
<212> TYPE: DNA
<213> ORGANISM: Artificial Sequence
<220> FEATURE:
<223> OTHER INFORMATION: Primer

<400> SEQUENCE: 138
gctcagtcgt acattgcact c                                             21

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139
cctggcgtgt ttgaaccatg tac                                           23

<210> SEQ ID NO 140
<211> LENGTH: 18
<212> TYPE: DNA
<213> ORGANISM: Artificial Sequence
<220> FEATURE:
<223> OTHER INFORMATION: Primer

<400> SEQUENCE: 140
cgcgtcgaac aggtagca                                                 18

<210> SEQ ID NO 141
<211> LENGTH: 21
<212> TYPE: DNA
<213> ORGANISM: Artificial Sequence
<220> FEATURE:
<223> OTHER INFORMATION: Primer

<400> SEQUENCE: 141
cggtgggtga cgtatgagat g                                             21

<210> SEQ ID NO 142
```

```
<211> LENGTH: 22
<212> TYPE: DNA
<213> ORGANISM: Artificial Sequence
<220> FEATURE:
<223> OTHER INFORMATION: Primer

<400> SEQUENCE: 142
gcgttgccaa tgatgttaca ga                                              22

<210> SEQ ID NO 143
<211> LENGTH: 21
<212> TYPE: DNA
<213> ORGANISM: Artificial Sequence
<220> FEATURE:
<223> OTHER INFORMATION: Primer

<400> SEQUENCE: 143
gcctgagcga gacgaaatac g                                               21

<210> SEQ ID NO 144
<211> LENGTH: 19
<212> TYPE: DNA
<213> ORGANISM: Artificial Sequence
<220> FEATURE:
<223> OTHER INFORMATION: Primer

<400> SEQUENCE: 144
gcgcgtcayg gaggagttg                                                  19

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
tgcgagcctg taggactcta                                                 20

<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
ggcagcgcaa tgacattctt g                                               21

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
cgggacaacg taagcactac a                                               21

<210> SEQ ID NO 148
<211> LENGTH: 20
<212> TYPE: DNA
<213> ORGANISM: Artificial Sequence
<220> FEATURE:
<223> OTHER INFORMATION: Primer

<400> SEQUENCE: 148
```
ccacggcgct ttaagtcctc                                          20

<210> SEQ ID NO 149
<211> LENGTH: 28
<212> TYPE: DNA
<213> ORGANISM: Artificial Sequence
<220> FEATURE:
<223> OTHER INFORMATION: Primer

<400> SEQUENCE: 149
catgtaaacc acgacgtttt aaatcttc                                 28

<210> SEQ ID NO 150
<211> LENGTH: 23
<212> TYPE: DNA
<213> ORGANISM: Artificial Sequence
<220> FEATURE:
<223> OTHER INFORMATION: Primer

<400> SEQUENCE: 150
ggagctgaac ttgctatgtc act                                      23

<210> SEQ ID NO 151
<211> LENGTH: 21
<212> TYPE: DNA
<213> ORGANISM: Artificial Sequence
<220> FEATURE:
<223> OTHER INFORMATION: Primer

<400> SEQUENCE: 151
gctgcgacac tggacacaat c                                        21

<210> SEQ ID NO 152
<211> LENGTH: 22
<212> TYPE: DNA
<213> ORGANISM: Artificial Sequence
<220> FEATURE:
<223> OTHER INFORMATION: Primer

<400> SEQUENCE: 152
cgcttcgagc gacaacagtt ag                                       22

<210> SEQ ID NO 153
<211> LENGTH: 24
<212> TYPE: DNA
<213> ORGANISM: Artificial Sequence
<220> FEATURE:
<223> OTHER INFORMATION: Primer

<400> SEQUENCE: 153
actattctgc ctatcctaat tggg                                     24

<210> SEQ ID NO 154
<211> LENGTH: 24
<212> TYPE: DNA
<213> ORGANISM: Artificial Sequence
<220> FEATURE:
<223> OTHER INFORMATION: Primer

<400> SEQUENCE: 154
tcatttaatg ttgcgactct ttca                                     24

<210> SEQ ID NO 155
<211> LENGTH: 22
<212> TYPE: DNA

```
<213> ORGANISM: Artificial Sequence
<220> FEATURE:
<223> OTHER INFORMATION: Primer

<400> SEQUENCE: 155
gaattggact gcctctacga tt                                         22

<210> SEQ ID NO 156
<211> LENGTH: 18
<212> TYPE: DNA
<213> ORGANISM: Artificial Sequence
<220> FEATURE:
<223> OTHER INFORMATION: Primer

<400> SEQUENCE: 156
gcacgcccat acagatgt                                              18

<210> SEQ ID NO 157
<211> LENGTH: 17
<212> TYPE: DNA
<213> ORGANISM: Artificial Sequence
<220> FEATURE:
<223> OTHER INFORMATION: Primer

<400> SEQUENCE: 157
aaggcatgga ggcgaac                                               17

<210> SEQ ID NO 158
<211> LENGTH: 26
<212> TYPE: DNA
<213> ORGANISM: Artificial Sequence
<220> FEATURE:
<223> OTHER INFORMATION: Primer

<400> SEQUENCE: 158
aagtatataa gttctgttcc gatggt                                     26

<210> SEQ ID NO 159
<211> LENGTH: 24
<212> TYPE: DNA
<213> ORGANISM: Artificial Sequence
<220> FEATURE:
<223> OTHER INFORMATION: Primer

<400> SEQUENCE: 159
aatactccac actttatcca ccaa                                       24

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
ttcttgcgaa cctccttctc                                            20

<210> SEQ ID NO 161
<211> LENGTH: 19
<212> TYPE: DNA
<213> ORGANISM: Artificial Sequence
<220> FEATURE:
<223> OTHER INFORMATION: Primer

<400> SEQUENCE: 161
aacgatgcga cgatccatt                                             19
```

```
<210> SEQ ID NO 162
<211> LENGTH: 18
<212> TYPE: DNA
<213> ORGANISM: Artificial Sequence
<220> FEATURE:
<223> OTHER INFORMATION: Primer

<400> SEQUENCE: 162
gcgatttgct gtgcgaaa                                                   18

<210> SEQ ID NO 163
<211> LENGTH: 21
<212> TYPE: DNA
<213> ORGANISM: Artificial Sequence
<220> FEATURE:
<223> OTHER INFORMATION: Primer

<400> SEQUENCE: 163
ccgcttgctg gtacatatct a                                               21

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
cctatctcgt ccgctatctg                                                 20

<210> SEQ ID NO 165
<211> LENGTH: 19
<212> TYPE: DNA
<213> ORGANISM: Artificial Sequence
<220> FEATURE:
<223> OTHER INFORMATION: Primer

<400> SEQUENCE: 165
aatggctgtt ggttggacg                                                  19

<210> SEQ ID NO 166
<211> LENGTH: 23
<212> TYPE: DNA
<213> ORGANISM: Artificial Sequence
<220> FEATURE:
<223> OTHER INFORMATION: Primer

<400> SEQUENCE: 166
catactttcg gttgggtaat gct                                             23

<210> SEQ ID NO 167
<211> LENGTH: 23
<212> TYPE: DNA
<213> ORGANISM: Artificial Sequence
<220> FEATURE:
<223> OTHER INFORMATION: Primer

<400> SEQUENCE: 167
aatatgccgt tgtaactcgt tca                                             23

<210> SEQ ID NO 168
<211> LENGTH: 24
<212> TYPE: DNA
<213> ORGANISM: Artificial Sequence
<220> FEATURE:
```

```
<223> OTHER INFORMATION: Primer

<400> SEQUENCE: 168
acacaatcac atgatccgtt atcg                                              24

<210> SEQ ID NO 169
<211> LENGTH: 24
<212> TYPE: DNA
<213> ORGANISM: Artificial Sequence
<220> FEATURE:
<223> OTHER INFORMATION: Primer

<400> SEQUENCE: 169
agtatgcagt tgtaactcgc tcta                                              24

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
caccaccacc agaaacgata ac                                                22

<210> SEQ ID NO 171
<211> LENGTH: 18
<212> TYPE: DNA
<213> ORGANISM: Artificial Sequence
<220> FEATURE:
<223> OTHER INFORMATION: Primer

<400> SEQUENCE: 171
gtgattggtt gcggtcca                                                     18

<210> SEQ ID NO 172
<211> LENGTH: 18
<212> TYPE: DNA
<213> ORGANISM: Artificial Sequence
<220> FEATURE:
<223> OTHER INFORMATION: Primer

<400> SEQUENCE: 172
cccgccacca gacactat                                                     18

<210> SEQ ID NO 173
<211> LENGTH: 22
<212> TYPE: DNA
<213> ORGANISM: Artificial Sequence
<220> FEATURE:
<223> OTHER INFORMATION: Primer

<400> SEQUENCE: 173
ygagaatgga gtaattggct ct                                                22

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
watttcacca ccaccagaaa caaa                                              24
```

```
<210> SEQ ID NO 175
<211> LENGTH: 18
<212> TYPE: DNA
<213> ORGANISM: Artificial Sequence
<220> FEATURE:
<223> OTHER INFORMATION: Primer

<400> SEQUENCE: 175
gggwgccaat cgggttat                                                 18

<210> SEQ ID NO 176
<211> LENGTH: 18
<212> TYPE: DNA
<213> ORGANISM: Artificial Sequence
<220> FEATURE:
<223> OTHER INFORMATION: Primer

<400> SEQUENCE: 176
ctcagtgagt ctgcgaaa                                                 18

<210> SEQ ID NO 177
<211> LENGTH: 18
<212> TYPE: DNA
<213> ORGANISM: Artificial Sequence
<220> FEATURE:
<223> OTHER INFORMATION: Primer

<400> SEQUENCE: 177
ctcggtgagc ctgcgaaa                                                 18

<210> SEQ ID NO 178
<211> LENGTH: 21
<212> TYPE: DNA
<213> ORGANISM: Artificial Sequence
<220> FEATURE:
<223> OTHER INFORMATION: Primer

<400> SEQUENCE: 178
aaagactacg agcagaatgg c                                             21

<210> SEQ ID NO 179
<211> LENGTH: 24
<212> TYPE: DNA
<213> ORGANISM: Artificial Sequence
<220> FEATURE:
<223> OTHER INFORMATION: Primer

<400> SEQUENCE: 179
acggtaagtg aagtaagtgt gaag                                          24

<210> SEQ ID NO 180
<211> LENGTH: 19
<212> TYPE: DNA
<213> ORGANISM: Artificial Sequence
<220> FEATURE:
<223> OTHER INFORMATION: Primer

<400> SEQUENCE: 180
aacgctgcca ttgttacca                                                19

<210> SEQ ID NO 181
<211> LENGTH: 21
<212> TYPE: DNA
<213> ORGANISM: Artificial Sequence
<220> FEATURE:
<223> OTHER INFORMATION: Primer
```

<400> SEQUENCE: 181
aagccttgaa gtgttctgga g                                                  21

<210> SEQ ID NO 182
<211> LENGTH: 23
<212> TYPE: DNA
<213> ORGANISM: Artificial Sequence
<220> FEATURE:
<223> OTHER INFORMATION: Primer

<400> SEQUENCE: 182
aagacaggag gtatcggatt tga                                                23

<210> SEQ ID NO 183
<211> LENGTH: 22
<212> TYPE: DNA
<213> ORGANISM: Artificial Sequence
<220> FEATURE:
<223> OTHER INFORMATION: Primer

<400> SEQUENCE: 183
cgtaggcagc taagttctcg ta                                                 22

<210> SEQ ID NO 184
<211> LENGTH: 23
<212> TYPE: DNA
<213> ORGANISM: Artificial Sequence
<220> FEATURE:
<223> OTHER INFORMATION: Primer

<400> SEQUENCE: 184
aagaccgcat caatatcgtc atc                                                23

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
catagcaagc cgtccaagaa                                                    20

<210> SEQ ID NO 186
<211> LENGTH: 24
<212> TYPE: DNA
<213> ORGANISM: Artificial Sequence
<220> FEATURE:
<223> OTHER INFORMATION: Primer

<400> SEQUENCE: 186
aagactctta cgaaccatgt tgtt                                               24

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187
cctctggctc ggaatctatt g                                                  21

<210> SEQ ID NO 188
<211> LENGTH: 23

```
<212> TYPE: DNA
<213> ORGANISM: Artificial Sequence
<220> FEATURE:
<223> OTHER INFORMATION: Primer

<400> SEQUENCE: 188
aagcactgac ctataaccaa tgg                                          23

<210> SEQ ID NO 189
<211> LENGTH: 22
<212> TYPE: DNA
<213> ORGANISM: Artificial Sequence
<220> FEATURE:
<223> OTHER INFORMATION: Primer

<400> SEQUENCE: 189
cccaggaatg ttcggaaaga aa                                           22

<210> SEQ ID NO 190
<211> LENGTH: 22
<212> TYPE: DNA
<213> ORGANISM: Artificial Sequence
<220> FEATURE:
<223> OTHER INFORMATION: Primer

<400> SEQUENCE: 190
aagcattcag agacacaacc aa                                           22

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
aaccaacacc accaatgaca t                                            21

<210> SEQ ID NO 192
<211> LENGTH: 24
<212> TYPE: DNA
<213> ORGANISM: Artificial Sequence
<220> FEATURE:
<223> OTHER INFORMATION: Primer

<400> SEQUENCE: 192
aaggtgagca gctaatcttt aagg                                         24

<210> SEQ ID NO 193
<211> LENGTH: 24
<212> TYPE: DNA
<213> ORGANISM: Artificial Sequence
<220> FEATURE:
<223> OTHER INFORMATION: Primer

<400> SEQUENCE: 193
tgaccctgaa attccattct ttga                                         24

<210> SEQ ID NO 194
<211> LENGTH: 22
<212> TYPE: DNA
<213> ORGANISM: Artificial Sequence
<220> FEATURE:
<223> OTHER INFORMATION: Primer

<400> SEQUENCE: 194
```

-continued aagtcgcaca acatcttgaa gg                                                    22

<210> SEQ ID NO 195
<211> LENGTH: 24
<212> TYPE: DNA
<213> ORGANISM: Artificial Sequence
<220> FEATURE:
<223> OTHER INFORMATION: Primer

<400> SEQUENCE: 195
agatttgagc accaccaata atga                                                  24

<210> SEQ ID NO 196
<211> LENGTH: 24
<212> TYPE: DNA
<213> ORGANISM: Artificial Sequence
<220> FEATURE:
<223> OTHER INFORMATION: Primer

<400> SEQUENCE: 196
aatcaatatc acgacagcga tcaa                                                  24

<210> SEQ ID NO 197
<211> LENGTH: 19
<212> TYPE: DNA
<213> ORGANISM: Artificial Sequence
<220> FEATURE:
<223> OTHER INFORMATION: Primer

<400> SEQUENCE: 197
cttcacggga tgggtctca                                                        19

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
aatcagtggc tccttgttgg                                                       20

<210> SEQ ID NO 199
<211> LENGTH: 24
<212> TYPE: DNA
<213> ORGANISM: Artificial Sequence
<220> FEATURE:
<223> OTHER INFORMATION: Primer

<400> SEQUENCE: 199
ggaagaacac ccatagagtc aaat                                                  24

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
aatcagtggc ttcttgtcgg                                                       20

<210> SEQ ID NO 201
<211> LENGTH: 24
<212> TYPE: DNA
<213> ORGANISM: Artificial Sequence -continued

```
<220> FEATURE:
<223> OTHER INFORMATION: Primer

<400> SEQUENCE: 201
gtggatgata gataagtgga tggt                                      24

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
aatggcgtaa tcggtagtgg                                           20

<210> SEQ ID NO 203
<211> LENGTH: 23
<212> TYPE: DNA
<213> ORGANISM: Artificial Sequence
<220> FEATURE:
<223> OTHER INFORMATION: Primer

<400> SEQUENCE: 203
gcttgaaatt ccgttctttg aca                                       23

<210> SEQ ID NO 204
<211> LENGTH: 19
<212> TYPE: DNA
<213> ORGANISM: Artificial Sequence
<220> FEATURE:
<223> OTHER INFORMATION: Primer

<400> SEQUENCE: 204
acgcattgct gtcattggt                                            19

<210> SEQ ID NO 205
<211> LENGTH: 18
<212> TYPE: DNA
<213> ORGANISM: Artificial Sequence
<220> FEATURE:
<223> OTHER INFORMATION: Primer

<400> SEQUENCE: 205
ctcgctggca ctggaatc                                             18

<210> SEQ ID NO 206
<211> LENGTH: 19
<212> TYPE: DNA
<213> ORGANISM: Artificial Sequence
<220> FEATURE:
<223> OTHER INFORMATION: Primer

<400> SEQUENCE: 206
actctatgcc gaggctctg                                            19

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
cgctgacgac tcaaggtaac                                           20
```

```
<210> SEQ ID NO 208
<211> LENGTH: 18
<212> TYPE: DNA
<213> ORGANISM: Artificial Sequence
<220> FEATURE:
<223> OTHER INFORMATION: Primer

<400> SEQUENCE: 208
watgggagat cgcgtgcg                                                 18

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
gcwgtaccac ccgacaatct                                               20

<210> SEQ ID NO 210
<211> LENGTH: 18
<212> TYPE: DNA
<213> ORGANISM: Artificial Sequence
<220> FEATURE:
<223> OTHER INFORMATION: Primer

<400> SEQUENCE: 210
gcagggtcaa gtygtcgg                                                 18

<210> SEQ ID NO 211
<211> LENGTH: 18
<212> TYPE: DNA
<213> ORGANISM: Artificial Sequence
<220> FEATURE:
<223> OTHER INFORMATION: Primer

<400> SEQUENCE: 211
tcggactcga csgcatag                                                 18

<210> SEQ ID NO 212
<211> LENGTH: 18
<212> TYPE: DNA
<213> ORGANISM: Artificial Sequence
<220> FEATURE:
<223> OTHER INFORMATION: Primer

<400> SEQUENCE: 212
acccgacaac ttgaccct                                                 18

<210> SEQ ID NO 213
<211> LENGTH: 21
<212> TYPE: DNA
<213> ORGANISM: Artificial Sequence
<220> FEATURE:
<223> OTHER INFORMATION: Primer

<400> SEQUENCE: 213
accaacacaa caatggagtc a                                             21

<210> SEQ ID NO 214
<211> LENGTH: 19
<212> TYPE: DNA
<213> ORGANISM: Artificial Sequence
<220> FEATURE:
<223> OTHER INFORMATION: Primer
```

```
<400> SEQUENCE: 214
aatctcaccc aggctcagt                                              19

<210> SEQ ID NO 215
<211> LENGTH: 18
<212> TYPE: DNA
<213> ORGANISM: Artificial Sequence
<220> FEATURE:
<223> OTHER INFORMATION: Primer

<400> SEQUENCE: 215
ccgttcaagc gcagtcat                                               18

<210> SEQ ID NO 216
<211> LENGTH: 20
<212> TYPE: DNA
<213> ORGANISM: Artificial Sequence
<220> FEATURE:
<223> OTHER INFORMATION: Primer

<400> SEQUENCE: 216
gctggtggtt atgcactcag                                             20

<210> SEQ ID NO 217
<211> LENGTH: 19
<212> TYPE: DNA
<213> ORGANISM: Artificial Sequence
<220> FEATURE:
<223> OTHER INFORMATION: Primer

<400> SEQUENCE: 217
cgcccaagaa ggatttccg                                              19

<210> SEQ ID NO 218
<211> LENGTH: 22
<212> TYPE: DNA
<213> ORGANISM: Artificial Sequence
<220> FEATURE:
<223> OTHER INFORMATION: Primer

<400> SEQUENCE: 218
catcattttc ggcatcgtca ac                                          22

<210> SEQ ID NO 219
<211> LENGTH: 18
<212> TYPE: DNA
<213> ORGANISM: Artificial Sequence
<220> FEATURE:
<223> OTHER INFORMATION: Primer

<400> SEQUENCE: 219
gcgacaaggc ataggctt                                               18

<210> SEQ ID NO 220
<211> LENGTH: 24
<212> TYPE: DNA
<213> ORGANISM: Artificial Sequence
<220> FEATURE:
<223> OTHER INFORMATION: Primer

<400> SEQUENCE: 220
aaagccttaa tgacaggttt gagt                                        24

<210> SEQ ID NO 221
```

-continued

```
<210> SEQ ID NO 221
<211> LENGTH: 24
<212> TYPE: DNA
<213> ORGANISM: Artificial Sequence
<220> FEATURE:
<223> OTHER INFORMATION: Primer

<400> SEQUENCE: 221
gaagatggag cagatgtgat tgat                                          24

<210> SEQ ID NO 222
<211> LENGTH: 20
<212> TYPE: DNA
<213> ORGANISM: Artificial Sequence
<220> FEATURE:
<223> OTHER INFORMATION: Primer

<400> SEQUENCE: 222
cgcaagatgt ggcgtgttac                                               20

<210> SEQ ID NO 223
<211> LENGTH: 23
<212> TYPE: DNA
<213> ORGANISM: Artificial Sequence
<220> FEATURE:
<223> OTHER INFORMATION: Primer

<400> SEQUENCE: 223
aracggcatg atgaacctga atc                                           23

<210> SEQ ID NO 224
<211> LENGTH: 18
<212> TYPE: DNA
<213> ORGANISM: Artificial Sequence
<220> FEATURE:
<223> OTHER INFORMATION: Primer

<400> SEQUENCE: 224
tcgccacagc ggtatctg                                                 18

<210> SEQ ID NO 225
<211> LENGTH: 21
<212> TYPE: DNA
<213> ORGANISM: Artificial Sequence
<220> FEATURE:
<223> OTHER INFORMATION: Primer

<400> SEQUENCE: 225
gggaaacaca agacagaccg a                                             21

<210> SEQ ID NO 226
<211> LENGTH: 21
<212> TYPE: DNA
<213> ORGANISM: Artificial Sequence
<220> FEATURE:
<223> OTHER INFORMATION: Primer

<400> SEQUENCE: 226
ggcgacggcc aattctactt g                                             21

<210> SEQ ID NO 227
<211> LENGTH: 18
<212> TYPE: DNA
<213> ORGANISM: Artificial Sequence
<220> FEATURE:
<223> OTHER INFORMATION: Primer

<400> SEQUENCE: 227
```

```
gacggccgat cctgcttg                                                  18
```

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228

```
aacgccagca ycgaactgaa                                                20
```

<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229

```
aacgccagha tcgaactgaa                                                20
```

<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230

```
gccgatacct cccaactgta c                                              21
```

<210> SEQ ID NO 231
<211> LENGTH: 19
<212> TYPE: DNA
<213> ORGANISM: Artificial Sequence
<220> FEATURE:
<223> OTHER INFORMATION: Primer

<400> SEQUENCE: 231

```
gaacggcagg cgattcttg                                                 19
```

<210> SEQ ID NO 232
<211> LENGTH: 19
<212> TYPE: DNA
<213> ORGANISM: Artificial Sequence
<220> FEATURE:
<223> OTHER INFORMATION: Primer

<400> SEQUENCE: 232

```
gcgctgccca gttctcttc                                                 19
```

<210> SEQ ID NO 233
<211> LENGTH: 18
<212> TYPE: DNA
<213> ORGANISM: Artificial Sequence
<220> FEATURE:
<223> OTHER INFORMATION: Primer

<400> SEQUENCE: 233

```
cccgcaatgc cgtcaatc                                                  18
```

<210> SEQ ID NO 234
<211> LENGTH: 23
<212> TYPE: DNA

```
<213> ORGANISM: Artificial Sequence
<220> FEATURE:
<223> OTHER INFORMATION: Primer

<400> SEQUENCE: 234
cgtttcgcaa cctgttctca ttg                                              23

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
cccggcatat tcgagcaaca tc                                               22

<210> SEQ ID NO 236
<211> LENGTH: 19
<212> TYPE: DNA
<213> ORGANISM: Artificial Sequence
<220> FEATURE:
<223> OTHER INFORMATION: Primer

<400> SEQUENCE: 236
tggcagcgac aaagtcatc                                                   19

<210> SEQ ID NO 237
<211> LENGTH: 21
<212> TYPE: DNA
<213> ORGANISM: Artificial Sequence
<220> FEATURE:
<223> OTHER INFORMATION: Primer

<400> SEQUENCE: 237
tgccgtgtat gttcagctat c                                                21

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
ttgccgcatt tggcattctg                                                  20

<210> SEQ ID NO 239
<211> LENGTH: 21
<212> TYPE: DNA
<213> ORGANISM: Artificial Sequence
<220> FEATURE:
<223> OTHER INFORMATION: Primer

<400> SEQUENCE: 239
cgcttgccgc atttggtatt c                                                21

<210> SEQ ID NO 240
<211> LENGTH: 15
<212> TYPE: DNA
<213> ORGANISM: Artificial Sequence
<220> FEATURE:
<223> OTHER INFORMATION: Primer

<400> SEQUENCE: 240
gcgccggcat tccga                                                       15
```

```
<210> SEQ ID NO 241
<211> LENGTH: 23
<212> TYPE: DNA
<213> ORGANISM: Artificial Sequence
<220> FEATURE:
<223> OTHER INFORMATION: Primer

<400> SEQUENCE: 241
tcgctgcgtt gctaaatatt gtc                                           23

<210> SEQ ID NO 242
<211> LENGTH: 21
<212> TYPE: DNA
<213> ORGANISM: Artificial Sequence
<220> FEATURE:
<223> OTHER INFORMATION: Primer

<400> SEQUENCE: 242
attccaagcc tttgtggcag g                                             21

<210> SEQ ID NO 243
<211> LENGTH: 16
<212> TYPE: DNA
<213> ORGANISM: Artificial Sequence
<220> FEATURE:
<223> OTHER INFORMATION: Primer

<400> SEQUENCE: 243
ccacgaccgt cggctt                                                   16

<210> SEQ ID NO 244
<211> LENGTH: 21
<212> TYPE: DNA
<213> ORGANISM: Artificial Sequence
<220> FEATURE:
<223> OTHER INFORMATION: Primer

<400> SEQUENCE: 244
caccacgact gttggtttgt c                                             21

<210> SEQ ID NO 245
<211> LENGTH: 19
<212> TYPE: DNA
<213> ORGANISM: Artificial Sequence
<220> FEATURE:
<223> OTHER INFORMATION: Primer

<400> SEQUENCE: 245
acaccgcgac cgttggttt                                                19

<210> SEQ ID NO 246
<211> LENGTH: 20
<212> TYPE: DNA
<213> ORGANISM: Artificial Sequence
<220> FEATURE:
<223> OTHER INFORMATION: Primer

<400> SEQUENCE: 246
gcgtgrcaaa agccagaaga                                               20

<210> SEQ ID NO 247
<211> LENGTH: 23
<212> TYPE: DNA
<213> ORGANISM: Artificial Sequence
<220> FEATURE:
```

```
<223> OTHER INFORMATION: Primer

<400> SEQUENCE: 247
tgaacagcat tctcgctatc aaa                                              23

<210> SEQ ID NO 248
<211> LENGTH: 19
<212> TYPE: DNA
<213> ORGANISM: Artificial Sequence
<220> FEATURE:
<223> OTHER INFORMATION: Primer

<400> SEQUENCE: 248
cagccgcttt cgtcaaacg                                                   19

<210> SEQ ID NO 249
<211> LENGTH: 25
<212> TYPE: DNA
<213> ORGANISM: Artificial Sequence
<220> FEATURE:
<223> OTHER INFORMATION: Primer

<400> SEQUENCE: 249
aagagtattg gttgacwgca ggatt                                            25

<210> SEQ ID NO 250
<211> LENGTH: 26
<212> TYPE: DNA
<213> ORGANISM: Artificial Sequence
<220> FEATURE:
<223> OTHER INFORMATION: Primer

<400> SEQUENCE: 250
tgttagccgt ggataatggt ttacaa                                           26

<210> SEQ ID NO 251
<211> LENGTH: 22
<212> TYPE: DNA
<213> ORGANISM: Artificial Sequence
<220> FEATURE:
<223> OTHER INFORMATION: Primer

<400> SEQUENCE: 251
gcgagcttgg tgtcgatatt ga                                               22

<210> SEQ ID NO 252
<211> LENGTH: 23
<212> TYPE: DNA
<213> ORGANISM: Artificial Sequence
<220> FEATURE:
<223> OTHER INFORMATION: Primer

<400> SEQUENCE: 252
gtgatgagtg gagaggctaa tgc                                              23

<210> SEQ ID NO 253
<211> LENGTH: 19
<212> TYPE: DNA
<213> ORGANISM: Artificial Sequence
<220> FEATURE:
<223> OTHER INFORMATION: Primer

<400> SEQUENCE: 253
gccgccgagt gatacaagt                                                   19
```

-continued

```
<210> SEQ ID NO 254
<211> LENGTH: 21
<212> TYPE: DNA
<213> ORGANISM: Artificial Sequence
<220> FEATURE:
<223> OTHER INFORMATION: Primer

<400> SEQUENCE: 254
ggtagcaggt tcatccaggt t                                           21

<210> SEQ ID NO 255
<211> LENGTH: 22
<212> TYPE: DNA
<213> ORGANISM: Artificial Sequence
<220> FEATURE:
<223> OTHER INFORMATION: Primer

<400> SEQUENCE: 255
gctatgcctc cgccaattat ga                                          22

<210> SEQ ID NO 256
<211> LENGTH: 25
<212> TYPE: DNA
<213> ORGANISM: Artificial Sequence
<220> FEATURE:
<223> OTHER INFORMATION: Primer

<400> SEQUENCE: 256
cactattacc acgccaactg ttact                                       25

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
agccgctgtg tcttacgatg                                             20

<210> SEQ ID NO 258
<211> LENGTH: 24
<212> TYPE: DNA
<213> ORGANISM: Artificial Sequence
<220> FEATURE:
<223> OTHER INFORMATION: Primer

<400> SEQUENCE: 258
cgatctcttc cataaacgcc tgat                                        24

<210> SEQ ID NO 259
<211> LENGTH: 19
<212> TYPE: DNA
<213> ORGANISM: Artificial Sequence
<220> FEATURE:
<223> OTHER INFORMATION: Primer

<400> SEQUENCE: 259
aaacgacggc gaacccatt                                              19

<210> SEQ ID NO 260
<211> LENGTH: 20
<212> TYPE: DNA
<213> ORGANISM: Artificial Sequence
<220> FEATURE:
<223> OTHER INFORMATION: Primer
```

```
<400> SEQUENCE: 260
cgacttcact ggcggaatcc                                                 20

<210> SEQ ID NO 261
<211> LENGTH: 17
<212> TYPE: DNA
<213> ORGANISM: Artificial Sequence
<220> FEATURE:
<223> OTHER INFORMATION: Primer

<400> SEQUENCE: 261
attgcggcgg acgagag                                                    17

<210> SEQ ID NO 262
<211> LENGTH: 17
<212> TYPE: DNA
<213> ORGANISM: Artificial Sequence
<220> FEATURE:
<223> OTHER INFORMATION: Primer

<400> SEQUENCE: 262
gctgacgacg gcgaaca                                                    17

<210> SEQ ID NO 263
<211> LENGTH: 18
<212> TYPE: DNA
<213> ORGANISM: Artificial Sequence
<220> FEATURE:
<223> OTHER INFORMATION: Primer

<400> SEQUENCE: 263
cgccgacatg ccgactat                                                   18

<210> SEQ ID NO 264
<211> LENGTH: 16
<212> TYPE: DNA
<213> ORGANISM: Artificial Sequence
<220> FEATURE:
<223> OTHER INFORMATION: Primer

<400> SEQUENCE: 264
cgccgcctgc ctgaat                                                     16

<210> SEQ ID NO 265
<211> LENGTH: 19
<212> TYPE: DNA
<213> ORGANISM: Artificial Sequence
<220> FEATURE:
<223> OTHER INFORMATION: Primer

<400> SEQUENCE: 265
gcagaaccga tggcgatgt                                                  19

<210> SEQ ID NO 266
<211> LENGTH: 17
<212> TYPE: DNA
<213> ORGANISM: Artificial Sequence
<220> FEATURE:
<223> OTHER INFORMATION: Primer

<400> SEQUENCE: 266
gcgtcaggcg gcgaata                                                    17

<210> SEQ ID NO 267
<211> LENGTH: 27
```

```
<212> TYPE: DNA
<213> ORGANISM: Artificial Sequence
<220> FEATURE:
<223> OTHER INFORMATION: Primer

<400> SEQUENCE: 267
gaagagtgtt atgtctatga gcgtcaa                                          27

<210> SEQ ID NO 268
<211> LENGTH: 18
<212> TYPE: DNA
<213> ORGANISM: Artificial Sequence
<220> FEATURE:
<223> OTHER INFORMATION: Primer

<400> SEQUENCE: 268
tgcgttctgc gtcgttgt                                                    18

<210> SEQ ID NO 269
<211> LENGTH: 16
<212> TYPE: DNA
<213> ORGANISM: Artificial Sequence
<220> FEATURE:
<223> OTHER INFORMATION: Primer

<400> SEQUENCE: 269
ggcggcaagc gagtca                                                      16

<210> SEQ ID NO 270
<211> LENGTH: 22
<212> TYPE: DNA
<213> ORGANISM: Artificial Sequence
<220> FEATURE:
<223> OTHER INFORMATION: Primer

<400> SEQUENCE: 270
tcaggcgtga agtattcgtt gg                                               22

<210> SEQ ID NO 271
<211> LENGTH: 22
<212> TYPE: DNA
<213> ORGANISM: Artificial Sequence
<220> FEATURE:
<223> OTHER INFORMATION: Primer

<400> SEQUENCE: 271
ccgaactgga acagcagatt ca                                               22

<210> SEQ ID NO 272
<211> LENGTH: 19
<212> TYPE: DNA
<213> ORGANISM: Artificial Sequence
<220> FEATURE:
<223> OTHER INFORMATION: Primer

<400> SEQUENCE: 272
gcatcgccgt taccgtcaa                                                   19

<210> SEQ ID NO 273
<211> LENGTH: 23
<212> TYPE: DNA
<213> ORGANISM: Artificial Sequence
<220> FEATURE:
<223> OTHER INFORMATION: Primer

<400> SEQUENCE: 273
```

```
ccactggtaa acgtttatc ctc                                           23

<210> SEQ ID NO 274
<211> LENGTH: 23
<212> TYPE: DNA
<213> ORGANISM: Artificial Sequence
<220> FEATURE:
<223> OTHER INFORMATION: Primer

<400> SEQUENCE: 274
ccgctggtaa aaggtttatc ctc                                          23

<210> SEQ ID NO 275
<211> LENGTH: 21
<212> TYPE: DNA
<213> ORGANISM: Artificial Sequence
<220> FEATURE:
<223> OTHER INFORMATION: Primer

<400> SEQUENCE: 275
gaactggcac msaaatatcc c                                            21

<210> SEQ ID NO 276
<211> LENGTH: 27
<212> TYPE: DNA
<213> ORGANISM: Artificial Sequence
<220> FEATURE:
<223> OTHER INFORMATION: Primer

<400> SEQUENCE: 276
aacgacactg cttaaccaca tcctgaa                                      27

<210> SEQ ID NO 277
<211> LENGTH: 27
<212> TYPE: DNA
<213> ORGANISM: Artificial Sequence
<220> FEATURE:
<223> OTHER INFORMATION: Primer

<400> SEQUENCE: 277
aacgacactg cttaaccata ttctgaa                                      27

<210> SEQ ID NO 278
<211> LENGTH: 21
<212> TYPE: DNA
<213> ORGANISM: Artificial Sequence
<220> FEATURE:
<223> OTHER INFORMATION: Primer

<400> SEQUENCE: 278
cggtggactc aatgacaagc t                                            21

<210> SEQ ID NO 279
<211> LENGTH: 21
<212> TYPE: DNA
<213> ORGANISM: Artificial Sequence
<220> FEATURE:
<223> OTHER INFORMATION: Primer

<400> SEQUENCE: 279
cggtagactc aataacaagc t                                            21

<210> SEQ ID NO 280
<211> LENGTH: 20
<212> TYPE: DNA
<213> ORGANISM: Artificial Sequence
```

```
<220> FEATURE:
<223> OTHER INFORMATION: Primer

<400> SEQUENCE: 280
cgcgagygct ttctatcttg                                              20

<210> SEQ ID NO 281
<211> LENGTH: 20
<212> TYPE: DNA
<213> ORGANISM: Artificial Sequence
<220> FEATURE:
<223> OTHER INFORMATION: Primer

<400> SEQUENCE: 281
gagasccact ggttccagaa                                              20

<210> SEQ ID NO 282
<211> LENGTH: 17
<212> TYPE: DNA
<213> ORGANISM: Artificial Sequence
<220> FEATURE:
<223> OTHER INFORMATION: Primer

<400> SEQUENCE: 282
acccaactga atggagc                                                 17

<210> SEQ ID NO 283
<211> LENGTH: 19
<212> TYPE: DNA
<213> ORGANISM: Artificial Sequence
<220> FEATURE:
<223> OTHER INFORMATION: Primer

<400> SEQUENCE: 283
acgcacttga cttgtcttc                                               19

<210> SEQ ID NO 284
<211> LENGTH: 37
<212> TYPE: DNA
<213> ORGANISM: Artificial Sequence
<220> FEATURE:
<223> OTHER INFORMATION: Primer

<400> SEQUENCE: 284
acccaactga atggagccgc gagygctttc tatcttg                           37

<210> SEQ ID NO 285
<211> LENGTH: 39
<212> TYPE: DNA
<213> ORGANISM: Artificial Sequence
<220> FEATURE:
<223> OTHER INFORMATION: Primer

<400> SEQUENCE: 285
acgcacttga cttgtcttcg agasccactg gttccagaa                         39
```